(12) United States Patent
Conneely et al.

(10) Patent No.: US 6,635,447 B1
(45) Date of Patent: *Oct. 21, 2003

(54) PRODUCTION OF RECOMBINANT LACTOFERRIN AND LACTOFERRIN POLYPEPTIDES USING CDNA SEQUENCES IN VARIOUS ORGANISMS

(75) Inventors: Orla M. Conneely, Houston, TX (US); Denis R. Headon, Galway (IE); Bert W. O'Malley, Houston, TX (US); Gregory S. May, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/633,739

(22) Filed: Aug. 7, 2000

Related U.S. Application Data

(60) Division of application No. 08/456,108, filed on May 30, 1995, now Pat. No. 6,100,054, which is a division of application No. 08/145,681, filed on Oct. 28, 1993, now Pat. No. 5,571,691, which is a continuation-in-part of application No. 07/967,947, filed on Oct. 27, 1992, now abandoned, which is a continuation of application No. 07/348,270, filed on May 5, 1989, now abandoned, application No. 09/633,738, which is a continuation-in-part of application No. 07/878,307, filed on Apr. 24, 1992, now abandoned.

(51) Int. Cl.[7] ................................................. C12P 21/06
(52) U.S. Cl. ........................ 435/69.1; 435/6; 435/252.2; 435/240.2; 435/320.1
(58) Field of Search ......................... 435/6, 69.1, 252.2, 435/240.2, 320.1

(56) References Cited

U.S. PATENT DOCUMENTS

| | | | |
|---|---|---|---|
| 4,289,690 A | 9/1981 | Pestka et al. | 260/112 |
| 4,394,443 A | 7/1983 | Weisiman et al. | 435/6 |
| 4,668,771 A | 5/1987 | Kawakami et al. | 530/366 |
| 4,726,948 A | 2/1988 | Prieels et al. | 424/94.4 |
| 4,800,159 A | 1/1989 | Mullis et al. | 435/172.3 |
| 5,571,691 A | * 11/1996 | Conneely et al. | 435/69.1 |
| 6,100,054 A | * 8/2000 | Conneely et al. | 435/69.1 |

FOREIGN PATENT DOCUMENTS

| | | |
|---|---|---|
| JP | 6016669 | 8/1985 |
| WO | WO 07838 | 12/1987 |

OTHER PUBLICATIONS

Sawatzki, "The role of iron–binding proteins in bacterial infections," *Iron Transport in Microbes, Plants and Animals*, edited by G. Winkelmann et al., pp. 478–488.

Spik, et al., "Characterization and properties of the human and bovine lactotransferrins extracted from the faeces of newborn infants," *Acta Poediatr Scand.*, 71:979–985 (1982).

Tenovuo et al., "Antimicrobial factors in whole saliva of human infants," *Infection and Immunity*, 51(1):49–53 (1986).

Theil and Aisen, "The storage and transport of iron in animal cells", *Iron Transport in Microbes, Plants and Animals*, edited by G. Winkelmann et al., pp. 491–520 (1987).

Wang, et al. 1984, *Comp. Biochem. Physiol,.* 78B(3):575–580 (abstract).

Yahubovskaya et al. 1986, *Vapr. Med. Khim* 32(6):75–70 (abstract).

Zang, et al. 1984, *Proc. Natl. and Sci.* 81:2752–2756.

Ambruso and Johnston, "Lactoferrin enhances hydroxyl radical production by human neutrophils, neutrophil particulate fractions, and an enzymatic generating system," *J. Clin. Invest.*, 67:352–360 (1987).

Anderson, "Structure of human lactoferrin at 3.2–A resolution," *Proc. Nat'l Acad. Sci. USA*, 84:1769–1773 (1987).

Broxmeyer, "Potential therapeutic usefulness of lactoferrin in leukemia," *Nestle Research News*, 93 (1984/85).

Metz–Boutigue, et al., "Human lactotransferrin: amino acid sequence and structural comparisons with other transferrins," *Eur. J. Biochem.*, 145:659–676 (1984).

Montreuil et al., "Human lactotransferrin : structure and function," *Proteins*, Elsevier Sci. Publs., pp. 25–38 (1985).

Pentecost and Teng, "Lactotransferrin is the major estrogen inducible protein of mouse uterine secretions," *J. Biol., Chem*, 262U(21):10134–10139 (1987).

Rado, et al., "Isolation of lactoferrin cDNA from a human myeloid library and expression of mRNA during normal and leukemic myelopoiesis", *Blood*, 70(4):989–993 (1987).

Reiter, "Protective proteins in milk—biological significance and exploitation," *Int'l Dairy Fed.*, Bulletin No. 191 (1985).

\* cited by examiner

*Primary Examiner*—Christopher S. F. Low
*Assistant Examiner*—Hope A. Robinson
(74) *Attorney, Agent, or Firm*—Fulbright & Jaworski, L.L.P.

(57) ABSTRACT

The verified cDNA sequences for human, bovine and porcine lactoferrin protein have been used to prepare recombinant lactoferrin for therapeutic and nutritional applications. Regions of the cDNA such as the Fe binding sites can be used to make an hLF polypeptide product.

The present invention provides novel plasmids, transfected eucaryotic cells and methods of producing these plasmids and transfected eucaryotic cells. The novel plasmid contains the cDNA for lactoferrin protein. Methods for the production of lactoferrin protein in fungi and bacteria are also provided. Thus, the present invention provides an efficient and economical means for the production of recombinant lactoferrin protein and lactoferrin related polypeptides.

11 Claims, 65 Drawing Sheets

```
                                                    1
                                              GAATTCC GACCGCAGAC
  18
   ATG AAA CTT GTC TTC CTC GTC CTG CTG TTC CTC GGG GCC CTC GGA CTG
   met lys leu val phe leu val leu leu phe leu gly ala leu gly leu
    1
  66
   TGT CTG GCT GGC CGT AGG AGA AGG AGT GTT CAG TGG TGC ACC GTA TCC
   cys leu ala gly arg arg arg arg ser val gln trp cys thr val ser
    17
 114
   CAA CCC GAG GCC ACA AAA TGC TTC CAA TGG CAA AGG AAT ATG AGA AGA
   gln pro glu ala thr lys cys phe gln trp gln arg asn met arg arg
    33
 162
   GTG CGT GGC CCT CCT GTC AGC TGC ATA AAG AGA GAC TCC CCC ATC CAG
   val arg gly pro pro val ser cys ile lys arg asp ser pro ile gln
    49
 210
   TGT ATC CAG GCC ATT GCG GAA AAC AGG GCC GAT GCT GTG ACC CTT GAT
   cys ile gln ala ile ala glu asn arg ala asp ala val thr leu asp
    65
 258
   GGT GGT TTC ATA TAC GAG GCA GGC CTG GCC CCC TAC AAA CTG CGA CCT
   gly gly phe ile tyr glu ala gly leu ala pro tyr lys leu arg pro
    81
 306
   GTA GCG GCG GAA GTC TAC GGG ACC GAA AGA CAG CCA CGA ACT CAC TAT
   val ala ala glu val tyr gly thr glu arg gln pro arg thr his tyr
    97
 354
   TAT GCC GTG GCT GTG GTG AAG AAG GGC GGC AGC TTT CAG CTG AAC GAA
   tyr ala val ala val val lys lys gly gly ser phe gln leu asn glu
    113
 402
   CTG CAA GGT CTG AAG TCC TGC CAC ACA GGC CTT CGC AGG ACC GCT GGA
   leu gln gly leu lys ser cys his thr gly leu arg arg thr ala gly
    129
 450
   TGG AAT GTG CCT ATA GGG ACA CTT CGT CCA TTC TTG AAT TGG ACG GGT
   trp asn val pro ile gly thr leu arg pro phe leu asn trp thr gly
    145
```

FIG. 2A

498
CCA CCT GAG CCC ATT GAG GCA GCT GTG GCC AGG TTC TTC TCA GCC AGC
pro pro glu pro ile glu ala ala val ala arg phe phe ser ala ser
161

546
TGT GTT CCC GGT GCA GAT AAA GGA CAG TTC CCC AAC CTG TGT CGC CTG
cys val pro gly ala asp lys gly gln phe pro asn leu cys arg leu
177

594
TGT GCG GGG ACA GGG GAA AAC AAA TGT GCC TTC TCC TCC CAG GAA CCG
cys ala gly thr gly glu asn lys cys ala phe ser ser gln glu pro
193

642
TAC TTC AGC TAC TCT GGT GCC TTC AAG TGT CTG AGA GAC GGG GCT GGA
tyr phe ser tyr ser gly ala phe lys cys leu arg asp gly ala gly
209

690
GAC GTG GCT TTT ATC AGA GAG AGC ACA GTG TTT GAG GAC CTG TCA GAC
asp val ala phe ile arg glu ser thr val phe glu asp leu ser asp
225

738
GAG GCT GAA AGG GAC GAG TAT GAG TTA CTC TGC CCA GAC AAC ACT CGG
glu ala glu arg asp glu tyr glu leu leu cys pro asp asn thr arg
241

786
AAG CCA GTG GAC AAG TTC AAA GAC TGC CAT CTG GCC CGG GTC CCT TCT
lys pro val asp lys phe lys asp cys his leu ala arg val pro ser
257

834
CAT GCC GTT GTG GCA CGA AGT GTG AAT GGC AAG GAG GAT GCC ATC TGG
his ala val val ala arg ser val asn gly lys glu asp ala ile trp
273

882
AAT CTT CTC CGC CAG GCA CAG GAA AAG TTT GGA AAG GAC AAG TCA CCG
asn leu leu arg gln ala gln glu lys phe gly lys asp lys ser pro
289

930
AAA TTC CAG CTC TTT GGC TCC CCT AGT GGG CAG AAA GAT CTG CTG TTC
lys phe gln leu phe gly ser pro ser gly gln lys asp leu leu phe
305

978
AAG GAC TCT GCC ATT GGG TTT TCG AGG GTG CCC CCG AGG ATA GAT TCT
lys asp ser ala ile gly phe ser arg val pro pro arg ile asp ser
321

1026
GGG CTG TAC CTT GGC TCC GGC TAC TTC ACT GCC ATC CAG AAC TTG AGG
gly leu tyr leu gly ser gly tyr phe thr ala ile gln asn leu arg
337

FIG. 2B

```
1074
    AAA AGT GAG GAG GAA GTG GCT GCC CGG CGT GCG CGG GTC GTG TGG TGT
    lys ser glu glu glu val ala ala arg arg ala arg val val trp cys
    353
1122
    GCG GTG GGC GAG CAG GAG CTG CGC AAG TGT AAC CAG TGG AGT GGC TTG
    ala val gly glu gln glu leu arg lys cys asn gln trp ser gly leu
    369
1170
    AGC GAA GGC AGC GTG ACC TGC TCC TCG GCC TCC ACC ACA GAG GAC TGC
    ser glu gly ser val thr cys ser ser ala ser thr thr glu asp cys
    385
1218
    ATC GCC CTG GTG CTG AAA GGA GAA GCT GAT GCC ATG AGT TTG GAT GGA
    ile ala leu val leu lys gly glu ala asp ala met ser leu asp gly
    401
1266
    GGA TAT GTG TAC ACT GCA GGC AAA TGT GGT TTG GTG CCT GTC CTG GCA
    gly tyr val tyr thr ala gly lys cys gly leu val pro val leu ala
    417
1314
    GAG AAC TAC AAA TCC CAA CAA AGC AGT GAC CCT GAT CCT AAC TGT GTG
    glu asn tyr lys ser gln gln ser ser asp pro asp pro asn cys val
    433
1362
    GAT AGA CCT GTG GAA GGA TAT CTT GCT GTG GCG GTG GTT AGG AGA TCA
    asp arg pro val glu gly tyr leu ala val ala val val arg arg ser
    449
1410
    GAC ACT AGC CTT ACC TGG AAC TCT GTG AAA GGC AAG AAG TCC TGC CAC
    asp thr ser leu thr trp asn ser val lys gly lys lys ser cys his
    465
1458
    ACC GCC GTG GAC AGG ACT GCA GGC TGG AAT ATC CCC ATG GGC CTG CTC
    thr ala val asp arg thr ala gly trp asn ile pro met gly leu leu
    481
1506
    TTC AAC CAG ACG GGC TCC TGC AAA TTT GAT GAA TAT TTC AGT CAA AGC
    phe asn gln thr gly ser cys lys phe asp glu tyr phe ser gln ser
    497
1554
    TGT GCC CCT GGG TCT GAC CCG AGA TCT AAT CTC TGT GCT CTG TGT ATT
    cys ala pro gly ser asp pro arg ser asn leu cys ala leu cys ile
    513
1602
    GGC GAC GAG CAG GGT GAG AAT AAG TGC GTG CCC AAC AGC AAT GAG AGA
    gly asp glu gln gly glu asn lys cys val pro asn ser asn glu arg
    529
```

FIG. 2C

1650
TAC TAC GGC TAC ACT GGG GCT TTC CGG TGC CTG GCT GAG AAT GCT GGA
tyr tyr gly tyr thr gly ala phe arg cys leu ala glu asn ala gly
545
1698
GAC GTT GCA TTT GTG AAA GAT GTC ACT GTC TTG CAG AAC ACT GAT GGA
asp val ala phe val lys asp val thr val leu gln asn thr asp gly
561
1746
AAT AAC AAT GAG GCA TGG GCT AAG GAT TTG AAG CTG GCA GAC TTT GCG
asn asn asn glu ala trp ala lys asp leu lys leu ala asp phe ala
577
1794
CTG CTG TGC CTC GAT GGC AAA CGG AAG CCT GTG ACT GAG GCT AGA AGC
leu leu cys leu asp gly lys arg lys pro val thr glu ala arg ser
593
1842
TSC CAT CTT GCC ATG GCC CCG AAT CAT GCC GTG GTG TCT CGG ATG GAT
cys his leu ala met ala pro asn his ala val val ser arg met asp
609
1890
AAG GTG GAA CGC CTG AAA CAG GTG CTG CTC CAC CAA CAG GCT AAA TTT
lys val glu arg leu lys gln val leu leu his gln gln ala lys phe
625
1938
GGG AGA AAT GGA TCT GAC TGC CCG GAC AAG TTT TGC TTA TTC CAG TCT
gly arg asn gly ser asp cys pro asp lys phe cys leu phe gln ser
641
1986
GAA ACC AAA AAC CTT CTG TTC AAT GAC AAC ACT GAG TGT CTG GCC AGA
glu thr lys asn leu leu phe asn asp asn thr glu cys leu ala arg
657
2034
CTC CAT GGC AAA ACA ACA TAT GAA AAA TAT TTG GGA CCA CAG TAT GTC
leu his gly lys thr thr tyr glu lys tyr leu gly pro gln tyr val
673
2082
GCA GGC ATT ACT AAT CTG AAA AAG TGC TCA ACC TCC CCC CTC CTG GAA
ala gly ile thr asn leu lys lys cys ser thr ser pro leu leu glu
689
2130
GCC TGT GAA TTC CTC AGG AAG TAA
ala cys glu phe leu arg lys *** ACCGAA GAAGATGGCC CAGCTCCCCA
705
2180
AGAAAGCCTC AGCCATTCAC TGCCCCCAGC TCTTCTCCCC AGGTGTGTTG GGGCCTTGGC
2240
TCCCCTGCTG AAGGTGGGGA TTGCCCATCC ATCTGCTTAC AATTCCCTGC TGTCGTCTTA
2300
GCAAGAAGTA AAATGAGAAA TTTTGTTGAA AAAAAAAAA AAAAAAAAA AAAAAAAA

FIG. 2D

```
                                            Mature ∝-Amylase
     ∝-Amlase Signal Sequence    ┌─────────────────────────────────
1) ──────────────────────────── AlaLeuAlaAlaThrProAlaAspTrpArgSerGlnSer Mature Human Lactoferrin
     Lactoferrin Signal Sequence  ┌─────────────────────────────────
2) ──────────────────────────── CysLeuAlaGlyArgArgArgArgSerValGlnTrpCys Mature Recombinant Lactoferrin
     ∝-Amylase Signal Sequence    ┌─────────────────────────────────
3) ──────────────────────────── AlaLeuAlaAlaGlyArgArgArgArgSerValGlnTrp
```

FIG. 8C

```
   1  NNNNGAGCCT TCGTTCCGGA GTCGCCCCAG GACGCCAGCC CATGAAGCTC
  51  TTCGTCCCCG CCCTCCTGTC CCTTGGAGCC CTTGGACTGT GTCTGGCTGC
 101  CCCGAGGAAA AACGTTCGAT GGTGTACCAT CTCCCAACCT GAGTGGTTCA
 151  AATGCCGCAG ATGGCAGTGG AGGATGAAGA AGCTGGGTGC TCCCTCTATC
 201  ACCTGTGTGA GGCGGGCCTT TGCCTTGGAA TGTATTCCGG CATCGCGGA
 251  GAAAAGGCG ATGCTGTGA CCCTGGATGG TGGCATGGTG TTTGAGGCGG
 301  GCCGGGACCC CTACAAACTG CGGCCAGTAG CAGCAGAGAT CTATGGGACG
 351  AAAGAGTCTC CCCAAACCCA CTATTATGCT GTGGCCGTCG TGAAGAAGGG
 401  CAGCAACTTT CAGCTGGACC AGCTGCAAGG CCGGAAGTCC TGCCATACGG
 451  GCCTTGGCAG GTCCGCTGGG TGGATCATCC CTATGGGAAT CCTTCGCCCG
 501  TACTTGAGCT GGACAGAGTC ACTCGAGCCC TCCAGGGAG CTGTGGCTAA
 551  ATTCTTCTCT GCCAGCTGTG TTCCCTGCAT TGATAGACAA CCATACCCCA
 601  ACCTGTGTCA ACTGTGCAAG GGGAGGGGG AGAACCAGTG TGCCTGCTCC
 651  TCCCGGGAAC CATACTTCGG TTATTCTGGT GCCTTCAAGT GTCTGCAGGA
 701  CGGGGCTGGA GACGTGGCTT TTGTTAAAGA GACGACAGTG TTTGAGAACT
 751  TGCCAGAGAA GGCTGACAGG GACCAGTATG AGCTTCTCTG CCTGAACAAC
 801  AGTCGGGCGC CAGTGGATGC GTTCAAGGAG TGCCACCTGG CCCAGGTCCC
 851  TTCTCATGCT GTCGTGGCCC GAAGTGTGGA TGGCAAGGAA GACTTGATCT
 901  GGAAGCTTCT CAGCAAGGCG CAGGAGAAAT CTGGAAAAAA CAAGTCTCGG
 951  AGCTTCCAGC TCTTTGGCTC TCCACCCGGC CAGAGGGACC TGCTGTTCAA
1001  AGACTCTGCT CTTGGGTTTT TGAGGATCCC CTCGAAGGTA GATTCGGCGC
1051  TGTACCTGGG CTCCCGCTAC TTGACCACCT TGAAGAACCT CAGGGAAACT
1101  GCGGAGGAGG TGAAGGCGCG GTACACCAGG GTCGTGTGGT GTGCCGTGGG
1151  ACCTGAGGAG CAGAAGAAGT GCCAGCAGTG GAGCCAGCAG AGCGGCCAGA
1201  ACGTGACCTG TGCCACGGCG TCCACCACTG ACGACTGCAT CGTCCTGGTG
1251  CTGAAAGGGG AAGCAGATGC CCTGAACTTG GATGGAGGAT ATATCTACAC
1301  TGCGGGCAAG TGTGGCCTGG TGCCTGTCCT GGCAGAGAAC CGGAAATCCT
1351  CCAAACACAG TAGCCTAGAT TGTGTGCTGA GACCAACGGA AGGGTACCTT
1401  GCCGTGGCAG TTGTCAAGAA AGCAAATGAG GGGCTCACAT GGAATTCTCT
```

FIG. 14A

```
1451    GAAAGACAAG AAGTCGTGCC ACACCGCCGT GGACAGGACT GCAGGCTGGA
1501    ACATCCCCAT GGGCCTGATC GTCAACCAGA CAGGCTCCTG CGCATTTGAT
1551    GAATTCTTTA GTCAGAGCTG TGCCCCTGGG GCTGACCCGA ATCCAGACT
1601    CTGTGCCTTG TGTGCTGGCG ATGACCAGGG CCTGGACAAG TGTGTGCCCA
1651    ACTCTAAGGA GAAGTACTAT GGCTATACCG GGCTTTCAG GTGCCTGGCT
1701    GAGGACGTTG GGACGTTGC CTTTGTGAAA AACGACACAG TCTGGGAGAA
1751    CACGAATGGA GAGAGCACTG CAGACTGGGC TAAGAACTTG AATCGTGAGG
1801    ACTTCAGGTT GCTCTGCCTC GATGGCACCA GGAAGCCTGT GACGGAGGCT
1851    CAGAGCTGCC ACCTGGCGGT GGCCCCGAAT CACGCTGTGG TGTCTCGGAG
1901    CGATAGGGCA GCACACGTGA ACAGGTGCT GCTCCACCAG CAGGCTCTGT
1951    TTGGGAAAAA TGGAAAAAAC TGCCCGGACA AGTTTTGTTT GTTCAAATCT
2001    GAAACCAAAA ACCTTCTGTT CAATGACAAC ACTGAGTGTC TGGCCAAACT
2051    TGGAGGCAGA CCAACGTATG AAGAATATTT GGGGACAGAG TATGTCACGG
2101    CCATTGCCAA CCTGAAAAAA TGCTCAACCT CCCCGCTTCT GGAAGCCTGC
2151    GCCTTCCTGA CGAGGTAAAG CCTGCAAAGA AGCTAGCCTG CCTCCCTGGG
2201    CCTCAGCTCC TCCCTGCTCT CAGCCCCAAT CTCCAGGCGC GAGGGACCTT
2251    CCTCTCCCTT CCTGAAGTCG ATTTTGCC AAGCTCATCA GTATTTACAA
2301    TTCCCTGCTG TCATTTTAGC AAGAAATAAA ATTAGAAATG CTGTTGAAAA
2351    A
```

FIG. 14B

```
MKLFVPALLSLGALGLCLAAPRKNVRWCTISQPEWFKCRRWQWRMKKLGAPSITCVRRAFAL
ECIPGIAEKKADAVTLDGGMVFEAGRDPYKLRPVAAEIYGTKESPQTHYYAVAVVKKGSNFQ
LDQLQGRKSCHTGLGRSAGWIIPMGILRPYLSWTESLEPLQGAVAKFFSASCVPCIDRQAYP
NLCQLCKGEGENQCACSSREPYFGYSGAFKCLQDGAGDVAFVKETTVFENLPEKADRDQYEL
LCLNNSRAPVDAFKECHLAQVPSHAVVARSVDGKEDLIWKLLSKAQEKSGKNKSRSFQLFGS
PPGQRDLLFKDSALGFLRIPSKVDSALYLGSRYLTTLKNLRETAEEVKARYTRVVWCAVGPE
EQKKCQQWSQQSGQNVTCATASTTDDCIVLVLKGEADALNLDGGYIYTAGKCGLVPVLAENR
KSSKHSSLDCVLRPTEGYLAVAVVKKANEGLTWNSLKDKKSCHTAVDRTAGWNIPMGLIVNQ
TGSCAFDEFFSQSCAPGADPKSRLCALCAGDDQGLDKCVPNSKEKYYGYTGAFRCLAEDVGD
VAFVKNDTVWENTNGESTADWAKNLNREDFRLLCLDGTRKPVTEAQSCHLAVAPNHAVVSRS
DRAAHVKQVLLHQQALFGKNGKNCPDKFCLFKSETKNLLFNDNTECLAKLGGRPTYEEYLGT
EYVTAIANLKKCSTSPLLEACAFLTR
```

FIG. 14C

```
   1  ACATGAAGCT CTTCATCCCC GCCCTGCTGT TCCTCGGGAC ACTTGGACTG
  51  TGTCTGGCTG CCCCTAAGAA AGGGGTTCGA TGGTGTGTCA TATCCACAGC
 101  AGAGTATTCA AAATGCCGCC AGTGGCAATC AAAGATAAGA AGAACTAATC
 151  CCATGTTCTG CATAAGGAGG CTTCTCCCA CTGACTGTAT CCGGGCCATC
 201  GCGGCAAAAA GGGCAGATGC TGTGACCCTT GATGGTGGTT TGGTGTTTGA
 251  AGCAGACCAG TACAAACTGC GGCCGGTAGC AGCGGAGATC TACGGGACAG
 301  AAGAGAATCC CCAAACCTAC TATTATGCTG TGGCTGTAGT GAAGAAAGGT
 331  TTCAACTTTC AGAACCAGCT ACAAGGTCGA AAGTCCTGCC ACACAGGCCT
 401  TGGCAGGTCT GCCGGGTGGA ATATCCCTAT AGGGTTACTT CGCCGGTTCT
 451  TGGACTGGGC AGGGCCACCT GAGCCCCTCC AGAAAGCTGT GGCCAAATTC
 501  TTCTCTCAGA GCTGTGTGCC CTGCGCAGAT GGAAATGCGT ATCCCAACCT
 551  GTGTCAGCTG TGCATAGGGA AAGGGAAAGA TAAATGTGCT TGTTCCTCCC
 601  AGGAACCGTA TTTTGGCTAT TCCGGTGCCT TCAACTGTCT GCACAAAGGG
 651  ATTGGAGATG TGGCTTTTGT CAAGGAGAGT ACAGTGTTTG AGAACCTGCC
 701  ACAGAAGGCT GACCGGGACA AATACGAGCT ACTCTGCCCA GACAATACTC
 751  GAAAGCCAGT GGAAGCATTC AGGGAGTGCC ACCTGCCCG GGTCCCTTCT
 801  CATGCTGTTG TGGCCCGAAG TGTGAATGGC AAGGAGAACT CCATCTGGGA
 851  GCTTCTCTAC CAGTCACAGA AAAGTTTGG AAAAAGCAAT CCACAGGAGT
 901  TCCAGCTCTT TGGCTCTCCT GGTCAGCAGA AGGACCTCCT GTTTAGAGAT
 951  GCTACCATCG GGTTTTTGAA GATCCCCTCA AAGATAGATT CTAAGCTGTA
1001  CCTGGGCCTC CCGTACCTTA CTGCCATCCA GGGCCTGAGG GAAACGGCAG
1051  CGGAGGTGGA GGCGCGGCAG GCGAAGGTCG TGTGGTGCGC CGTGGGTCCA
1101  GAGGAGCTGC GCAAGTGCCG GCAGTGGAGC AGCCAGAGCA GCCAGAACCT
1151  GAACTGCAGC CTGGCCTCCA CCACCGAGGA CTGCATCGTC CAGGTGCTGA
1201  AAGGAGAAGC TGATGCTATG AGCTTGGATG GAGGATTTAT CTACACTGCG
1251  GGCAAGTGTG GTTTGGTGCC TGTCCTGGCA GAGAACCAAA AATCTCGCCA
1301  AAGCAGTAGC TCAGACTGTG TGCATAGACC AACACAAGGG TATTTTGCCG
1351  TGGCGGTTGT CAGGAAAGCA AATGGTGGTA TCACCTGGAA CTCTGTGAGA
1401  GGCACGAAGT CCTGCCACAC TGCTGTGGAC AGGACAGCAG CTGGAACAT
```

FIG. 15A

```
1451  CCCCATGGGC CTGCTTGTCA ACCAGACAGG CTCCTGCAAA TTTGACGAAT
1501  TCTTTAGTCA AAGCTGTGCT CCTGGGTCTC AGCCGGGATC CAATCTCTGT
1551  GCACTGTGTG TTGGCAATGA CCAGGGCGTG ACAAGTGTG TGCCCAACAG
1601  TAATGAGAGA TACTATGGTT ACACCGGGGC TTTCAGGTGC CTGGCTGAGA
1651  ATGCTGGGGA TGTGGCGTTT GTGAAAGATG TCACTGTCTT GGACAACACG
1701  AATGGACAGA ACACAGAAGA GTGGGCCAGG GAATTGAGGT CAGATGACTT
1751  TGAGCTGCTG TGCCTTGATG GCACCAGGAA GCCTGTGACT GAGGCTCAGA
1801  ACTGTCACCT GGCTGTGGCC CCCAGTCATG CTGTGGTCTC TCGGAAGGAA
1851  AAGGCAGCAC AGGTGGAACA GGTGCTACTC ACTGAGCAGG CTCAGTTTGG
1901  AAGATACGGA AAGACTGCC CGGACAAGTT TTGCTTGTTC CGGTCTGAGA
1951  CCAAAAACCT TCTGTTCAAC GACAACACGG AGGTTCTGGC CCAACTCCAA
2001  GGCAAAACAA CATACGAAAA ATATTTGGGA TCAGAGTATG TCACAGCCAT
2051  CGCTAACCTG AAACAGTGCT CAGTCTCCCC GCTTCTGGAA GCCTGTGCCT
2101  TCATGATGAG GTAAAACCGG AAAGAAGCT GCCCGCCTCC CCAGGGGCCT
2151  CAGCTTTCCC TCCTCCCGTC TTGATTCCCA GCTGCCCTGG GCCTGCCTCT
2201  CTCCCTTCCT GAGGGCAGAC TTTGTTCAGC TCATCCGTTT TCACAATTCC
2251  CTCGTGCCG
```

FIG. 15B (Linear) MAPSORT of: hlf2 check: 7473 from: 1 to: 2360
Mismatch: 0 MinCuts = 1 MaxCuts: 10

AccI GT'mk_AC
Cuts at:      0    319   2360
  Size:         319   2041
AceIII CAGCTCnnnnnnn'nnnn_
Cuts at:      0    948   1125   2183   2219   2360
  Size:         948   177   1058   36    141
  Fragments arranged by size:
              1058   948   177   141   36
AhdI GACnn_n'nnGTC
Cuts at:      0    472   2360
  Size:         472   1888
AlwI GGATCnnnn'n_
Cuts at:      0    1341   1955   2360
  Size:         1341   614   405
  Fragments arranged by size:
              1341   614   405
AlwNI CAG_nnn'CTG
Cuts at:      0    1139   1913   2360
  Size:         1139   774   447
  Fragments arranged by size:
              1139   774   447
ApaI G_GGCC'C
Cuts at:      0    56   2360
  Size:         56    2304
ApaBI GCA_nnnnn'TGC
Cuts at:      0    1140   1789   2360
  Size:         1140   649   571
  Fragments arranged by size:
              1140   649   571
ApaLI G'TGCA_C
Cuts at:      0    101   2360
  Size:         101   2259
ApoI r'AATT_y
Cuts at:      0    1    930   1527   1932   2136   2318   2360
  Size:         1    929   597   405   204   182   42
  Fragments arranged by size:
              929   597   405   204   182   42   1

FIG. 18A

AvaI C'yCGr_G
Cuts at:     0     48    117    820   1010   1571   2360
  Size:        48    69    703    190    561    789
  Fragments arranged by size:
               789   703   561   190    69     48
AvaII G'GwC_C
Cuts at:     0    325    439    495    725    824   2067   2360
  Size:       325   114    56    230    99   1243   293
  Fragments arranged by size:
              1243   325   293   230   114    99     56
BanI G'GyrC_C
Cuts at:     0    657   1004   1298   1675   2360
  Size:       657   347   294    377    685
  Fragments arranged by size:
               685   657   377   347   294
BanII G_rGCy'C
Cuts at:     0     56    508   1521   2360
  Size:        56   452   1013    839
  Fragments arranged by size:
              1013   839   452    56
BbsI GAAGACnn'nnnn_
Cuts at:     0     20   2360
  Size:        20   2340
BbvI GCAGCnnnnnnnn'nnnn_
Cuts at:     0    168    394    528   1079   1126   1189   1780   1827
  Size:       168   226   134    551    47     63    591     47
Cuts at:   1827   1900   2360
  Size:        73   460
  Fragments arranged by size:
               591   551   460   226   168   134    73     63    47    47
Bce83I CTTGAGnnnnnnnnnnnnnnn_nn'
Cuts at:     0   1088   1187   2360
  Size:      1088    99   1173
  Fragments arranged by size:
              1173  1088    99
BcefI ACGGCnnnnnnnnnnnn'n_
Cuts at:     0     62    343    823   1447   1670   1855   2360
  Size:        62   281   480    624    223    185    505
  Fragments arranged by size:
               624   505   480   281   223   185    62

FIG. 18B

BfaI C'TA_G
Cuts at:     0    952   1414   1834   2360
   Size:       952    462    420    526
   Fragments arranged by size:
               952    526    462    420
BfiI ACTGGG
Cuts at:     0   1664   2360
   Size:      1664    696
BglI GCCn_nnn'nGGC
Cuts at:     0    427    843   1807   2360
   Size:       427    416    964    553
   Fragments arranged by size:
               964    553    427    416
BglII A'GATC_T
Cuts at:     0    965   1575   2360
   Size:       965    610    785
   Fragments arranged by size:
               965    785    610
BmgI GkGCCC
Cuts at:     0     54   1007   1557   1631   2360
   Size:        54    953    550     74    729
   Fragments arranged by size:
               953    729    550     74     54
BpmI CTGGAGnnnnnnnnnnnnnnnn_nn'
Cuts at:     0    706   1714   2360
   Size:       706   1008    646
   Fragments arranged by size:
              1008    706    646
Bpu10I CC'TnA_GC
Cuts at:     0    502   1765   2188   2360
   Size:       502   1263    423    172
   Fragments arranged by size:
              1263    502    423    172
BsaWI w'CCGG_w
Cuts at:     0   1672   2360
   Size:      1672    688
BsaXI ACnnnnnCTCC
Cuts at:     0    ·87   1037   1268   2360
   Size:        87    950    231   1092
   Fragments arranged by size:
              1092    950    231     87

FIG. 18C

BsbI CAACAC
Cuts at:   0   778   2014   2227   2360
  Size:    778   1236   213   133
  Fragments arranged by size:
           1236   778   213   133
BscGI CCCGT
Cuts at:   0   324   494   681   1517   2360
  Size:    324   170   187   836   843
  Fragments arranged by size:
           843   836   324   187   170
BseRI GAGGAGnnnnnnnnn_nn'
Cuts at:   0   617   1095   1181   2360
  Size:    617   478   86   1179
  Fragments arranged by size:
           1179   617   478   86
BsgI GTGCAGnnnnnnnnnnnnnnnn_nn'
Cuts at:   0   577   2360
  Size:    577   1783
BsiEI CG_ry'CG
Cuts at:   0   10   2360
  Size:    10   2350
BsiHKAI G wGCw'C
Cuts at:   0   105   714   1592   2109   2360
  Size:    105   609   878   517   251
  Fragments arranged by size:
           878   609   517   251   105
BsmI GAATG_Cn'
Cuts at:   0   1694   2360
  Size:    1694   666
BsmAI GTCTCn'nnnn_
Cuts at:   0   187   670   682   1690   1882   2360
  Size:    187   483   12   1008   192   478
  Fragments arranged by size:
           1008   483   478   192   187   12
BsmBI CGTCTCn'nnnn_
Cuts at:   0   670   682   1690   2360
  Size:    670   12   1008   670
  Fragments arranged by size:
           1008   670   670   12
BsmFI GGGACnnnnnnnnnn'nnnn_
Cuts at:   0   338   479   614   762   810   2080   2360
  Size:    338   141   135   148   48   1270   280
  Fragments arranged by size:
           1270   338   280   148   141   135   48

FIG. 18D

```
Bsp24I GACnnnnnnTGGnnnnnnn_nnnnn'
Cuts at:    0    52    84    239    271    569    601    2062    2094
   Size:       52    32    155    32    298    32    1461    32
Cuts at:  2094   2360
   Size:       266
   Fragments arranged by size:
            1461   298   266   155    52    32    32    32    32
Bsp1286I G_dGCh'C
Cuts at:    0    56    105    508    714    1009    1521    1559    1592
   Size:       56    49    403    206    295    512    38    33
Cuts at:  1592   1633   2109   2360
   Size:       41    476    251
   Fragments arranged by size:
            512   476   403   295   251   206    56    49    41    38    33
BspMI ACCTGCnnnn'nnnn_
Cuts at:    0   1194   2360
   Size:     1194   1166
BsrI ACTG_Gn'
Cuts at:    0    206    789   1154   1667   1979   2360
   Size:       206    583    365    513    312    381
   Fragments arranged by size:
            583    513    381    365    312    206
BsrDI GCAATG_nn'
Cuts at:    0    220   1646   2360
   Size:       220   1426    714
   Fragments arranged by size:
           1426    714    220
BsrGI T'GTAC_A
Cuts at:    0   1273   2360
   Size:     1273   1087
BstXI CCAn_nnnn'nTGG
Cuts at:    0    942   1161   1256   2360
   Size:       942    219    95   1104
   Fragments arranged by size:
           1104    942    219    95
BstYI r'GATC_y
Cuts at:    0    965   1575   1947   2360
   Size:       965    610    372    413
   Fragments arranged by size:
            965    610    413    372
```

FIG. 18E

Bsu36I CC'TnA_GG
Cuts at:      0    2142    2360
   Size:    2142     218
CjeI ACnnnnnnTGGnnnnnnn'nnnnnn_
Cuts at:      0      79     188    266     563     618    2056  2360
   Size:     79     109      78    297      55    1438     304
   Fragments arranged by size:
           1438     304     297    109      79      78      55
CviRI TG'CA
Cuts at:      0     103     184    404     558    1216    1281  1476   1525
   Size:    103      81     220    154     658      65     195    49
Cuts at:   1525    1704    1730   2360
   Size:    179      26     630
   Fragments arranged by size:
            658     630     220    195     179     154     103    81
             65      49      26
DdeI C'TnA_G
Cuts at:      0     502     536    672    1684    1765    1828  2017   2142
   Size:    502      34     136   1012      81      63     189   125
Cuts at:   2142    2188    2297   2360
   Size:     46     109      63
   Fragments arranged by size:
           1012     502     189    136     125     109      81    63     63    46    34
DpnI GA'TC
Cuts at:      0     967    1348   1406    1577    1949    2360
   Size:    967     381      58    171     372     411
   Fragments arranged by size:
            967     411     381    372     171      58
DraIII CAC_nnn'GTG
Cuts at:      0     852    2020   2360
   Size:    852    1168     340
   Fragments arranged by size:
           1168     852     340
DsaI C'CryG_G
Cuts at:      0     358    1462   1492    1852    1870    2036  2360
   Size:    358    1104      30    360      18     166     324
   Fragments arranged by size:
           1104     360     358    324     166      30      18
EaeI y'GGCC_r
Cuts at:      0      74     523   2026    2360
   Size:     74     449    1503    334
   Fragments arranged by size:
           1503     449     334     74

FIG. 18F

EarI CTCTTCn'nnn
Cuts at:    0    152    1509    2216    2360
  Size:      152   1357    707    144
  Fragments arranged by size:
             1357    707    152    144
EciI TCCGCC
Cuts at:    0    313    891    2360
  Size:      313    578    1469
  Fragments arranged by size:
             1469    578    313
Eco57I CTGAAGnnnnnnnnnnnnnnnn_nn'
Cuts at:    0    432    629    2269    2360
  Size:      432    197    1640    91
  Fragments arranged by size:
             1640    432    197    91
EcoNI CCTnn'n_nnAGG
Cuts at:    0    1372    1905    2248    2360
  Size:      1372    533    343    112
  Fragments arranged by size:
             1372    533    343    112
EcoO109I rG'GnC_Cy
Cuts at:    0    52    53    725    824    2231    2360
  Size:      52    1    672    99    1407    129
  Fragments arranged by size:
             1407    672    129    99    52    1
EcoRI G'AATT_C
Cuts at:    0    1    2136    2360
  Size:      1    2135    224
  Fragments arranged by size:
             2135    224    1
EcoRV GAT'ATC
Cuts at:    0    1380    2360
  Size:      1380    980
FauI CCCGCnnnn'nn_
Cuts at:    0    590    1099    2360
  Size:      590    509    1261
  Fragments arranged by size:
             1261    590    509
FokI GGATGnnnnnnnnn'nnnn_
Cuts at:    0    189    460    882    1044    1272    1895    2252    2360
  Size:      189    271    422    162    228    623    357    108
  Fragments arranged by size:
             623    422    357    271    228    189    162    108

FIG. 18G

FspI TGC'GCA
Cuts at:    0    1143    2360
  Size:    1143    1217
GdiII y'GGCC_G
Cuts at:    0    74    2360
  Size:    74    2286
HaeI wGG'CCw
Cuts at:    0    123    219    280    430    525    2028    2360
  Size:    123    96    61    150    95    1503    332
  Fragments arranged by size:
        1503    332    150    123    96    95    61
HgiEII ACCnnnnnnGGT
Cuts at:    0    254    2360
  Size:    254    2106
HhaI G_CG'C
Cuts at:    0    1106    1144    1793    2360
  Size:    1106    38    649    567
  Fragments arranged by size:
        1106    649    567    38
Hin4I GAbnnnnnvTC
Cuts at:    0    471    727    1573    1578    1580    2263    2360
  Size:    471    256    846    5    2    683    97
  Fragments arranged by size:
        846    683    471    256    97    5    2
HinfI G'AnT_C
Cuts at:    0    195    881    981    1020    1862    2032    2360
  Size:    195    686    100    39    842    170    328
  Fragments arranged by size:
        842    686    328    195    170    100    39
HphI GGTGAnnnnnnn_n'
Cuts at:    0    380    916    1626    2360
  Size:    380    536    710    734
  Fragments arranged by size:
        734    710    536    380
MaeII A'CG_T
Cuts at:    0    691    1699    2360
  Size:    691    1008    661
  Fragments arranged by size:
        1008    691    661

FIG. 18H

MaeIII 'GTnAC_
Cuts at:   0    245    760    922    1149    1181    1338    1718    1823
  Size:       245    515    162    227     32     157    380    105
Cuts at:  1823   2360
  Size:       537
  Fragments arranged by size:
              537    515    380    245    227    162    157    105    32
MboII GAAGAnnnnnnn_n'
Cuts at:   0    20    169    383    524    876    1496    2170    2173
  Size:       20    149    214    141    352    620    674     3
Cuts at:  2173   2203   2360
  Size:       30    157
  Fragments arranged by size:
              674    620    352    214    157    149    141    30    20    3
MmeI TCCrACnnnnnnnnnnnnnnnnnnnn_nn'
Cuts at:   0    30    2360
  Size:       30    2330
MscI TGG'CCA
Cuts at:   0    525    2028    2360
  Size:       525    1503    332
  Fragments arranged by size:
              1503    525    332
MslI CAynn'nnrTG
Cuts at:   0    352    1461    2360
  Size:       352    1109    899
  Fragments arranged by size:
              1109    899    352
MspI C'CG_G
Cuts at:   0    553    821    1042    1097    1673    1959    2360
  Size:       553    268    221    55    576    286    401
  Fragments arranged by size:
              576    553    401    286    268    221    55
MspA1I CmG'CkG
Cuts at:   0    181    392    444    519    544    2360
  Size:       181    211    52    75    25    1816
  Fragments arranged by size:
              1816    211    181    75    52    25
NciI CC's_GG
Cuts at:   0    553    821    822    1097    1959    2360
  Size:       553    268    1    275    862    401
  Fragments arranged by size:
              862    553    401    275    268    1

FIG. 18I

NcoI C'CATG_G
Cuts at:   0   1492   1852   2036   2360
  Size:   1492    360    184    324
  Fragments arranged by size:
          1492    360    324    184
NdeI CA'TA_TG
Cuts at:   0   2051   2360
  Size:   2051    309
NlaIII _CATG'
Cuts at:   0    20    837   1253   1496   1762   1856   1869   2040
  Size:    20   817    416    243    266    94     13    171
Cuts at: 2040   2360
  Size:    320
  Fragments arranged by size:
          817    416    320    266    243    171     94     20          13
PleI GAGTCnnnn'n_
Cuts at:   0   189    975   2026   2360
  Size:   189   786   1051    334
  Fragments arranged by size:
         1051   786    334    189
Psp5II rG'GwC_Cy
Cuts at:   0   725    824   2360
  Size:   725    99   1536
  Fragments arranged by size:
         1536   725     99
PstI C_TGCA'G
Cuts at:   0   1283   1478   2360
  Size:   1283   195    882
  Fragments arranged by size:
         1283   882    195
PvuII CAG'CTG
Cuts at:   0   181    392    519    544   2360
  Size:   181   211    127     25   1816
  Fragments arranged by size:
         1816   211    181    127     25
RsaI GT'AC
Cuts at:   0   642   1032   1275   2360
  Size:   642   390    243   1085
  Fragments arranged by size:
         1085   642    390    243

FIG. 18J

SanDI GG'GwC_CC
Cuts at:    0    824    2360
  Size:       824    1536
SapI GCTCTTCn'nnn_
Cuts at:    0    1509    2216    2360
  Size:       1509    707    144
  Fragments arranged by size:
              1509    707    144
Sau3AI 'GATC_
Cuts at:    0    965    1346    1404    1575    1947    2360
  Size:       965    381    58    171    372    413
  Fragments arranged by size:
              965    413    381    372    171    58
SfaNI GCATCnnnnn'nnnn_
Cuts at:    0    230    860    1225    1235    2360
  Size:       230    630    365    10    1125
  Fragments arranged by size:
              1125    630    365    230    10
SfcI C'TryA_G
Cuts at:    0    304    460    1279    1474    2360
  Size:       304    156    819    195    886
  Fragments arranged by size:
              886    819    304    195    156
SmaI CCC'GGG
Cuts at:    0    822    2360
  Size:       822    1538
Sse8647I AG'GwC_CT
Cuts at:    0    725    2360
  Size:       725    1635
SspI AAT'ATT
Cuts at:    0    1539    2061    2360
  Size:       1539    522    299
  Fragments arranged by size:
              1539    522    299
StuI AGG'CCT
Cuts at:    0    280    430    2360
  Size:       280    150    1930
  Fragments arranged by size:
              1930    280    150
StyI C'CwwG_G
Cuts at:    0    1034    1492    1852    2036    2234    2360
  Size:       1034    458    360    184    198    126
  Fragments arranged by size:
              1034    458    360    198    184    126

FIG. 18K

TaqI T'CG_A
Cuts at:     0    999   1804   2360
  Size:       999    805    556
  Fragments arranged by size:
              999    805    556
TaqII GACCGAnnnnnnnnnn_nn'
Cuts at:     0    342   2360
  Size:       342   2018
TauI GCsGC
Cuts at:     0    310    380   2360
  Size:       310     70   1980
  Fragments arranged by size:
             1980    310     70
TfiI G'AwT_C
Cuts at:     0    881   1020   1862   2360
  Size:       881    139    842    498
  Fragments arranged by size:
              881    842    498    139
ThaI CG'CG
Cuts at:     0   1106   2360
  Size:      1106   1254
TseI GCwGC
Cuts at:     0    182    383    517   1093   1140   1178   1794   1841
  Size:       182    201    134    576     47     38    616     47
Cuts at:   1841   1914   2360
  Size:        73    446
  Fragments arranged by size:
              616    576    446    201    182    134     73     47     38
Tsp45I 'GTsAC_
Cuts at:     0    245    922   1181   1338   1718   1823   2360
  Size:       245    677    259    157    380    105    537
  Fragments arranged by size:
              677    537    380    259    245    157    105
Tsp509I 'AATT_
Cuts at:     0      1    485    930   1527   1932   2136   2280   2318
  Size:         1    484    445    597    405    204    144     38
Cuts at:   2318   2360
  Size:        42.
  Fragments arranged by size:
              597    484    445    405    204    144     42     38

FIG. 18L

Tth111I GACn'n_nGTC
Cuts at:      0    64    2360
   Size:        64    2296
Tth111II CAArCAnnnnnnnnnn_nn'
Cuts at:      0    708    2360
   Size:       708    1652
UbaCI wGTACw
Cuts at:      0    1275    2360
   Size:      1275    1085
XcmI CCAnnnn_n'nnnnTGG
Cuts at:      0    484    2360
   Size:       484    1876

Enzymes that do cut and were not excluded:

| AccI | AceIII | AhdI | AlwI | AlwNI |
|---|---|---|---|---|
| ApaI | ApaBI | ApaLI | ApoI | AvaI |
| AvaII | BanI | BanII | BbsI | BbvI |
| Bce83I | BcefI | BfaI | BfiI | BglI |
| BglII | BmgI | BpmI | Bpu10I | BsaWI |
| BsaXI | BsbI | BscGI | BseRI | BsgI |
| BsiEI | BsiHKAI | BsmI | BsmAI | BsmBI |
| BsmFI | Bsp24I | Bsp1286I | BspMI | BsrI |
| BsrDI | BsrGI | BstXI | BstYI | Bsu36I |
| CjeI | CviRI | DdeI | DpnI | DraIII |
| DsaI | EaeI | EarI | EciI | Eco57I |
| EcoNI | EcoO109I | EcoRI | EcoRV | FauI |
| FokI | FspI | GdiII | HaeI | HgiEII |
| HhaI | Hin4I | HinfI | HphI | MaeII |
| MaeIII | MboII | MmeI | MscI | MsII |
| MspI | MspA1I | NciI | NcoI | NdeI |
| NlaIII | PleI | Psp5II | PstI | PvuII |
| RsaI | SanDI | SapI | Sau3AI | SfaNI |
| SfcI | SmaI | Sse8647I | SspI | StuI |
| StyI | TaqI | TaqII | TauI | TfiI |
| ThaI | TseI | Tsp45I | Tsp509I | Tth111I |
| Tth111II | UbaCIXcmI | | | |

Enzymes that do not cut:

| AatII | AflII | AflIII | AscI | AvrII |
|---|---|---|---|---|
| BaeI | BamHI | BcgI | BcgI | BclI |
| BplI | Bpu1102I | BsaI | BsaAI | BsaBI |
| BsaHI | BspEI | BspGI | BspLU11I | BsrBI |
| BsrFI | BssHII | BssSI | Bst1107I | BstEII |
| ClaI | DraI | DrdI | DrdII | EagI |
| Eco47III | FseI | HaeII | HgaI | HincII |

FIG. 18M

| | | | | |
|---|---|---|---|---|
| HindIII | HpaI | KpnI | MluI | MseI |
| MunI | NarI | NgoAIV | NheI | NotI |
| NruI | NsiI | NspI | NspV | PacI |
| Pfl1108I | PflMI | PinAI | PmeI | PmlI |
| PshAI | Psp1406I | PvuI | RcaI | RleAI |
| RsrII | SacI | SacII | SalI | ScaI |
| SexAI | SfiI | SgfI | SgrAI | SnaBI |
| SpeI | SphI | SrfI | Sse8387I | SunI |
| SwaI | VspI | XbaI | XhoI | XmnI |

Enzymes excluded; MinCuts: 1  MaxCuts: 10

| | | | | |
|---|---|---|---|---|
| AciI | AluI | BccI | BsaJI | BslI |
| BsoFI | Cac8I | CjeI | CjePI | CjePI |
| CviJI | EcoRII | HaeIII | MnlI | MwoI |
| NlaIV | Sau96I | ScrFI | TspRI | |

FIG. 18N (Linear)MAPSORT of: piglac.gb_om check: 9514 from:1 to :2259
LOCUS    PIGLAC    2259 bp ss-mRNA    MAM
DEFINITION  Sus scrofa lactoferrin mRNA, complete cds.
ACCESSION   M81327 M61828
KEYWORDS    lactoferrin.
SOURCE    Sus scrofa lactational mammary gland cDNA to mRNA.
  ORGANISM  Sus scrofa . . .
 Mismatch: 0  MinCuts = 1  MaxCuts: 10
 With 209 enzymes: *

AceIII CAGCTCnnnnnnn'nnnn_
Cuts at:    0    497    915    1092    1740    2239    2259
  Size:        497    418    177    648    499    20
  Fragments arranged by size:
            648    499    497    418    177    20
AlwI GGATCnnnn'n_
Cuts at:    0    965    1531    1544    2036    2259
  Size:        965    566    13    492    223
  Fragments arranged by size:
            965    566    492    223    13
AlwNI CAG_nnn'CTG
Cuts at:    0    219    1034    1148    1196    2259
  Size:        219    815    114    48    1063
  Fragments arranged by size:
            1063    815    219    114    48
ApaLI G'TGCA_C
Cuts at:    0    1549    2259
  Size:        1549    710
ApoI r'AATT_y
Cuts at:    0    495    1488    1497    2259
  Size:        495    993    9    762
  Fragments arranged by size:
            993    762    495    9
AvaI C'yCGr_G
Cuts at:    0    33    787    2259
  Size:        33    754    1472
  Fragments arranged by size:
            1472    754    33
AvaII G'GwC_C
Cuts at:    0    791    932    1095    2259
  Size:        791    141    163    1164
  Fragments arranged by size:
            1164    791    163    141

FIG. 19A

BaeI ACnnnnGTAyC
Cuts at:   0   1614   2259
  Size:   1614   645

BamHI G'GATC_C
Cuts at:   0   1536   2259
  Size:   1536   723

BanI G'GyrC_C
Cuts at:   0   624   1265   1636   1770   2259
  Size:    624   641   371   134   489
  Fragments arranged by size:
           641   624   489   371   134

BanII G_rGCy'C
Cuts at:   0   475   2259
  Size:    475   1784

BccI CCATC
Cuts at:   0   81   197   233   530   842   956   1025   1229
  Size:    81   116   36   297   312   114   69   204
Cuts at:   1229   1769   2048   2259
  Size:    540   279   211
  Fragments arranged by size:
           540   312   297   279   211   204   116   114   81   69   36

BcefI ACGGCnnnnnnnnnnnn'n_
Cuts at:   0   1060   1075   1333   2259
  Size:    1060   15   258   926
  Fragments arranged by size:
           1060   926   258   15

BcgI CGAnnnnnnTGCnnnnnnnnnnn_nn'
Cuts at:   0   367   401   2259
  Size:    367   34   1858
  Fragments arranged by size:
           1858   367   34

BfiI ACTGGG
Cuts at:   0   456   1823   2259
  Size:    456   1367   436
  Fragments arranged by size:
           1367   456   436

BglI GCCn_nnn'nGGC
Cuts at:   0   201   394   1768   2259
  Size:    201   193   1374   491
  Fragments arranged by size:
           1374   491   201   193

FIG. 19B

BglII A'GATC_T
Cuts at:    0    286    2259
  Size:    286    1973
BmgI GkGCCC
Cuts at:    0    518    1592    2259
  Size:    518    1074    667
  Fragments arranged by size:
          1074    667    518

BpII GAGnnnnnCTC
Cuts at:    0    171    2259
  Size:    171    2088
BpmI CTGGAGnnnnnnnnnnnnnnnn_nn'
Cuts at:    0    462    2259
  Size:    462    1797
Bpu10I CC'TnA_GC
Cuts at:    0    469    2149    2259
  Size:    469    1680    110
  Fragments arranged by size:
          1680    469    110
BsaI GGTCTCn'nnnn_
Cuts at:    0    1531    1841    1941    2259
  Size:    1531    310    100    318
  Fragments arranged by size:
          1531    318    310    100
BsaWI w'CCGG_w
Cuts at:    0    621    1939    2116    2259
  Size:    621    1318    177    143
  Fragments arranged by size:
          1318    621    177    143
BsbI CAACAC
Cuts at:    0    1332    1560    1696    1975    2259
  Size:    1332    228    136    279    284
  Fragments arranged by size:
          1332    284    279    228    136
BscGI CCCGT
Cuts at:    0    294    1011    2166    2259
  Size:    294    717    1155    93
  Fragments arranged by size:
          1155    717    294    93
BseRI GAGGAGnnnnnnnnn_nn'
Cuts at:    0    1116    2151    2259
  Size:    1116    1035    108
  Fragments arranged by size:
          1116    1035    108

FIG. 19C

BsgI GTGCAGnnnnnnnnnnnnnnnn_nn'
Cuts at:   0   624   2259
   Size:    624   1635
BsiEI CG_ry'CG
Cuts at:   0   273   2259
   Size:    273   1986
BsiHKAI G_wGCw'C
Cuts at:   0   1520   1553   2070   2259
   Size:    1520   33   517   189
   Fragments arranged by size:
        1520   517   189   33

BslI CCnn_nnn'nnGG
Cuts at:   0   69   449   612   788   1335   1577   1814   2084
   Size:    69   380   163   176   547   242   237   270
Cuts at:  2084   2142   2210   2259
   Size:    58   68   49
   Fragments arranged by size:
        547   380   270   242   237   176   163   69   68   58   49
BsmI GAATG_Cn'
Cuts at:   0   765   1655   2259
   Size:    765   890   604
   Fragments arranged by size:
        890   765   604
BsmAI GTCTCn'nnnn_
Cuts at:   0   1531   1841   1941   2078   2259
   Size:    1531   310   100   137   181
   Fragments arranged by size:
        1531   310   181   137   100
BsmFI GGGACnnnnnnnnnn'nnnn_
Cuts at:   0   50   308   729   777   2259
   Size:    50   258   421   48   1482
   Fragments arranged by size:
        1482   421   258   50   48
Bsp24I GACnnnnnnTGGnnnnnnn_nnnnn'
Cuts at:   0   37   69   215   247   536   568   2259
   Size:    37   32   146   32   289   32   1691
   Fragments arranged by size:
        1691   289   146   37   32   32   32
Bsp1286I G_dGCh'C
Cuts at:   0   475   520   1520   1553   1594   2070   2259
   Size:    475   45   1000   33   41   476   189
   Fragments arranged by size:
        1000   476   475   189   45   41   33

FIG. 19D

BspGI CTGGAC
Cuts at:    0    1098    1190    2259
  Size:     1098    92    1069
  Fragments arranged by size:
            1098    1069    92
BspMI ACCTGCnnnn'nnnn_
Cuts at:    0    394    703    2259
  Size:     394    309    1556
  Fragments arranged by size:
            1556    394    309
BsrI ACTG_Gn'
Cuts at:    0    119    257    459    756    860    1822    2259
  Size:     119    138    202    297    104    962    437
  Fragments arranged by size:
            962    437    297    202    138    119    104
BsrDI GCAATG_nn'
Cuts at:    0    1571    2259
  Size:     1571    688
BsrFI r'CCGG_y
Cuts at:    0    272    442    1117    2259
  Size:     272    170    675    1142
  Fragments arranged by size:
            1142    675    272    170
BssSI C'TCGT_G
Cuts at:    0    2251    2259
  Size:     2251    8
BstXI CCAn_nnnn'nTGG
Cuts at:    0    909    2259
  Size:     909    1350
BstYI r'GATC_y
Cuts at:    0    286    970    1536    2259
  Size:     286    684    566    723
  Fragments arranged by size:
            723    684    566    286
Bsu36I CC'TnA_GG
Cuts at:    0    1035    2209    2259
  Size:     1035    1174    50
  Fragments arranged by size:
            1174    1035    50
Cac8I GCn'nGC
Cuts at:    0    1069    1119    1250    1439    1461    1888    2133    2193
  Size:     1069    50    131    189    22    427    245    60
Cuts at: 2193    2259
  Size:     66
  Fragments arranged by size:
            1069    427    245    189    131    66    60    50    22

FIG. 19E

```
CjeI ACnnnnnnTGGnnnnnnn'nnnnnn
Cuts at:    0    64   164   242   410   530   585   855  1526
  Size:        64   100    78   168   120    55   270   671
Cuts at: 1526  2259
  Size:        733
  Fragments arranged by size:
              733   671   270   168   120   100    78    64    55
CviRI TG'CA
Cuts at:    0   160   562   641  1156  1183  1322  1486  1551
  Size:       160   402    79   515    27   139   164    65
Cuts at: 1551  2259
  Size:        708
  Fragments arranged by size:
              708   515   402   164   160   139    79    65    27
DpnI GA'TC
Cuts at:    0   288   972  1538  2030  2259
  Size:       288   684   566   492   229
  Fragments arranged by size:
              684   566   492   288   229
DraIII CAC_nnn'GTG
Cuts at:    0  1557  2259
  Size:      1557   702
DrdI GACnn_nn'nnGTC
Cuts at:    0  1185  2259
  Size:      1185  1074
DrdII GAACCA
Cuts at:    0   364  1285  2259
  Size:       364   921   974
  Fragments arranged by size:
              974   921   364
DsaI C'CryG_G
Cuts at:    0  1090  1348  1453  2259
  Size:      1090   258   105   806
  Fragments arranged by size:
             1090   806   258   105
EaeI y'GGCC_r
Cuts at:    0   270   490  2259
  Size:       270   220  1769
  Fragments arranged by size:
             1769   270   220
```

FIG. 19F

EagI C'GGCC_G
Cuts at:   0   270   2259
  Size:    270   1989
EarI CTCTTCn'nnn_
Cuts at:   0   15   295   1711   2259
  Size:    15   280   1416   548
  Fragments arranged by size:
           1416   548   280   15
EcoNI CCTnn'n_nnAGG
Cuts at:   0   67   2208   2259
  Size:    67   2141   51
  Fragments arranged by size:
           2141   67   51
EcoO109I rG'GnC_Cy
Cuts at:   0   791   932   1031   2145   2259
  Size:    791   141   99   1114   114
  Fragments arranged by size:
           1114   791   141   114   99
EcoRI G'AATT_C
Cuts at:   0   1497   2259
  Size:    1497   762
FauI CCCGCnnnn'nn_
Cuts at:   0   26   1241   2086   2140   2259
  Size:    26   1215   845   54   119
  Fragments arranged by size:
           1215   845   119   54   26
FokI GGATGnnnnnnnnn'nnnn_
Cuts at:   0   1011   1239   1434   1671   2218   2259
  Size:    1011   228   195   237   547   41
  Fragments arranged by size:
           1011   547   237   228   195   41
FspI TGC'GCA
Cuts at:   0   524   1110   2259
  Size:    524   586   1149
  Fragments arranged by size:
           1149   586   524
GdiII y'GGCC_G
Cuts at:   0   270   2259
  Size:    270   1989
HaeI wGG'CCw
Cuts at:   0   397   492   1164   2259
  Size:    397   95   672   1095
  Fragments arranged by size:
           1095   672   397   95

FIG. 19G

HgiEII ACCnnnnnnGGT
Cuts at:    0    230    2259
  Size:       230    2029
HhaI G_CG'C
Cuts at:    0    525    1064    1089    1111    2259
  Size:       525    539     25      22      1148
  Fragments arranged by size:
              1148    539    525    25    22
Hin4I GAbnnnnnvTC
Cuts at:    0    83    171    1235    1541    1791    2259
  Size:       83    88     1064    306     250     468
  Fragments arranged by size:
              1064    468    306    250    88    83
HincII GTy'rAC
Cuts at:    0    1469    2259
  Size:       1469    790
HinfI G'AnT_C
Cuts at:    0    305    987    2173    2259
  Size:       305    682    1186    86
  Fragments arranged by size:
              1186    682    305    86
HphI GGTGAnnnnnnn_n'
Cuts at:    0    1373    1797    2259
  Size:       1373    424     462
  Fragments arranged by size:
              1373    462    424
MaeIII 'GTnAC_
Cuts at:    0    221    433    862    1617    1679    1784    1803    2039
  Size:       221    212    429    755     62      105     19      236
Cuts at:    2039    2259
  Size:       220
  Fragments arranged by size:
              755    429    236    221    220    212    105    62    19
MboII GAAGAnnnnnnn_n'
Cuts at:    0    2    151    312    353    491    980    1728    1912
  Size:       2    149    161    41     138    489    748    184
Cuts at:    1912    2259
  Size:       347
  Fragments arranged by size:
              748    489    347    184    161    149    138    41
              2

FIG. 19H

MscI TGG'CCA
Cuts at:      0     492    2259
   Size:    492    1767
MslI CAynn'nnrTG
Cuts at:      0    1422    1452    2259
   Size:   1422      30     807
   Fragments arranged by size:
          1422     807      30
MspA1I CmG'CkG
Cuts at:      0     282     557    1050    2181    2259
   Size:    282     275     493    1131      78
   Fragments arranged by size:
          1131     493     282     275      78
MwoI GCnn_nnn'nnGC
Cuts at:      0     201     210     394     470     810    1068    1135    1138
   Size:    201       9     184      76     340     258      67       3
Cuts at:   1138    1650    1768    2259
   Size:    512     118     491
   Fragments arranged by size:
           512     491     340     258     201     184     118      76      67       9       3
NciI CC's_GG
Cuts at:      0     192     413     714     788     789    1534    1625    1920
   Size:    192     221     301      74       1     745      91     295
Cuts at:   1920    2259
   Size:    339
   Fragments arranged by size:
           745     339     301     295     221     192      91      74       1
NcoI C'CATG_G
Cuts at:      0    1453    2259
   Size:   1453     806
NgoAIV G'CCGG_C
Cuts at:      0    1117    2259
   Size:   1117    1142
NlaIII _CATG'
Cuts at:      0       5     155     804    1457    1830    2105    2259
   Size:      5     150     649     653     373     275     154
   Fragments arranged by size:
           653     649     373     275     154     150       5

FIG. 19I

PflMI CCAn_nnn'nTGG
Cuts at:    0   1577   2259
   Size:   1577   682
Psp5II rG'GwC_Cy
Cuts at:    0   791   932   2259
   Size:   791   141   1327
   Fragments arranged by size:
            1327   791   141
PstI C_TGCA'G
Cuts at:    0   1158   2259
   Size:   1158   1101
PvuII CAG'CTG
Cuts at:    0   557   2181   2259
   Size:   557   1624   78
   Fragments arranged by size:
            1624   557   78
RcaI T'CATG_A
Cuts at:    0   2101   2259
   Size:   2101   158
RsaI GT'AC
Cuts at:    0   261   680   999   1014   2259
   Size:   261   419   319   15   1245
   Fragments arranged by size:
            1245   419   319   261   15
SanDI GG'GwC_CC
Cuts at:    0   791   2259
   Size:   791   1468
SapI GCTCTTCn'nnn_
Cuts at:    0   15   2259
   Size:   15   2244
Sau3AI 'GATC_
Cuts at:    0   286   970   1536   2028   2259
   Size:   286   684   566   492   231
   Fragments arranged by size:
            684   566   492   286   231
SfaNI GCATCnnnnn'nnnn_
Cuts at:    0   206   938   1192   1202   2259
   Size:   206   732   254   10   1057
   Fragments arranged by size:
            1057   732   254   206   10
SfcI C'TryA_G
Cuts at:    0   334   427   1154   2259
   Size:   334   93   727   1105
   Fragments arranged by size:
            1105   727   334   93

FIG. 19J

SmaI CCC'GGG
Cuts at:     0      789    2259
   Size:         789    1470
Sse8647I AG'GwC_CT
Cuts at:     0      932    2259
   Size:         932    1327
SspI AAT'ATT
Cuts at:     0     2022    2259
   Size:        2022     237
StuI AGG'CCT
Cuts at:     0      397    2259
   Size:         397    1862
StyI C'CwwG_G
Cuts at:     0      398    1453    1997    2259
   Size:         398    1055     544     262
   Fragments arranged by size:
              1055     544     398     262
TaqI T'CG_A
Cuts at:     0       77     377     749    2259
   Size:          77     300     372    1510
   Fragments arranged by size:
              1510     372     300      77
TauI GCsGC
Cuts at:     0      116     202     270    1065    2259
   Size:         116      86      68     795    1194
   Fragments arranged by size:
              1194     795     116      86      68
TfiI G'AwT_C
Cuts at:     0      305     987    2173    2259
   Size:         305     682    1186      86
   Fragments arranged by size:
              1186     682     305      86
ThaI CG'CG
Cuts at:     0      201    1064    2259
   Size:         201     863    1195
   Fragments arranged by size:
              1195     863     201
Tsp45I 'GTsAC_
Cuts at:     0      221     862    1679    1784    1803    2039    2259
   Size:         221     641     817     105      19     236     220
   Fragments arranged by size:
               817     641     236     221     220     105      19

FIG. 19K

Tsp509I 'AATT_
Cuts at:   0   495   1488   1497   1731   2244   2259
  Size:   495   993   9   234   513   15
  Fragments arranged by size:
          993   513   495   234   15   9
Tth111I GACn'n_nGTC
Cuts at:   0   49   2259
  Size:   49   2210
Tth111II CAArCAnnnnnnnnn_nn'
Cuts at:   0   234   577   675   1452   1922   2259
  Size:   234   343   98   777   470   337
  Fragments arranged by size:
          777   470   343   337   234   98
UbaCI wGTACw
Cuts at:   0   261   680   2259
  Size:   261   419   1579
  Fragments arranged by size:
          1579   419   261
XcmI CCAnnnn_n'nnnnTGG
Cuts at:   0   396   1829   2259
  Size:   396   1433   430
  Fragments arranged by size:
          1433   430   396
XmnI GAAnn'nnTTC
Cuts at:   0   9   348   2259
  Size:   9   339   1911
  Fragments arranged by size:
          1911   339   9

Enzymes that do cut and were not excluded:

| AceIII | AlwI | AlwNI | ApaLI | ApoI | AvaI | AvaII | BaeI |
| BamHI | BanI | BanII | BccI | BcefI | BcgI | BfiI | BglI |
| BglII | BmgI | BplI | BpmI | Bpu10I | BsaI | BsaWI | BsbI |
| BscGI | BseRI | BsgI | BsiEI | BsiHKAI | BslI | BsmI | BsmAI |
| BsmFI | Bsp24I | Bsp1286I | BspGI | BspMI | BsrI | BsrDI | BsrFI |
| BssSI | BstXI | BstYI | Bsu36I | Cac8I | CjeI | CviRI | DpnI |
| DraIII | DrdI | DrdII | DsaI | EaeI | EagI | EarI | EcoNI |
| EcoO109I | EcoRI | FauI | FokI | FspI | GdiII | HaeI | HgiEII |
| HhaI | Hin4I | HincII | HinfI | HphI | MaeIII | MboII | MscI |
| MslI | MspA1I | MwoI | NciI | NcoI | NgoAIV | NlaIII | PflMI |
| Psp5II | PstI | PvuII | RcaI | RsaI | SanDI | SapI | Sau3AI |
| SfaNI | SfcI | SmaI | Sse8647I | SspI | StuI | StyI | TaqI |
| TauI | TfiI | ThaI | Tsp45I | Tsp509I | Tth111I | Tth111II | UbaCI |
| XcmI | XmnI | | | | | | |

FIG. 19L

Enzymes that do not cut:

| | | | | | | | |
|---|---|---|---|---|---|---|---|
| AatII | AccI | AflII | AflIII | AhdI | ApaI | ApaBI | AscI |
| AvrII | BbsI | Bce83I | BclI | BfaI | Bpu1102I | BsaAI | BsaBI |
| BsaHI | BsaXI | BsmBI | BspEI | BspLU11I | BsrBI | BsrGI | BssHII |
| Bst1107I | BstEII | ClaI | DraI | EciI | Eco47III | Eco57I | EcoRV |
| FseI | HaeII | HgaI | HindIII | HpaI | KpnI | MaeII | MluI |
| MmeI | MseI | MunI | NarI | NdeI | NheI | NotI | NruI |
| NsiI | NspI | NspV | PacI | Pfl1108I | PinAI | PleI | PmeI |
| PmlI | PshAI | Psp1406I | PvuI | RleAI | RsrII | SacI | SacII |
| SalI | ScaI | SexAI | SfiI | SgfI | SgrAI | SnaBI | SpeI |
| SphI | SrfI | Sse8387I | SunI | SwaI | TaqII | TaqII | VspI |
| XbaI | XhoI | | | | | | |

Enzymes excluded; MinCuts: 1 MaxCuts: 10

| | | | | | | | |
|---|---|---|---|---|---|---|---|
| AciI | AluI | BbvI | BsaJI | BsoFI | CjeI | CjePI | CjePI |
| CviJI | DdeI | EcoRII | HaeIII | MnlI | MspI | NlaIV | Sau96I |
| ScrFI | TseI | TspRI | | | | | |

FIG. 19M (Linear) MAPSORT of: bovlactof.gb_om  check: 2217  from: 1 to: 2351
LOCUS     BOVLACTOF    2351 bp ss-mRNA         MAM
DEFINITION  Bovine lactoferrin mRNA, complete cds.
ACCESSION   M63502
KEYWORDS    lactoferrin.
SOURCE     B.taurus, cDNA to mRNA.
  ORGANISM  Bos taurus . . .
Mismatch: 0  MinCuts = 1  MaxCuts: 10
With 209 enzymes: *

AceIII CAGCTCnnnnnnn'nnnn_
Cuts at:    0    494    526    969    1553    1841    2216    2351
  Size:       494    32    443    584    288    375    135
  Fragments arranged by size:
              584    494    443    375    288    135    32
AflIII A'CryG_T
Cuts at:    0    1913    2351
  Size:       1913    438
AhdI GACnn_n'nnGTC
Cuts at:    0    1460    2351
  Size:       1460    891
AlwI GGATCnnnn'n_
Cuts at:    0    480    1019    1032    2351
  Size:       480    539    13    1319
  Fragments arranged by size:
              1319    539    480    13
AlwNI CAG_nnn'CTG
Cuts at:    0    1600    1631    1928    1946    2351
  Size:       1600    31    297    18    405
  Fragments arranged by size:
              1600    405    297    31    18
ApoI r'AATT_y
Cuts at:    0    549    1442    1551    2351
  Size:       549    893    109    800
  Fragments arranged by size:
              893    800    549    109
AvaI C'yCGr_G
Cuts at:    0    101    522    652    2351
  Size:       101    421    130    1699
  Fragments arranged by size:
              1699    421    130    101

FIG. 20A

AvaII G'GwC_C
Cuts at:    0    305    416    460    770    845    986    1149    2244
  Size:       305    111     44    310     75    141    163    1095
Cuts at: 2244    2351
  Size:       107
  Fragments arranged by size:
              1095    310    305    163    141    111    107     75     44
BamHI G'GATC_C
Cuts at:    0    1024    2351
  Size:       1024    1327
BanI G'GyrC_C
Cuts at:    0    678    806    1319    1393    1690    1824    2351
  Size:       678    128    513     74    297    134    527
  Fragments arranged by size:
              678    527    513    297    134    128     74
BanII G_rGCy'C
Cuts at:    0    80    529    1062    1435    2351
  Size:       80    449    533    373    916
  Fragments arranged by size:
              916    533    449    373     80
BbsI GAAGACnn'nnnn_
Cuts at:    0    895    2351
  Size:       895    1456
BbvI GCAGCnnnnnnnn'nnnn_
Cuts at:    0    83    342    409    412    1842    1915    1920    2351
  Size:       83    259     67      3    1430     73      5    431
  Fragments arranged by size:
              1430    431    259     83     73     67      5      3
BccI CCATC
Cuts at:    0    120    128    162    278    881    1283    1823    2351
  Size:       120      8     34    116    603    402    540    528
  Fragments arranged by size:
              603    540    528    402    120    116     34      8
Bce83I CTTGAGnnnnnnnnnnnnnn_nn'
Cuts at:    0    524    2351
  Size:       524    1827
BcefI ACGGCnnnnnnnnnnnn'n_
Cuts at:    0    370    1129    1231    1387    1462    2113    2351
  Size:       370    759    102    156     75    651    238
  Fragments arranged by size:
              759    651    370    238    156    102     75
BfaI C'TA_G
Cuts at:    0    1365    2183    2351
  Size:       1365    818    168
  Fragments arranged by size:
              1365    818    168

FIG. 20B

BfiI ACTGGG
Cuts at:   0   1776   2351
  Size:   1776   575
BgII GCCn_nnn'nGGC
Cuts at:   0   448   1578   1822   2351
  Size:   448   1130   244   529
  Fragments arranged by size:
       1130   529   448   244
BglII A'GATC_T
Cuts at:   0   337   2351
  Size:   337   2014
BmgI GkGCCC
Cuts at:   0   1572   1646   2351
  Size:   1572   74   705
  Fragments arranged by size:
       1572   705   74
BpmI CTGGAGnnnnnnnnnnnnnnnn_nn'
Cuts at:   0   516   727   2216   2351
  Size:   516   211   1489   135
  Fragments arranged by size:
       1489   516   211   135
Bpu10I CC'TnA_GC
Cuts at:   0   1699   2202   2351
  Size:   1699   503   149
  Fragments arranged by size:
       1699   503   149
BsaI GGTCTCn'nnnn_
Cuts at:   0   1373   2351
  Size:   1373   978
BsaAI yAC'GTr
Cuts at:   0   1916   2351
  Size:   1916   435
BsaHI Gr'CG_yC
Cuts at:   0   32   807   1218   2351
  Size:   32   775   411   1133
  Fragments arranged by size:
       1133   775   411   32
BsaWI w'CCGG_w
Cuts at:   0   15   1339   2351
  Size:   15   1324   1012
  Fragments arranged by size:
       1324   1012   15
BsaXI ACnnnnnCTCC
Cuts at:   0   634   1058   2351
  Size:   634   424   1293
  Fragments arranged by size:
       1293   634   424

FIG. 20C

BsbI CAACAC
Cuts at:   0    2029   2351
  Size:    2029   322
BscGI CCCGT
Cuts at:   0    449   498   702   2351
  Size:    449   49    204   1649
  Fragments arranged by size:
           1649   449   204   49
BseRI GAGGAGnnnnnnnnn_nn'
Cuts at:   0    638   1119   1170   2198   2351
  Size:    638   481   51    1028   153
  Fragments arranged by size:
           1028   638   481   153   51
BsiHKAI G_wGCw'C
Cuts at:   0    191   1767   2351
  Size:    191   1576   584
  Fragments arranged by size:
           1576   584   191
BsmAI GTCTCn'nnnn_
Cuts at:   0    361   703   723   949   1373   1897   2351
  Size:    361   342   20    226   424   524    454
  Fragments arranged by size:
           524   454   424   361   342   226   20
BsmBI CGTCTCn'nnnn_
Cuts at:   0    703   723   2351
  Size:    703   20    1628
  Fragments arranged by size:
           1628   703   20
BsoFI GC'n_GC
Cuts at:   0    97    155   321   331   401   423   1193   1856
  Size:    97    58    166   10    70    22    770   663
Cuts at:   1856   1909   1929   2351
  Size:    53    20    422
  Fragments arranged by size:
           770   663   422   166   97   70   58   53   22   20   10
Bsp24I GACnnnnnnTGGnnnnnnn_nnnnn'
Cuts at:   0    76    108   260   292   590   622   882   914
  Size:    76    32    152   32    298   32    260   32
Cuts at:   914   1725   1757   2351
  Size:    811   32    594
  Fragments arranged by size:
           811   594   298   260   152   76   32   32   32   32   32

FIG. 20D

Bsp1286I G_dGCh'C
Cuts at:   0    80    191    529    1062    1435    1574    1648    1767
  Size:   80    111    338    533    373    139    74    119
Cuts at: 1767    2351
  Size:   584
  Fragments arranged by size:
          584    533    373    338    139    119    111    80    74
BspEI T'CCGG_A
Cuts at:   0    15    2351
  Size:   15    2336
BspGI CTGGAC
Cuts at:   0    416    511    1634    2351
  Size:   416    95    1123    717
  Fragments arranged by size:
          1123    717    416    95
BspMI ACCTGCnnnn'nnnn_
Cuts at:   0    448    997    2351
  Size:   448    549    1354
  Fragments arranged by size:
          1354    549    448
BsrI ACTG_Gn'
Cuts at:   0    324    635    773    810    1779    2351
  Size:   324    311    138    37    969    572
  Fragments arranged by size:
          969    572    324    311    138    37
BsrBI GAG'CGG
Cuts at:   0    1192    2351
  Size:   1192    1159
BsrDI GCAATG_nn'
Cuts at:   0    2101    2351
  Size:   2101    250
BstXI CCAn_nnnn'nTGG
Cuts at:   0    963    2351
  Size:   963    1388
BstYI r'GATC_y
Cuts at:   0    337    1024    2351
  Size:   337    687    1327
  Fragments arranged by size:
          1327    687    337
Bsu36I CC'TnA_GG
Cuts at:   0    1089    1153    2351
  Size:   1089    64    1198
  Fragments arranged by size:
          1198    1089    64

FIG. 20E

CviRI TG'CA
Cuts at:    0    425    577    616    695   1237   1491   1770   2174
  Size:      425    152     39     79    542    254    279    404
Cuts at: 2174   2351
  Size:      177
  Fragments arranged by size:
            542    425    404    279    254    177    152     79     39
DpnI GA'TC
Cuts at:    0    339    474    897   1026   1518   2351
  Size:      339    135    423    129    492    833
  Fragments arranged by size:
            833    492    423    339    135    129
DraIII CAC_nnn'GTG
Cuts at:    0   1886   2035   2351
  Size:     1886    149    316
  Fragments arranged by size:
           1886    316    149
DrdI GACnn_nn'nnGTC
Cuts at:    0    353   1239   2351
  Size:      353    886   1112
  Fragments arranged by size:
           1112    886    353
DrdII GAACCA
Cuts at:    0    146    634    659   2351
  Size:      146    488     25   1692
  Fragments arranged by size:
           1692    488    146     25
DsaI C'CryG_G
Cuts at:    0   1144   1213   1402   1477   1507   2351
  Size:     1144     69    189     75     30    844
  Fragments arranged by size:
           1144    844    189     75     69     30
EaeI y'GGCC_r
Cuts at:    0    321    382    977   1193   2041   2098   2351
  Size:      321     61    595    216    848     57    253
  Fragments arranged by size:
            848    595    321    253    216     61     57

FIG. 20F

EarI CTCTTCn'nnn_
Cuts at:   0    54   2351
  Size:       54   2297
EciI TCCGCC
Cuts at:   0   259   2351
  Size:      259   2092
Eco57I CTGAAGnnnnnnnnnnnnnnn_nn'
Cuts at:   0   1787   2283   2351
  Size:      1787   496    68
  Fragments arranged by size:
             1787   496    68
EcoNI CCTnn'n_nnAGG
Cuts at:   0   206   840   1698   2351
  Size:      206   634   858    653
  Fragments arranged by size:
             858   653   634    206
EcoO109I rG'GnC_Cy
Cuts at:   0   305   845   986   1149   1628   2244   2351
  Size:      305   540   141   163    479    616    107
  Fragments arranged by size:
             616   540   479   305    163    141    107
EcoRI G'AATT_C
Cuts at:   0   1442   1551   2351
  Size:      1442   109    800
  Fragments arranged by size:
             1442   800    109
FauI CCCGCnnnn'nn_
Cuts at:   0    65   205   290   1071   1295   2140   2351
  Size:       65   140    85   781    224    845    211
  Fragments arranged by size:
             845   781   224   211    140     85     65
FokI GGATGnnnnnnnnn'nnnn_
Cuts at:   0   185   273   288   462   828   891   1293   1488
  Size:      185    88    15   174   366    63   402    195
Cuts at: 1488   2351
  Size:      863
  Fragments arranged by size:
             863   402   366   195   185   174    88    63    15

FIG. 20G

FspI TGC'GCA
Cuts at:   0    1541   2351
  Size:    1541   810
GdiII y'GGCC_G
Cuts at:   0    321   382   977   1193   2098   2351
  Size:    321   61    595   216   905    253
  Fragments arranged by size:
           905   595   321   253   216   61
HaeI wGG'CCw
Cuts at:   0    1315   2043   2351
  Size:    1315   728   308
  Fragments arranged by size:
           1315   728   308
HaeII r_GCGC'y
Cuts at:   0    810   1050   2351
  Size:    810   240   1301
  Fragments arranged by size:
           1301   810   240
HgaI GACGCnnnnn'nnnnn_
Cuts at:   0    40    1207   2351
  Size:    40    1167   1144
  Fragments arranged by size:
           1167   1144   40
HgiEII ACCnnnnnnnGGT
Cuts at:   0    275   2351
  Size:    275   2076
HhaI G_CG'C
Cuts at:   0    809   920   1049   1118   1542   2151   2239   2351
  Size:    809   111   129   69     424    609    88     112
  Fragments arranged by size:
           809   609   424   129   112   111   88   69
Hin4I GAbnnnnnnvTC
Cuts at:   0    1289   1459   1588   1845   2351
  Size:    1289   170   129   257   506
  Fragments arranged by size:
           1289   506   257   170   129
HincII GTy'rAC
Cuts at:   0    609   1523   2351
  Size:    609   914   828
  Fragments arranged by size:
           914   828   609

FIG. 20H

```
HindIII A'AGCT_T
Cuts at:    0    903   2351
   Size:      903   1448
HinfI G'AnT_C
Cuts at:    0    19   354   487   516   1002   1041   1597   1790
   Size:      19   335   133    29   486     39    556    193
Cuts at: 1790  1877  2351
   Size:      87   474
   Fragments arranged by size:
          556   486   474   335   193   133    87    39    29    19
HphI GGTGAnnnnnnn_n'
Cuts at:    0    191  1121  2351
   Size:     191   930  1230
   Fragments arranged by size:
         1230   930   191
KpnI G_GTAC'C
Cuts at:    0   1397  2351
   Size:    1397   954
MaeII A'CG_T
Cuts at:    0    112   712  1201  1705  1714  1915  2064  2351
   Size:     112   600   489   504     9    201   149   287
   Fragments arranged by size:
          600   504   489   287   201   149   112     9
MaeIII 'GTnAC_
Cuts at:    0    266   517  1202  1838  2093  2351
   Size:     266   251   685   636   255   258
   Fragments arranged by size:
          685   636   266   258   255   251
MboII GAAGAnnnnnnn_n'
Cuts at:    0    41   188   404   545   900   1094  1175  2082
   Size:      41   147   216   141   355   194    81    907
Cuts at: 2082  2351
   Size:     269
   Fragments arranged by size:
          907   355   269   216   194   147   141    81    41
```

FIG. 20I

MmeI TCCrACnnnnnnnnnnnnnnnnnnn_nn'
Cuts at:   0   2248   2351
   Size:   2248   103
MscI TGG'CCA
Cuts at:   0   2043   2351
   Size:   2043   308
MseI T'TA_A
Cuts at:   0   724   2351
   Size:   724   1627
MslI CAynn'nnrTG
Cuts at:   0   204   373   480   1476   1506   2351
   Size:   204   169   107   996   30   845
  Fragments arranged by size:
         996   845   204   169   107   30
MspI C'CG_G
Cuts at:   0   16   237   302   431   653   976   1340   1678
   Size:   16   221   65   129   222   323   364   338
Cuts at:   1678   1974   2351
   Size:   296   377
  Fragments arranged by size:
         377   364   338   323   296   222   221   129   65   16
MspA1I CmG'CkG
Cuts at:   0   413   422   465   565   2351
   Size:   413   9   43   100   1786
  Fragments arranged by size:
         1786   413   100   43   9
NarI GG'CG_CC
Cuts at:   0   807   2351
   Size:   807   1544
NciI CC's_GG
Cuts at:   0   238   303   653   654   976   1679   1974   2351
   Size:   238   65   350   1   322   703   295   377
  Fragments arranged by size:
         703   377   350   322   295   238   65   1
NcoI C'CATG_G
Cuts at:   0   1507   2351
   Size:   1507   844
NheI G'CTAG_C
Cuts at:   0   2182   2351
   Size:   2182   169
NlaIII _CATG'
Cuts at:   0   44   287   858   1441   1511   2351
   Size:   44   243   571   583   70   840
  Fragments arranged by size:
         840   583   571   243   70   44

FIG. 20J

PflMI CCAn_nnn'nTGG
Cuts at:   0    1631   2351
   Size:       1631    720
PleI GAGTCnnnn'n_
Cuts at:   0    27   362   524   996   1591   2351
   Size:       27   335   162   472   595   760
   Fragments arranged by size:
               760   595   472   335   162   27
PmlI CAC'GTG
Cuts at:   0    1916   2351
   Size:       1916    435
Psp5II rG'GwC_Cy
Cuts at:   0    305   845   986   1149   2244   2351
   Size:       305   540   141   163   1095   107
   Fragments arranged by size:
               1095   540   305   163   141   107
Psp1406I AA'CG_TT
Cuts at:   0    112   2351
   Size:       112    2239
PstI C_TGCA'G
Cuts at:   0    697   1493   1772   2351
   Size:       697   796   279   579
   Fragments arranged by size:
               796   697   579   279
PvuII CAG'CTG
Cuts at:   0    413   422   565   2351
   Size:       413   9    143   1786
   Fragments arranged by size:
               1786   413   143   9
RsaI GT'AC
Cuts at:   0    125   501   1053   1122   1395   1665   2351
   Size:       125   376   552   69    273   270   686
   Fragments arranged by size:
               686   552   376   273   270   125   69
SanDI GG'GwC_CC
Cuts at:   0    305   2351
   Size:       305   2046
SapI GCTCTTCn'nnn_
Cuts at:   0    54   2351
   Size:       54   2297
Sau3AI 'GATC_
Cuts at:   0    337   472   895   1024   1516   2351
   Size:       337   135   423   129   492   835
   Fragments arranged by size:
               835   492   423   337   135   129

FIG. 20K

ScaI AGT'ACT
Cuts at:     0    1665   2351
  Size:     1665   686
SfaNI GCATCnnnnn'nnnn_
Cuts at:     0    250    251    806    1246   1256   2351
  Size:     250    1     555    440    10    1095
  Fragments arranged by size:
            1095   555    440    250    10     1
SfcI C'TryA_G
Cuts at:     0    693    1489   1768   2351
  Size:     693    796    279    583
  Fragments arranged by size:
            796    693    583    279
SmaI CCC'GGG
Cuts at:     0    654    2351
  Size:     654    1697
SspI AAT'ATT
Cuts at:     0    2076   2351
  Size:     2076   275
StyI C'CwwG_G
Cuts at:     0    71     80     223    452    1507   2351
  Size:     71     9     143    229    1055   844
  Fragments arranged by size:
            1055   844    229    143    71     9
TaqI T'CG_A
Cuts at:     0    116    523    1032   1819   2351
  Size:     116    407    509    787    532
  Fragments arranged by size:
            787    532    509    407    116
TaqII GACCGAnnnnnnnnnn_nn'
Cuts at:     0    174    457    2351
  Size:     174    283    1894
  Fragments arranged by size:
            1894   283    174
TauI GCsGC
Cuts at:     0    155    321    1193   2351
  Size:     155    166    872    1158
  Fragments arranged by size:
            1158   872    166    155
TfiI G'AwT_C
Cuts at:     0    487    1041   1790   1877   2351
  Size:     487    554    749    87     474
  Fragments arranged by size:
            749    554    487    474    87

FIG. 20L

ThaI CG'CG
Cuts at:      0      246     1118    2239    2351
  Size:      246     872     1121    112
  Fragments arranged by size:
             1121    872     246     112
TseI GCwGC
Cuts at:      0      97      331     401     423     1856    1909    1929    2351
  Size:      97      234     70      22      1433    53      20      422
  Fragments arranged by size:
             1433    422     234     97      70      53      22      20
Tsp45I 'GTsAC_
Cuts at:      0      266     517     1202    1838    2093    2351
  Size:      266     251     685     636     255     258
  Fragments arranged by size:
             685     636     266     258     255     251
Tsp509I 'AATT_
Cuts at:      0      549     1442    1551    2298    2329    2351
  Size:      549     893     109     747     31      22
  Fragments arranged by size:
             893     747     549     109     31      22
TspRI CAGTGnn'
Cuts at:      0      171     642     742     817     1182    1232    1304    1772
  Size:      171     471     100     75      365     50      72      468
Cuts at:   1772     2036    2351
  Size:      264     315
  Fragments arranged by size:
             471     468     365     315     264     171     100     75      72      50
Tth111I GACn'n_nGTC
Cuts at:      0      88      515     1737    2351
  Size:      88      427     1222    614
  Fragments arranged by size:
             1222    614     427     88
Tth111II CAArCAnnnnnnnnn_nn'
Cuts at:      0      279     604     729     1368    1938    1976    2351
  Size:      279     325     125     639     570     38      375
  Fragments arranged by size:
             639     570     375     325     279     125     38

FIG. 20M

UbaCI wGTACw
Cuts at:    0    1665    2351
   Size:      1665    686
XcmI CCAnnnn_n'nnnnTGG
Cuts at:    0    450    2351
   Size:       450    1901
XhoI C'TCGA_G
Cuts at:    0    522    2351
   Size:       522    1829
XmnI GAAnn'nnTTC
Cuts at:    0    48    232    2351
   Size:       48    184    2119
  Fragments arranged by size:
           2119    184    48
Enzymes that do cut and were not excluded:

| AceIII | AflIII | AhdI | AlwI | AlwNI | ApoI | AvaI | AvaII |
|---|---|---|---|---|---|---|---|
| BamHI | BanI | BanII | BbsI | BbvI | BccI | Bce83I | BcefI |
| BfaI | BfiI | BglI | BglII | BmgI | BpmI | Bpu10I | BsaI |
| BsaAI | BsaHI | BsaWI | BsaXI | BsbI | BscGI | BseRI | BsiHKAI |
| BsmAI | BsmBI | BsoFI | Bsp24I | Bsp1286I | BspEI | BspGI | BspMI |
| BsrI | BsrBI | BsrDI | BstXI | BstYI | Bsu36I | CviRI | DpnI |
| DraIII | DrdI | DrdII | DsaI | EaeI | EarI | EciI | Eco57I |
| EcoNI | EcoO109I | EcoRI | FauI | FokI | FspI | GdiII | HaeI |
| HaeII | HgaI | Hgi EII | HhaI | Hin4I | HincII | HindIII |
| HinfI | HphI | KpnI | MaeII | MaeIII | MboII | MmeI | MscI |
| MseI | MslI | MspI | MspA1I | NarI | NciI | NcoI | NheI |
| NlaIII | PflMI | PleI | PmlI | Psp5II | Psp1406I | PstI | PvuII |
| RsaI | SanDI | SapI | Sau3AI | ScaI | SfaNI | SfcI | SmaI |
| SspI | StyI | TaqI | TaqII | TauI | TfiI | ThaI | TseI |
| Tsp45I | Tsp509I | TspRI | Tth111I | Tth111II | UbaCI | XcmI | XhoI |
| XmnI | | | | | | | |

Enzymes that do not cut:

| AatII | AccI | AflII | ApaI | ApaBI | ApaLI | AscI | AvrII |
|---|---|---|---|---|---|---|---|
| BaeI | BcgI | BcgI | BclI | BplI | Bpu1102I | BsaBI | BsgI |
| BsiEI | BsmI | BspLU11I | BsrFI | BsrGI | BssHII | BssSI | Bst1107I |
| BstEII | ClaI | DraI | EagI | Eco47III | EcoRV | FseI | HpaI |
| MluI | MunI | NdeI | NgoAIV | NotI | NruI | NsiI | NspI |
| NspV | PacI | Pfl1108I | PinAI | PmeI | PshAI | PvuI | RcaI |
| RleAI | RsrII | SacI | SacII | SalI | SexAI | SfiI | SgfI |
| SgrAI | SnaBI | SpeI | SphI | SrfI | Sse8387I | Sse8647I | StuI |
| SunI | SwaI | VspI | XbaI | | | | |

Enzymes excluded; MinCuts: 1    MaxCuts: 10

| AciI | AluI | BsaJI | BslI | BsmFI | Cac8I | CjeI | CjeI |
|---|---|---|---|---|---|---|---|
| CjePI | CjePI | CviJI | DdeI | EcoRII | HaeIII | MnlI | MwoI |
| NlaIV | Sau96I | ScrFI | | | | | |

FIG. 20N

SEQUENCE LISTING

<160> NUMBER OF SEQ ID NOS: 14

<210> SEQ ID NO 1
<211> LENGTH: 2360
<212> TYPE: DNA
<213> ORGANISM: Homo sapiens

<400> SEQUENCE: 1
gaattccgac cgcagacatg aaacttgtct tcctcgtcct gctgttcctc ggggccctcg    60
gactgtgtct ggctggccgt aggagaagga gtgttcagtg gtgcaccgta tcccaacccg   120

-continued

```
aggccacaaa atgcttccaa tggcaaagga atatgagaag agtgcgtggc cctcctgtca    180
gctgcataaa gagagactcc cccatccagt gtatccaggc cattgcggaa acagggccg     240 atgctgtgac ccttgatggt ggtttcatat acgaggcagg cctggccccc tacaaactgc    300
gacctgtagc ggcggaagtc tacgggaccg aaagacagcc acgaactcac tattatgccg    360
tggctgtggt gaagaagggc ggcagctttc agctgaacga actgcaaggt ctgaagtcct    420
gccacacagg ccttcgcagg accgctggat ggaatgtgcc tatagggaca cttcgtccat    480
tcttgaattg gacgggtcca cctgagccca ttgaggcagc tgtggccagg ttcttctcag    540
ccagctgtgt tcccggtgca gataaaggac agttccccaa cctgtgtcgc ctgtgtgcgg    600
ggacagggga aaacaaatgt gccttctcct cccaggaacc gtacttcagc tactctggtg    660
ccttcaagtg tctgagagac ggggctggag acgtggcttt tatcagagag agcacagtgt    720
ttgaggacct gtcagacgag gctgaaaggg acgagtatga gttactctgc cagacaaca    780 ctcggaagcc agtggacaag ttcaaagact gccatctggc ccgggtccct tctcatgccg    840
ttgtggcacg aagtgtgaat ggcaaggagg atgccatctg gaatcttctc cgccaggcac    900
aggaaaagtt tggaaaggac aagtcaccga aattccagct ctttggctcc cctagtgggc    960
agaaagatct gctgttcaag gactctgcca ttgggttttc gagggtgccc ccgaggatag    1020
attctgggct gtaccttggc tccggctact tcactgccat ccagaacttg aggaaaagtg    1080
aggaggaagt ggctgcccgg cgtgcgcggg tcgtgtggtg tgcggtgggc gagcaggagc    1140
tgcgcaagtg taaccagtgg agtggcttga gcgaaggcag cgtgacctgc tcctcggcct    1200
ccaccacaga ggactgcatc gccctggtgc tgaaaggaga agctgatgcc atgagtttgg    1260
atggaggata tgtgtacact gcaggcaaat gtggtttggt gcctgtcctg gcagagaact    1320
acaaatccca caaagcagt gaccctgatc ctaactgtgt ggatagacct gtggaaggat    1380
atcttgctgt ggcggtggtt aggagatcag acactagcct tacctggaac tctgtgaaag    1440
gcaagaagtc ctgccacacc gccgtggaca ggactgcagg ctggaatatc ccatgggcc     1500 tgctcttcaa ccagacgggc tcctgcaaat ttgatgaata tttcagtcaa agctgtgccc    1560
ctgggtctga cccgagatct aatctctgtg ctctgtgtat tggcgacgag cagggtgaga    1620
ataagtgcgt gcccaacagc aatgagagat actacggcta cactgggct ttccggtgcc     1680 tggctgagaa tgctggagac gttgcatttg tgaaagatgt cactgtcttg cagaacactg    1740
atggaaataa caatgaggca tgggctaagg atttgaagct ggcagacttt gcgctgctgt    1800
gcctcgatgg caaacggaag cctgtgactg aggctagaag ctgccatctt gccatggccc    1860
cgaatcatgc cgtggtgtct cggatggata aggtggaacg cctgaaacag gtgctgctcc    1920
accaacaggc taaatttggg agaaatggat ctgactgccc ggacaagttt tgcttattcc    1980
agtctgaaac caaaaacctt ctgttcaatg acaacactga gtgtctggcc agactccatg    2040
gcaaaacaac atatgaaaaa tatttgggac acagtatgt cgcaggcatt actaatctga    2100
aaaagtgctc aacctccccc ctcctggaag cctgtgaatt cctcaggaag taaaaccgaa    2160
gaagatggcc cagctcccca agaaagcctc agccattcac tgccccagc tcttctcccc     2220 aggtgtgttg gggccttggc tcccctgctg aaggtgggga ttgcccatcc atctgcttac    2280
aattccctgc tgtcgtctta gcaagaagta aaatgagaaa ttttgttgaa aaaaaaaaa    2340 aaaaaaaaaa aaaaaaaaaa                                               2360
```

<210> SEQ ID NO 2

```
<211> LENGTH: 711
<212> TYPE: PRT
<213> ORGANISM: Homo sapiens

<400> SEQUENCE: 2

Met Lys Leu Val Phe Leu Val Leu Leu Phe Leu Gly Ala Leu Gly Leu
 1               5                  10                  15

Cys Leu Ala Gly Arg Arg Arg Ser Val Gln Trp Cys Thr Val Ser
            20                  25                  30

Gln Pro Glu Ala Thr Lys Cys Phe Gln Trp Gln Arg Asn Met Arg Arg
        35                  40                  45

Val Arg Gly Pro Pro Val Ser Cys Ile Lys Arg Asp Ser Pro Ile Gln
    50                  55                  60

Cys Ile Gln Ala Ile Ala Glu Asn Arg Ala Asp Ala Val Thr Leu Asp
65                  70                  75                  80

Gly Gly Phe Ile Tyr Glu Ala Gly Leu Ala Pro Tyr Lys Leu Arg Pro
                85                  90                  95

Val Ala Ala Glu Val Tyr Gly Thr Glu Arg Gln Pro Arg Thr His Tyr
            100                 105                 110

Tyr Ala Val Ala Val Val Lys Lys Gly Gly Ser Phe Gln Leu Asn Glu
        115                 120                 125

Leu Gln Gly Leu Lys Ser Cys His Thr Gly Leu Arg Arg Thr Ala Gly
130                 135                 140

Trp Asn Val Pro Ile Gly Thr Leu Arg Pro Phe Leu Asn Trp Thr Gly
145                 150                 155                 160

Pro Pro Glu Pro Ile Glu Ala Ala Val Ala Arg Phe Phe Ser Ala Ser
                165                 170                 175

Cys Val Pro Gly Ala Asp Lys Gly Gln Phe Pro Asn Leu Cys Arg Leu
            180                 185                 190

Cys Ala Gly Thr Gly Glu Asn Lys Cys Ala Phe Ser Ser Gln Glu Pro
        195                 200                 205

Tyr Phe Ser Tyr Ser Gly Ala Phe Lys Cys Leu Arg Asp Gly Ala Gly
    210                 215                 220

Asp Val Ala Phe Ile Arg Glu Ser Thr Val Phe Glu Asp Leu Ser Asp
225                 230                 235                 240

Glu Ala Glu Arg Asp Glu Tyr Glu Leu Leu Cys Pro Asp Asn Thr Arg
                245                 250                 255

Lys Pro Val Asp Lys Phe Lys Asp Cys His Leu Ala Arg Val Pro Ser
            260                 265                 270

His Ala Val Val Ala Arg Ser Val Asn Gly Lys Glu Asp Ala Ile Trp
        275                 280                 285

Asn Leu Leu Arg Gln Ala Gln Glu Lys Phe Gly Lys Asp Lys Ser Pro
    290                 295                 300

Lys Phe Gln Leu Phe Gly Ser Pro Ser Gly Gln Lys Asp Leu Leu Phe
305                 310                 315                 320

Lys Asp Ser Ala Ile Gly Phe Ser Arg Val Pro Pro Arg Ile Asp Ser
                325                 330                 335

Gly Leu Tyr Leu Gly Ser Gly Tyr Phe Thr Ala Ile Gln Asn Leu Arg
            340                 345                 350

Lys Ser Glu Glu Glu Val Ala Ala Arg Arg Ala Arg Val Val Trp Cys
        355                 360                 365

Ala Val Gly Glu Gln Glu Leu Arg Lys Cys Asn Gln Trp Ser Gly Leu
    370                 375                 380

Ser Glu Gly Ser Val Thr Cys Ser Ser Ala Ser Thr Thr Glu Asp Cys
```

```
                385                 390                 395                 400

Ile Ala Leu Val Leu Lys Gly Glu Ala Asp Ala Met Ser Leu Asp Gly
                    405                 410                 415
Gly Tyr Val Tyr Thr Ala Gly Lys Cys Gly Leu Val Pro Val Leu Ala
                420                 425                 430
Glu Asn Tyr Lys Ser Gln Gln Ser Ser Asp Pro Asp Pro Asn Cys Val
            435                 440                 445
Asp Arg Pro Val Glu Gly Tyr Leu Ala Val Ala Val Val Arg Arg Ser
        450                 455                 460
Asp Thr Ser Leu Thr Trp Asn Ser Val Lys Gly Lys Lys Ser Cys His
465                 470                 475                 480
Thr Ala Val Asp Arg Thr Ala Gly Trp Asn Ile Pro Met Gly Leu Leu
                485                 490                 495
Phe Asn Gln Thr Gly Ser Cys Lys Phe Asp Glu Tyr Phe Ser Gln Ser
                500                 505                 510
Cys Ala Pro Gly Ser Asp Pro Arg Ser Asn Leu Cys Ala Leu Cys Ile
            515                 520                 525
Gly Asp Glu Gln Gly Glu Asn Lys Cys Val Pro Asn Ser Asn Glu Arg
        530                 535                 540
Tyr Tyr Gly Tyr Thr Gly Ala Phe Arg Cys Leu Ala Glu Asn Ala Gly
545                 550                 555                 560
Asp Val Ala Phe Val Lys Asp Val Thr Val Leu Gln Asn Thr Asp Gly
                565                 570                 575
Asn Asn Asn Glu Ala Trp Ala Lys Asp Leu Lys Leu Ala Asp Phe Ala
                580                 585                 590
Leu Leu Cys Leu Asp Gly Lys Arg Lys Pro Val Thr Glu Ala Arg Ser
            595                 600                 605
Cys His Leu Ala Met Ala Pro Asn His Ala Val Ser Arg Met Asp
        610                 615                 620
Lys Val Glu Arg Leu Lys Gln Val Leu Leu His Gln Gln Ala Lys Phe
625                 630                 635                 640
Gly Arg Asn Gly Ser Asp Cys Pro Asp Lys Phe Cys Leu Phe Gln Ser
                645                 650                 655
Glu Thr Lys Asn Leu Leu Phe Asn Asp Asn Thr Glu Cys Leu Ala Arg
                660                 665                 670
Leu His Gly Lys Thr Thr Tyr Glu Lys Tyr Leu Gly Pro Gln Tyr Val
            675                 680                 685
Ala Gly Ile Thr Asn Leu Lys Lys Cys Ser Thr Ser Pro Leu Leu Glu
        690                 695                 700
Ala Cys Glu Phe Leu Arg Lys
705                 710

<210> SEQ ID NO 3
<211> LENGTH: 2347
<212> TYPE: DNA
<213> ORGANISM: Bos taurus

<400> SEQUENCE: 3
gagccttcgt tccggagtcg ccccaggacg ccagcccatg aagctcttcg tccccgccct      60
cctgtccctt ggagcccttg gactgtgtct ggctgccccg aggaaaaacg ttcgatggtg     120
taccatctcc caacctgagt ggttcaaatg ccgcagatgg cagtggagga tgaagaagct     180
gggtgctccc tctatcacct gtgtgaggcg ggcctttgcc ttggaatgta ttccgggcat     240
cgcggagaaa aaggcggatg ctgtgaccct ggatggtggc atggtgtttg aggcgggccg     300
```

```
ggaccoctac aaactgcggc cagtagcagc agagatctat gggacgaaag agtctcccca      360
aacccactat tatgctgtgg ccgtcgtgaa gaagggcagc aactttcagc tggaccagct      420
gcaaggccgg aagtcctgcc atacgggcct tggcaggtcc gctggtgga tcatccctat      480 gggaatcctt cgcccgtact tgagctggac agagtcactc gagcccctcc agggagctgt     540
ggctaaattc ttctctgcca gctgtgttcc ctgcattgat agacaagcat accccaacct     600
gtgtcaactg tgcaaggggg aggggagaa ccagtgtgcc tgctcctccc gggaaccata     660
cttcggttat tctggtgcct tcaagtgtct gcaggacggg gctggagacg tggcttttgt     720
taaagagacg acagtgtttg agaacttgcc agagaaggct gacagggacc agtatgagct     780
tctctgcctg aacaacagtc gggcgccagt ggatgcgttc aaggagtgcc acctggccca     840
ggtcccttct catgctgtcg tggcccgaag tgtggatggc aaggaagact tgatctggaa     900
gcttctcagc aaggcgcagg agaaatctgg aaaaaacaag tctcggagct ccagctctt     960 tggctctcca cccggccaga gggacctgct gttcaaagac tctgctcttg gttttttgag    1020
gatcccctcg aagqtagatt cqgcgctgta cctgqgctcc cqctacttga ccaccttgaa    1080 gaacctcagg gaaactgcgg aggaggtgaa ggcgcggtac accagggtcg tgtggtgtgc    1140
cgtgggacct gaggagcaga agaagtgcca gcagtgagc cagcagagcg ccagaacgt     1200 gacctgtgcc acggcgtcca ccactgacga ctgcatcgtc ctggtgctga agggaagc    1260 agatgccctg aacttggatg gaggatatat ctacactgcg ggcaagtgtg gcctggtgcc    1320
tgtcctggca gagaaccgga atcctccaa acacagtagc ctagattgtg tgctgagacc     1380
aacggaaggg taccttgccg tggcagttgt caagaaagca aatgaggggc tcacatggaa    1440
ttctctgaaa gacaagaagt cgtgccacac cgccgtggac aggactgcag gctggaacat    1500
ccccatgggc ctgatcgtca accagacagg ctcctgcgca tttgatgaat tctttagtca    1560
gagctgtgcc cctggggctg acccgaaatc cagactctgt gccttgtgtg ctggcgatga    1620
ccagggcctg gacaagtgtg tgcccaactc taaggagaag tactatggct ataccggggc    1680
tttcaggtgc ctggctgagg acgttgggga cgttgccttt gtgaaaaacg acacagtctg    1740
ggagaacacg aatggagaga gcactgcaga ctgggctaag aacttgaatc gtgaggactt    1800
caggttgctc tgcctcgatg caccaggaa gcctgtgacg gaggctcaga gctgccacct    1860
ggcggtggcc ccgaatcacg ctgtggtgtc tcggagcgat agggcagcac acgtgaaaca    1920
ggtgctgctc caccagcagg ctctgttgg gaaaaatgga aaaaactgcc cggacaagtt    1980 ttgttgttc aaatctgaaa ccaaaaacct tctgttcaat gacaacactg agtgtctggc    2040
caaacttgga ggcagaccaa cgtatgaaga atatttgggg acagagtatg tcacggccat    2100
tgccaacctg aaaaaatgct caacctcccc gcttctggaa gcctgcgcct tcctgacgag    2160
gtaaagcctg caaagaagct agcctgcctc cctgggcctc agctcctccc tgctctcagc    2220
cccaatctcc aggcgcgagg gaccttcctc tcccttcctg aagtcggatt tttgccaagc    2280
tcatcagtat ttacaattcc ctgctgtcat tttagcaaga aataaaatta gaaatgctgt    2340
tgaaaaa                                                               2347
```

<210> SEQ ID NO 4
<211> LENGTH: 708
<212> TYPE: PRT
<213> ORGANISM: Bos taurus

<400> SEQUENCE: 4

```
Met Lys Leu Phe Val Pro Ala Leu Leu Ser Leu Gly Ala Leu Gly Leu
 1               5                  10                  15

Cys Leu Ala Ala Pro Arg Lys Asn Val Arg Trp Cys Thr Ile Ser Gln
            20                  25                  30

Pro Glu Trp Phe Lys Cys Arg Arg Trp Gln Trp Arg Met Lys Lys Leu
        35                  40                  45

Gly Ala Pro Ser Ile Thr Cys Val Arg Arg Ala Phe Ala Leu Glu Cys
50                  55                  60

Ile Pro Gly Ile Ala Glu Lys Ala Asp Ala Val Thr Leu Asp Gly
65                  70                  75                  80

Gly Met Val Phe Glu Ala Gly Arg Asp Pro Tyr Lys Leu Arg Pro Val
            85                  90                  95

Ala Ala Glu Ile Tyr Gly Thr Lys Glu Ser Pro Gln Thr His Tyr Tyr
            100                 105                 110

Ala Val Ala Val Val Lys Lys Gly Ser Asn Phe Gln Leu Asp Gln Leu
            115                 120                 125

Gln Gly Arg Lys Ser Cys His Thr Gly Leu Gly Arg Ser Ala Gly Trp
130                 135                 140

Ile Ile Pro Met Gly Ile Leu Arg Pro Tyr Leu Ser Trp Thr Glu Ser
145                 150                 155                 160

Leu Glu Pro Leu Gln Gly Ala Val Ala Lys Phe Phe Ser Ala Ser Cys
            165                 170                 175

Val Pro Cys Ile Asp Arg Gln Ala Tyr Pro Asn Leu Cys Gln Leu Cys
            180                 185                 190

Lys Gly Glu Gly Glu Asn Gln Cys Ala Cys Ser Ser Arg Glu Pro Tyr
            195                 200                 205

Phe Gly Tyr Ser Gly Ala Phe Lys Cys Leu Gln Asp Gly Ala Gly Asp
            210                 215                 220

Val Ala Phe Val Lys Glu Thr Thr Val Phe Glu Asn Leu Pro Glu Lys
225                 230                 235                 240

Ala Asp Arg Asp Gln Tyr Glu Leu Leu Cys Leu Asn Asn Ser Arg Ala
            245                 250                 255

Pro Val Asp Ala Phe Lys Glu Cys His Leu Ala Gln Val Pro Ser His
            260                 265                 270

Ala Val Val Ala Arg Ser Val Asp Gly Lys Glu Asp Leu Ile Trp Lys
            275                 280                 285

Leu Leu Ser Lys Ala Gln Glu Lys Ser Gly Lys Asn Lys Ser Arg Ser
            290                 295                 300

Phe Gln Leu Phe Gly Ser Pro Gly Gln Arg Asp Leu Leu Phe Lys
305                 310                 315                 320

Asp Ser Ala Leu Gly Phe Leu Arg Ile Pro Ser Lys Val Asp Ser Ala
            325                 330                 335

Leu Tyr Leu Gly Ser Arg Tyr Leu Thr Thr Leu Lys Asn Leu Arg Glu
            340                 345                 350

Thr Ala Glu Glu Val Lys Ala Arg Tyr Thr Arg Val Val Trp Cys Ala
            355                 360                 365

Val Gly Pro Glu Glu Gln Lys Lys Cys Gln Gln Trp Ser Gln Gln Ser
            370                 375                 380

Gly Gln Asn Val Thr Cys Ala Thr Ala Ser Thr Thr Asp Asp Cys Ile
385                 390                 395                 400

Val Leu Val Leu Lys Gly Glu Ala Asp Ala Leu Asn Leu Asp Gly Gly
            405                 410                 415

Tyr Ile Tyr Thr Ala Gly Lys Cys Gly Leu Val Pro Val Leu Ala Glu
```

```
                     420                 425                 430
Asn Arg Lys Ser Ser Lys His Ser Ser Leu Asp Cys Val Leu Arg Pro
            435                 440                 445
Thr Glu Gly Tyr Leu Ala Val Ala Val Val Lys Lys Ala Asn Glu Gly
    450                 455                 460
Leu Thr Trp Asn Ser Leu Lys Asp Lys Lys Ser Cys His Thr Ala Val
465                 470                 475                 480
Asp Arg Thr Ala Gly Trp Asn Ile Pro Met Gly Leu Ile Val Asn Gln
                485                 490                 495
Thr Gly Ser Cys Ala Phe Asp Glu Phe Phe Ser Gln Ser Cys Ala Pro
            500                 505                 510
Gly Ala Asp Pro Lys Ser Arg Leu Cys Ala Leu Cys Ala Gly Asp Asp
    515                 520                 525
Gln Gly Leu Asp Lys Cys Val Pro Asn Ser Lys Glu Lys Tyr Tyr Gly
    530                 535                 540
Tyr Thr Gly Ala Phe Arg Cys Leu Ala Glu Asp Val Gly Asp Val Ala
545                 550                 555                 560
Phe Val Lys Asn Asp Thr Val Trp Glu Asn Thr Asn Gly Glu Ser Thr
                565                 570                 575
Ala Asp Trp Ala Lys Asn Leu Asn Arg Glu Asp Phe Arg Leu Leu Cys
            580                 585                 590
Leu Asp Gly Thr Arg Lys Pro Val Thr Glu Ala Gln Ser Cys His Leu
    595                 600                 605
Ala Val Ala Pro Asn His Ala Val Val Ser Arg Ser Asp Arg Ala Ala
    610                 615                 620
His Val Lys Gln Val Leu Leu His Gln Gln Ala Leu Phe Gly Lys Asn
625                 630                 635                 640
Gly Lys Asn Cys Pro Asp Lys Phe Cys Leu Phe Lys Ser Glu Thr Lys
                645                 650                 655
Asn Leu Leu Phe Asn Asp Asn Thr Glu Cys Leu Ala Lys Leu Gly Gly
            660                 665                 670
Arg Pro Thr Tyr Glu Glu Tyr Leu Gly Thr Glu Tyr Val Thr Ala Ile
    675                 680                 685
Ala Asn Leu Lys Lys Cys Ser Thr Ser Pro Leu Leu Glu Ala Cys Ala
    690                 695                 700
Phe Leu Thr Arg
705

<210> SEQ ID NO 5
<211> LENGTH: 2259
<212> TYPE: DNA
<213> ORGANISM: Sus scrofa

<400> SEQUENCE: 5
acatgaagct cttcatcccc gccctgctgt tcctcgggac acttggactg tgtctggctg    60
cccctaagaa aggggttcga tggtgtgtca tatccacagc agagtattca aaatgccgcc   120
agtggcaatc aaagataaga agaactaatc ccatgttctg cataaggagg gcttctccca   180
ctgactgtat ccgggccatc gcggcaaaaa gggcagatgc tgtgacccct gatggtggtt   240
tggtgtttga agcagaccag tacaaactgc ggccggtagc agcggagatc tacgggacag   300
aagagaatcc ccaaacctac tattatgctg tggctgtagt gaagaaaggt ttcaactttc   360
agaaccagct acaaggtcga aagtcctgcc acacaggcct tggcaggtct gccgggtgga   420
atatccctat aggggttactt cgccggttct tggactgggc agggccacct gagcccctcc   480
```

-continued

```
agaaagctgt ggccaaattc ttctctcaga gctgtgtgcc ctgcgcagat ggaaatgcgt    540
atcccaacct gtgtcagctg tgcataggga aagggaaaga taaatgtgct tgttcctccc    600
aggaaccgta ttttggctat tccggtgcct tcaactgtct gcacaaaggg attggagatg    660
tggcttttgt caaggagagt acagtgtttg agaacctgcc acagaaggct gaccgggaca    720
aatacgagct actctgccca gacaatactc gaaagccagt ggaagcattc agggagtgcc    780
accttgcccg gtcccttct catgctgttg tggcccgaag tgtgaatggc aaggagaact    840
ccatctggga gcttctctac cagtcacaga aaaagtttgg aaaaagcaat ccacaggagt    900
tccagctctt tggctctcct ggtcagcaga aggacctcct gtttagagat gctaccatcg    960 ggttttttgaa gatcccctca agatagatt ctaagctgta cctgggcctc ccgtaccttu   1020
ctgccatcca gggcctgagg gaaacggcag cggaggtgga ggcgcggcag gcgaaggtcg   1080
tgtggtgcgc cgtgggtcca gaggagctgc gcaagtgccg gcagtggagc agccagagca   1140
gccagaacct gaactgcagc ctggcctcca ccaccgagga ctgcatcgtc caggtgctga   1200
aaggagaagc tgatgctatg agcttggatg gaggatttat ctacactgcg ggcaagtgtg   1260
gtttggtgcc tgtcctggca gagaaccaaa aatctcgcca aagcagtagc tcagactgtg   1320
tgcatagacc aacacaaggg tattttgccg tggcggttgt caggaaagca aatggtggta   1380
tcacctggaa ctctgtgaga ggcacgaagt cctgccacac tgctgtggac aggacagcag   1440 gctgaacat ccccatgggc ctgcttgtca accagacagg ctcctgcaaa tttgacgaat   1500
tctttagtca aagctgtgct cctgggtctc agccgggatc caatctctgt gcactgtgtg   1560
ttggcaatga ccagggcgtg gacaagtgtg tgcccaacag taatgagaga tactatggtt   1620
acaccggggc tttcaggtgc ctggctgaga atgctgggga tgtggcgttt gtgaaagatg   1680
tcactgtctt ggacaacacg aatggacaga acacagaaga gtgggccagg gaattgaggt   1740
cagatgactt tgagctgctg tgccttgatg gcaccaggaa gcctgtgact gaggctcaga   1800
actgtcacct ggctgtggcc cccagtcatg ctgtggtctc tcggaaggaa aaggcagcac   1860
aggtggaaca ggtgctactc actgagcagg ctcagtttgg aagatacgga aaagactgcc   1920
cggacaagtt tgcttgttc cggtctgaga ccaaaaacct tctgttcaac gacaacacgg   1980
aggttctggc ccaactccaa ggcaaaacaa catacgaaaa atatttggga tcagagtatg   2040
tcacagccat cgctaacctg aaacagtgct cagtctcccc gcttctggaa gcctgtgcct   2100
tcatgatgag gtaaaaccgg aaaagaagct gcccgcctcc ccaggggcct cagctttccc   2160
tcctcccgtc ttgattccca gctgccctgg gcctgcctct tcccttcct gagggcagac   2220 tttgttcagc tcatccgttt tcacaattcc ctcgtgccg                          2259
```

<210> SEQ ID NO 6
<211> LENGTH: 703
<212> TYPE: PRT
<213> ORGANISM: Sus scrofa

<400> SEQUENCE: 6

```
Met Lys Leu Phe Ile Pro Ala Leu Leu Phe Leu Gly Thr Leu Gly Leu
  1               5                  10                  15

Cys Leu Ala Ala Pro Lys Lys Gly Val Arg Trp Cys Val Ile Ser Thr
             20                  25                  30

Ala Glu Tyr Ser Lys Cys Arg Gln Trp Gln Ser Lys Ile Arg Arg Thr
         35                  40                  45

Asn Pro Met Phe Cys Ile Arg Arg Ala Ser Pro Thr Asp Cys Ile Arg
```

```
         50                  55                  60
Ala Ile Ala Ala Lys Arg Ala Asp Ala Val Thr Leu Asp Gly Gly Leu
 65                  70                  75                  80

Val Phe Glu Ala Asp Gln Tyr Lys Leu Arg Pro Val Ala Ala Glu Ile
                 85                  90                  95

Tyr Gly Thr Glu Glu Asn Pro Gln Thr Tyr Tyr Ala Val Ala Val
             100                 105                 110

Val Lys Lys Gly Phe Asn Phe Gln Asn Gln Leu Gln Gly Arg Lys Ser
             115                 120                 125

Cys His Thr Gly Leu Gly Arg Ser Ala Gly Trp Asn Ile Pro Ile Gly
             130                 135                 140

Leu Leu Arg Arg Phe Leu Asp Trp Ala Gly Pro Pro Glu Pro Leu Gln
145                 150                 155                 160

Lys Ala Val Ala Lys Phe Phe Ser Gln Ser Cys Val Pro Cys Ala Asp
                 165                 170                 175

Gly Asn Ala Tyr Pro Asn Leu Cys Gln Leu Cys Ile Gly Lys Gly Lys
             180                 185                 190

Asp Lys Cys Ala Cys Ser Ser Gln Glu Pro Tyr Phe Gly Tyr Ser Gly
             195                 200                 205

Ala Phe Asn Cys Leu His Lys Gly Ile Gly Asp Val Ala Phe Val Lys
             210                 215                 220

Glu Ser Thr Val Phe Glu Asn Leu Pro Gln Lys Ala Asp Arg Asp Lys
225                 230                 235                 240

Tyr Glu Leu Leu Cys Pro Asp Asn Thr Arg Lys Pro Val Glu Ala Phe
                 245                 250                 255

Arg Glu Cys His Leu Ala Arg Val Pro Ser His Ala Val Val Ala Arg
             260                 265                 270

Ser Val Asn Gly Lys Glu Asn Ser Ile Trp Glu Leu Leu Tyr Gln Ser
             275                 280                 285

Gln Lys Lys Phe Gly Lys Ser Asn Pro Gln Glu Phe Gln Leu Phe Gly
             290                 295                 300

Ser Pro Gly Gln Gln Lys Asp Leu Leu Phe Arg Asp Ala Thr Ile Gly
305                 310                 315                 320

Phe Leu Lys Ile Pro Ser Lys Ile Asp Ser Lys Leu Tyr Leu Gly Leu
                 325                 330                 335

Pro Tyr Leu Thr Ala Ile Gln Gly Leu Arg Glu Thr Ala Ala Glu Val
             340                 345                 350

Glu Ala Arg Gln Ala Lys Val Val Trp Cys Ala Val Gly Pro Glu Glu
             355                 360                 365

Leu Arg Lys Cys Arg Gln Trp Ser Ser Gln Ser Ser Gln Asn Leu Asn
             370                 375                 380

Cys Ser Leu Ala Ser Thr Thr Glu Asp Cys Ile Val Gln Val Leu Lys
385                 390                 395                 400

Gly Glu Ala Asp Ala Met Ser Leu Asp Gly Gly Phe Ile Tyr Thr Ala
                 405                 410                 415

Gly Lys Cys Gly Leu Val Pro Val Leu Ala Glu Asn Gln Lys Ser Arg
             420                 425                 430

Gln Ser Ser Ser Asp Cys Val His Arg Pro Thr Gln Gly Tyr Phe
             435                 440                 445

Ala Val Ala Val Arg Lys Ala Asn Gly Gly Ile Thr Trp Asn Ser
             450                 455                 460

Val Arg Gly Thr Lys Ser Cys His Thr Ala Val Asp Arg Thr Ala Gly
465                 470                 475                 480
```

```
Trp Asn Ile Pro Met Gly Leu Leu Val Asn Gln Thr Gly Ser Cys Lys
            485                 490                 495
Phe Asp Glu Phe Phe Ser Gln Ser Cys Ala Pro Gly Ser Gln Pro Gly
        500                 505                 510
Ser Asn Leu Cys Ala Leu Cys Val Gly Asn Asp Gln Gly Val Asp Lys
            515                 520                 525
Cys Val Pro Asn Ser Asn Glu Arg Tyr Tyr Gly Tyr Thr Gly Ala Phe
        530                 535                 540
Arg Cys Leu Ala Glu Asn Ala Gly Asp Val Ala Phe Val Lys Asp Val
545                 550                 555                 560
Thr Val Leu Asp Asn Thr Asn Gly Gln Asn Thr Glu Glu Trp Ala Arg
            565                 570                 575
Glu Leu Arg Ser Asp Asp Phe Glu Leu Leu Cys Leu Asp Gly Thr Arg
        580                 585                 590
Lys Pro Val Thr Glu Ala Gln Asn Cys His Leu Ala Val Ala Pro Ser
            595                 600                 605
His Ala Val Val Ser Arg Lys Glu Lys Ala Ala Gln Val Glu Gln Val
        610                 615                 620
Leu Leu Thr Glu Gln Ala Gln Phe Gly Arg Tyr Gly Lys Asp Cys Pro
625                 630                 635                 640
Asp Lys Phe Cys Leu Phe Arg Ser Glu Thr Lys Asn Leu Leu Phe Asn
            645                 650                 655
Asp Asn Thr Glu Val Leu Ala Gln Leu Gln Gly Lys Thr Thr Tyr Glu
        660                 665                 670
Lys Tyr Leu Gly Ser Glu Tyr Val Thr Ala Ile Ala Asn Leu Lys Gln
            675                 680                 685
Cys Ser Val Ser Pro Leu Leu Glu Ala Cys Ala Phe Met Met Arg
        690                 695                 700
```

```
<210> SEQ ID NO 7
<211> LENGTH: 36
<212> TYPE: DNA
<213> ORGANISM: Homo sapiens

<400> SEQUENCE: 7
ctgggtcgac gtaggagaag gagtgttcag tggtgc                        36

<210> SEQ ID NO 8
<211> LENGTH: 24
<212> TYPE: DNA
<213> ORGANISM: Homo sapiens

<400> SEQUENCE: 8
gccgtagact tccgccgcta cagg                                     24

<210> SEQ ID NO 9
<211> LENGTH: 45
<212> TYPE: DNA
<213> ORGANISM: Aspergillus oryzae

<400> SEQUENCE: 9
gaggtaccga attcatggtg ttttgatcat tttaaatttt tatat              45

<210> SEQ ID NO 10
<211> LENGTH: 45
<212> TYPE: DNA
<213> ORGANISM: Aspergillus oryzae
```

-continued

```
<400> SEQUENCE: 10
agcagctgca gccaaagcag gtgccgcgac ctgaaggccg tacag                45

<210> SEQ ID NO 11
<211> LENGTH: 27
<212> TYPE: DNA
<213> ORGANISM: Aspergillus oryzae

<400> SEQUENCE: 11
ctgcccgggc gtaggagaag gagtgtt                                    27

<210> SEQ ID NO 12
<211> LENGTH: 34
<212> TYPE: DNA
<213> ORGANISM: Homo sapiens

<400> SEQUENCE: 12
catggatcct gttttacgca atggcctgga taca                            34

<210> SEQ ID NO 13
<211> LENGTH: 26
<212> TYPE: DNA
<213> ORGANISM: Aspergillus oryzae

<400> SEQUENCE: 13
cggaattcat ggtgttttga tcattt                                     26

<210> SEQ ID NO 14
<211> LENGTH: 52
<212> TYPE: DNA
<213> ORGANISM: Aspergillus oryzae

<400> SEQUENCE: 14
tggaattcga tcgcggatcc gcaatgcatg cagccaaagc aggtgccgcg ac        52
```

PRODUCTION OF RECOMBINANT LACTOFERRIN AND LACTOFERRIN POLYPEPTIDES USING CDNA SEQUENCES IN VARIOUS ORGANISMS

RELATED APPLICATIONS

This application is a divisional application of Ser. No. 08/456,108 filed May 30, 1995, now issued U.S. Pat. No. 6,100,54, which in turn is a divisional application of Ser. No. 08/145,681 filed Oct. 28, 1993, now issued U.S. Pat. No. 5,571,691, which in turn is a continuation in part of application Ser. No. 07/967,947, filed Oct. 27, 1992, now abandoned, which in turn is a continuation of application Ser. No. 07/348,270, filed May 5, 1989, now abandoned. This application is also a continuation in part of application Ser. No. 07/878,304 filed Apr. 24, 1992, now abandoned.

This invention was made with government support under Grant No. HD27965 awarded by the National Institute of Health. The government has certain rights in the invention.

BACKGROUND OF THE INVENTION

1. Field of the Invention

The present invention relates generally to the field of iron-binding glycoproteins. More specifically, the present invention relates to the recombinant production of various lactoferrins.

2. Description of the Prior Art

Lactoferrin (LF) is an iron-binding glycoprotein found in milk and other secretions and body fluids. It is one of a number of iron binding proteins, sometimes referred to as transferring, and is involved in iron binding and delivery in mammals.

Human lactoferrin (hLF) is a member of the transferrin family of iron-binding monomeric glycoproteins. It was originally discovered in milk where it can reach levels of 7 grams/liter in colostrum. LF has since been detected in other external fluids of humans and other mammals. The fluids include tears, saliva and mucosal secretions and also in the secondary granules of polymorphonuclear leukocytes.

Lactoferrin has been implicated as a factor in resistance against enteritis infections in suckled newborn humans. The bacteriocidal/bacteriostatic actions are considered to be due at least in part to the iron binding properties of lactoferrin. Lactoferrin decreases the iron availability to iron-requiring microorganisms and thereby interferes with their growth and reproduction. At least one non-iron-binding bactericidal domain has also been reported for human lactoferrin. Lactoferrin is also considered to have antiviral properties and to have other potential therapeutic applications.

LF is a 78 kilo Dalton (k Da) glycoprotein having a bilobal structure with a high degree of homology between the C and N terminal halves which is evident at both the amino acid and three dimensional structural level. Each of these lobes can reversibly bind one ferric iron with high affinity and with the concomitant binding of bicarbonate. The biological functions proposed for lactoferrin include protection against microbial infection, enhanced intestinal iron absorption in infants, promotion of cell growth, regulation of myelopoiesis and modulation of inflammatory responses.

Human lactoferrin (hLF) has a high affinity for iron and two $Fe^{3+}$ cations can be bound per molecule. The complete HLF protein has been subjected to amino acid sequencing and is reported to have 703 amino acids. There are two glycosylation sites. Metz-Boutigue et al., *Eur. J. Biochem.*, 145:659–676 (1984). Anderson et al., *Proc. Nat'l Acad. Sci. USA*, 84:1769–1773 (April 1987).

In other studies, a cloned cDNA probe for amino acids 428 to 703 of the Metz-Boutigue structure of the lactoferrin protein was isolated. The cDNA sequence was in general agreement with the earlier analysis of the amino acid sequence of the protein. Rado et al., *Blood*, 79; 4:989–993, 79; 4:989–993 (October 1987). The probe was reported to encompass approximately 40% of the coding region and the 3' terminus. The cDNA sequence for both porcine, Lydon, J. P., et al., *Biochem. Biophysic. ACTA*, 1132:97–99 (1992); Alexander, L. J., et al., *Animal Genetics*, 23:251–256 (1992) and bovine lactoferrin, Mead, P. E., et al., *Nucleic Acids Research*, 18:7167 (1990); Pierce, A., et al., *Eur. J. Biochem.*, 196:177–184 (1991), have been determined.

Polypeptides derived from lactoferrin are also known to be biologically active. A fragment containing a possible iron binding site was reported by Rado, et al. supra. An N-terminal human lactoferrin fragment, including a bactericidal domain of HLF, was isolated from a pepsin digest. Bellamy, W. M., et al., *Biochem. Biophys. ACTA*, 1121:130–136 (1992). Synthetic 23 and 25 amino acid polypeptides were synthesized and found to have activities similar to the fragments derived by pepsin digestion. The synthesis details, yields and purity of the synthetic peptides were not reported. Bellamy et al. do not provide a practical route to large scale production of the polypeptides free of the contaminates resulting form isolation from natural products.

The bactericidal domain from lactoferrin has a broad spectrum of antimicrobial action. Bellamy, W. M. et al., *J. App. Bact.* 73, 472–479 (1992). Although Bellamy et al. report that bovine lactoferrin isolated from milk can provide commercial quantities of the bovine polypeptide by pepsin digestion, the materials used in both studies had a minimum purity of only 95%. Bellamy, et al. do not provide constructs for the large scale production of synthetic human or bovine lactoferrin or lactoferrin polypeptides. Neither does Bellamy et al. provide the ability to produce peptides that are not available by enzyme digestion.

Filamentous fungi have been successfully employed as hosts in the industrial production of extracellular glycoproteins. Certain industrial strains are capable of secreting gram quantities of these proteins. In addition, filamentous fungi are able to correctly perform post-translational modifications of eucaryotic proteins and many strains have U.S. Food and Drug Administration approval. Furthermore, large scale fermentation technology and downstream processing experience is available.

Currently, there is no efficient and economical way to produce hLF, other species lactoferrin, or to control production of lactoferrin polypeptides. Consequently, a long felt need and description in this art would be met by the development of an efficient method for the production of human lactoferrin for nutritional and therapeutic applications and for further investigation into its mechanism of action.

SUMMARY OF THE INVENTION

The invention comprises the verified cDNA sequences for human lactoferrin, and cDNA expression systems for use of various lactoferrin DNA sequences to produce human, bovine, porcine and other lactoferrins for a variety of end uses. The cDNA expression systems of the invention also provide a practical route and method to make lactoferrin polypeptides or fragments having biological activity. The hLF cDNA includes an open reading frame of 2133 nucleotides coding for a protein of 711 amino acids. These 711 amino acids include 19 amino acids corresponding to a secretion signal peptide sequence followed by 692 amino acids of mature human lactoferrin. The cDNA sequence and deduced amino acid sequence differ from the previously published data of Metz-Boutigue, supra.

In one embodiment, the present invention provides for a recombinant plasmid comprising the cDNA of human or other lactoferrin. The plasmid of the present invention is adapted for expression in a eucaryotic cell and contains the regulatory elements necessary for the expression of the human lactoferrin cDNA in this eucaryotic cell.

In another embodiment, the present invention provides for a transformed cell which includes a heterologous DNA sequence which codes for lactoferrin or a polypeptide related to lactoferrin. The heterologous DNA sequence will preferably be incorporated into a plasmid. Eucaryotic host cells are selected from the group consisting of mammalian cells, immortalized mamunalian cells, fungi or yeasts. Preferred cells include filamentous fungi comprising Aspergillus, and yeasts. The plasmid contains a plasmid vector into which a polydeoxyribonucleotide (DNA) segment coding for human or other lactoferrin protein has been inserted.

In yet another embodiment of the present invention, there is provided a process for producing recombinant human or other lactoferrin which comprises culturing a transformant eucaryotic cell, which includes a recombinant plasmid. The plasmid contains a plasmid vector having a polydeoxyribonucleotide coding for the lactoferrin protein. After culturing in a suitable nutrient medium until lactoferrin protein is formed, the lactoferrin protein is isolated.

In still yet another embodiment of the present invention, there is provided a recombinant expression vector. This vector comprises a transcriptional unit comprising an assembly of (1) a genetic element or elements having a regulatory role in gene expression; (2) cDNA coding for lactoferrin; (3) appropriate transcription and translation initiation and termination sequences; and (4) a genetic element for selection of transformed cells or spores such as Aspergillus spores that have been transformed with the vector.

In still yet another embodiment of the present invention, there is provided a method for producing biologically active recombinant lactoferrin. The method comprises synthesizing sequences containing a selectable marker gene, a promotor, a transcription termination sequence, and a linker sequence; cloning the sequences to form a plasmid; digesting the plasmid with a restriction endonuclease; inserting a cDNA coding for lactoferrin into a restriction site; and transforming eucaryotic cells with the plasmid expressing lactoferrin cDNA.

BRIEF DESCRIPTION OF THE DRAWINGS

So that the manner in which the above recited features, advantages, and objects of the invention, as well as others which will become clear, are obtained and can be understood in detail, more particular descriptions of the invention briefly summarized above may be had by reference to certain embodiments thereof which are illustrated in the appended drawings. These drawings form a part of this specification.

It is to be noted, however, that the appended drawings illustrate preferred embodiments of the invention and therefore not to be considered limiting of its scope. The invention may admit to other equally effective equivalent embodiments.

FIGS. 2A through 2D collectively depict the cDNA sequence (SEQ. ID No. 1) with deduced amino acids (SEQ. ID No. 2) for the human lactoferrin protein and signal peptide sequence.

FIGS. 8A through 8C collectively show the silver stained SDS-acrylimide gel analysis of recombinant LF secretion and purification.

FIGS. 14A through 14C collectively depict the (A) cDNA sequence (SEQ. ID No. 3) with (B) deduced amino acids (SEQ. ID No. 4) for the bovine lactoferrin protein.

FIGS. 15A through 15B collectively depict the (A) cDNA sequence (SEQ. ID No. 5) with (B) deduced amino acids (SEQ. ID No. 6) for the porcine lactoferrin protein.

FIGS. 18A through 18N collectively depict restriction enzyme cleavage sites for the human cDNA sequence.

FIGS. 19A through 19M collectively depict restriction enzyme cleavage sites for the bovine cDNA sequence.

FIGS. 20A through 20N collectively depict restriction enzyme cleavage sites for the porcine cDNA sequence.

DETAILED DESCRIPTION OF THE INVENTION

DEFINITIONS

Figure 1:
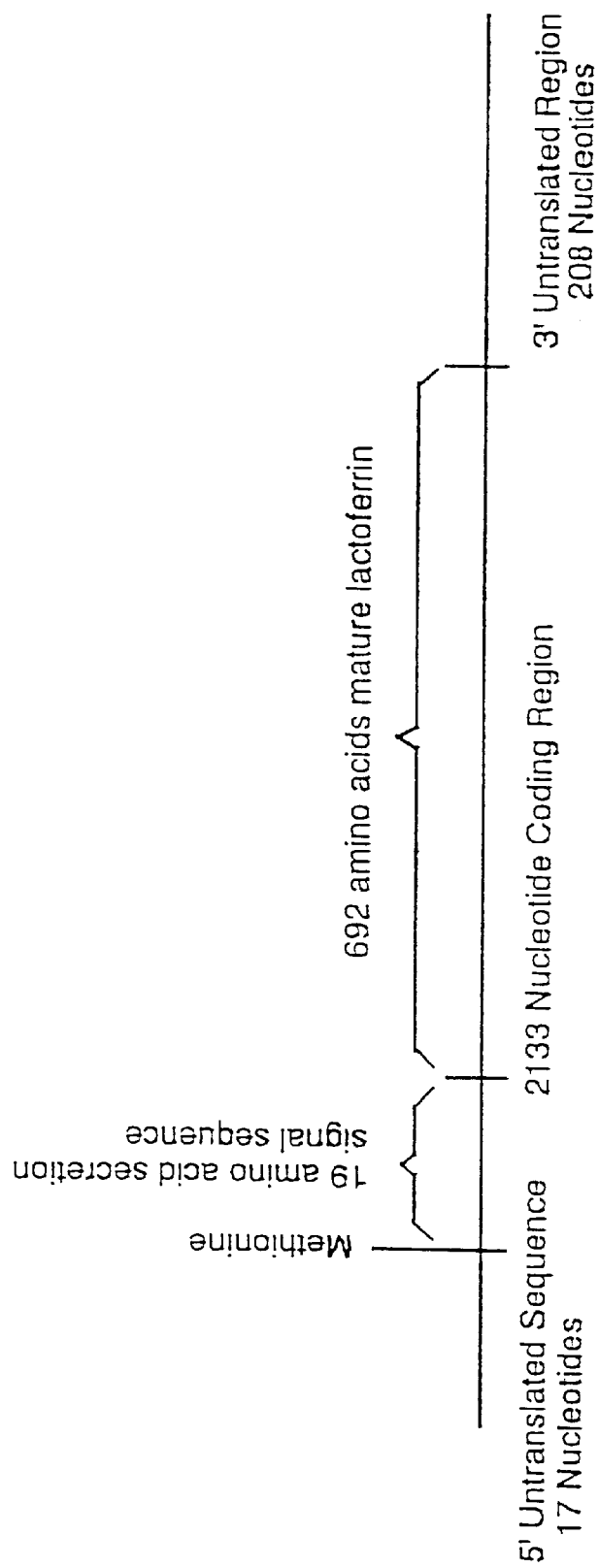
FIG. 1 is a schematic drawing of the hLF cDNA including the locations of the 5' untranslated region, the secretion peptide signal sequence, mature lactoferrin and 3' untranslated region.

For the purposes of the present application, the term "transferrin family" means a family of iron transferring proteins including serum transferrin, ovotransferrin and lactoferrin. These proteins are all structurally related.

For the purposes of the present application, the term "vector(s)" means plasmid, cosmid, phage or other vehicle to allow insertion, propagation and expression of lactoferrin cDNA.

For the purposes of the present application, the term "host(s)" means any cell that will allow lactoferrin expression.

For the purposes of the present application, the term "promotor(s)" means regulatory DNA sequences that controls transcription of the lactoferrin cDNA.

For the purposes of the present application, the term "multiple cloning cassette" means a DNA fragment containing restriction enzyme cleavage sites for a variety of enzymes allowing insertion of a variety of cDNAs.

For the purposes of the present application, the term "transformation" means incorporation permitting expression of heterologous DNA sequences by a cell.

For the purposes of the present application, the term "iron binding capacity" means ability to bind Fe. Fully functional human lactoferrin can bind two atoms of iron per molecule of LF.

For the purposes of the present application, the term "biological activity/biological active" means biological activity of lactoferrin as measured by its ability to bind iron, or kill microorganisms, or retard the growth of microorganisms, or to function as an iron transfer protein.

For the purposes of the present application, the term "substitution analog" referring to a DNA sequence means a DNA sequence in which one or more codons specifying one or more amino acids of lactoferrin or a lactoferrin polypeptide are replaced by alternate codons that specify the same amino acid sequence with a different DNA sequence. Where "substitution analog" refers to a protein or polypeptide it means the substitution of a small number, generally five or less, commonly 3 or 4, and more often 1 or 2 amino acids as are known to occur in allelic variation in human and other mammalian proteins wherein the biological activity of the protein is maintained. For example, hLF isolated from milk has been reported to differ from the hLF of SEQ. ID No. 2 at two amino acid residues.

The confirmation of the cDNA sequence and the deduced amino acid have been proven by multiple confirmation procedures. These are:
1. Multiple sequence analyses.
2. Comparison of the amino acid sequence deduced from the cDNA with that of hLF generated by conventional amino acid sequencing of hLF isolated from milk. The unique cDNA sequence which encodes the human lactoferrin protein has a variety of applications as known and indicated in the literature.
3. Transcription and translation of hLF protein from the cDNA with positive identification using an anti-hLF antibody.

The cDNA sequence of the present invention can be used to prepare recombinant human lactoferrin, thus making available a source of protein for therapeutic and nutritional applications. The confirmed cDNA of this invention can be used in an appropriate cloning vehicle to replicate the cDNA sequence. Also, the cDNA can be incorporated into a vector system for human lactoferrin expression. Other lactoferrin DNA sequences can be substituted for the human lactoferrin cDNA sequence to provide bovine, porcine, equine or other lactoferrins. Partial cDNA sequences can also be employed to give desired lactoferrin derived polypeptides. The expression systems of the invention can be used to provide lactoferrin derived polypeptides that are not available by enzymatic digestion of naturally occurring lactoferrin. The invention further provides an expression system for producing lactoferrin and lactoferrin related polypeptides in mammalian cell lines, other eucaryotic cells including yeast and fungal cells and procaryotic cells. The invention allows for the production of lactoferrin free of lactoperoxidase, lysozyme, or other proteins that are contaminants of lactoferrin isolated from milk or other natural products. This invention is not limited to any particular uses of the human cDNA sequence or production of lactoferrin of other species from the appropriate DNA sequences.

The recombinant LF being a protein derived by recombinant techniques can be used in a variety of applications. The human gene can be transferred to mammalian systems such as cows and other agriculturally important animals and expressed in milk. The incorporation of a human lactoferrin gene and expression in the milk of animals can combat an iron deficiency typical in piglets. The inclusion of the human lactoferrin gene with expression should improve an animal's disease resistance to bacterial and viral infection. The tissue specific expression of human lactoferrin in mammary glands, for instance, would impart the bacteriocidal and virucidal benefit of the expressed gene to young feeding on the milk and would provide a production means for the secreted protein for therapeutic use.

The gene can be placed in the appropriate cloning vector for the production of LF. The LF produced by recombinant methods can be used in a variety of products including human or animal foods, as therapeutic additives to enhance iron transport and delivery, and for the virucidal and bacteriocidal qualities, as additives for eyedrops, contact lens and other eye care solutions, topical skin care products, eardrops, mouthwashes, chewing gum and toothpaste. The recombinant LF would provide a safe, naturally occurring product which can be topically applied as well as ingested safely. The bactericidal lactoferrin polypeptides are useful as preservatives in the above listed products, and as therapeutic anti-infection agents. The iron binding polypeptides are useful as iron carrier proteins for nutritional and therapeutic uses, and as bacteriostats and bactericides, especially in products of the types listed above. Each protein may also be used as a nutrition supplement and as a source of amino acids.

The full-length cDNA encoding human lactoferrin has been isolated, and the analysis has been completed. The cDNA sequence has been confirmed as human lactoferrin cDNA by comparison of the deduced amino acid sequence with the published amino acid sequence of hLF. The expression of lactoferrin was observed in a eucaryotic expression system from the cDNA and a plasmid vector. The presence of lactoferrin was confirmed by standard Western immunoblot analysis using anti-human lactoferrin antibodies and relative molecular mass measurement.

FIG. 1 is a schematic of the lactoferrin cDNA. The sequence can generally be described as an initial 5' untranslated region, 17 nucleotides in length. The next portion is 57 nucleotides which codes for the 19 amino acid secretion signal peptide starting with methionine. The next sequence of the cDNA codes for the mature human lactoferrin protein of 692 amino acids followed by the 3' untranslated region of 208 nucleotides which ends the cDNA. The complete sequence is 2,358 nucleotides in length. The hLF protein contains glycosylation sites. The hLF protein with secretion signal sequence has an expected molecular mass of 78,403 daltons and the mature hLF is 76,386 daltons without added carbohydrate from glycosylation.

FIGS. 2A through 2D collectively depict the cDNA sequence (SEQ ID No. 1) with the deduced amino acids (SEQ ID No. 2) for the secretion signal peptide and the mature human lactoferrin protein. The numbers on FIGS. 2A through 2D collectively depict correspond to the nucleotides starting at the 5' end. There are binding sites for two iron atoms with four amino acids participating in the binding of each iron. The amino acids at positions Asp80, Tyr112, Tyr209, and His273 are required for coordination with one iron, and amino acids at positions Asp415, Tyr455, Tyr548, and His617 bind the other. There are two glycosylation sites at positions Asn157 and Asn498. The numbers refer to the deduced amino acid sequence. There are 25 amino acids per line of protein sequence (starting at nucleotide 18).

The nucleotide sequence analysis was performed on cDNA isolated from a human prostate cDNA library. The prostate cDNA library yielded a 2,140 bp cDNA which contained the complete 5' end including the untranslated portion and the signal sequence. The 3' end including the three amino acids at the carboxy terminal and the untranslated region were obtained as a 208 bp cDNA from both a monocyte cDNA library and human prostate cDNA library.

The data in FIGS. 2A through 2D collectively depict displays the full length cDNA sequence of this invention. The complete sequence including the 5' untranslated region and signal peptide have not been reported. Further, the previously reported amino acid sequence varies from the deduced amino acid sequence for hLF of this invention. The following TABLE 1 is a summary of the differences of the amino acid sequence of the present invention and those reported by Metz-Boutigue et al., *Eur. J. Biochem.*, vol. 145, pp. 659–76 (1984). For the purpose of this table, the numbering of the amino acids will be initiated with methionine at the start of the signal peptide sequence as amino acid #1.

TABLE 1

COMPARISON OF AMINO ACID SEQUENCES
HUMAN LACTOFERRIN

| Amino Acid Deduced from cDNA of hLF | Change | Metz-Boutigue Sequence |
|---|---|---|
| # 30 Thr | Substitution | Ala |
| # 48 Arg | Substitution | Lys |
| # 141 Arg | Insertion | NONE |
| # 170 Ala | Insertion | NONE |
| # 204 Ser | Substitution | Leu |
| # 206 Gln | Substitution | Lys |
| # 209 Tyr | Substitution | Lys |
| # 386 Glu | Substitution | Gln |
| # 392 Ser | Substitution | Trp |
| # 410 Asp | Substitution | Asn |
| # 411-424 | Deletion | 13 Amino acids in protein sequence not in deduced amino acid sequence from cDNA |
| # 532 Gln | Substitution | Glu |
| # 695 Lys | Substitution | Arg |

Figure 3:
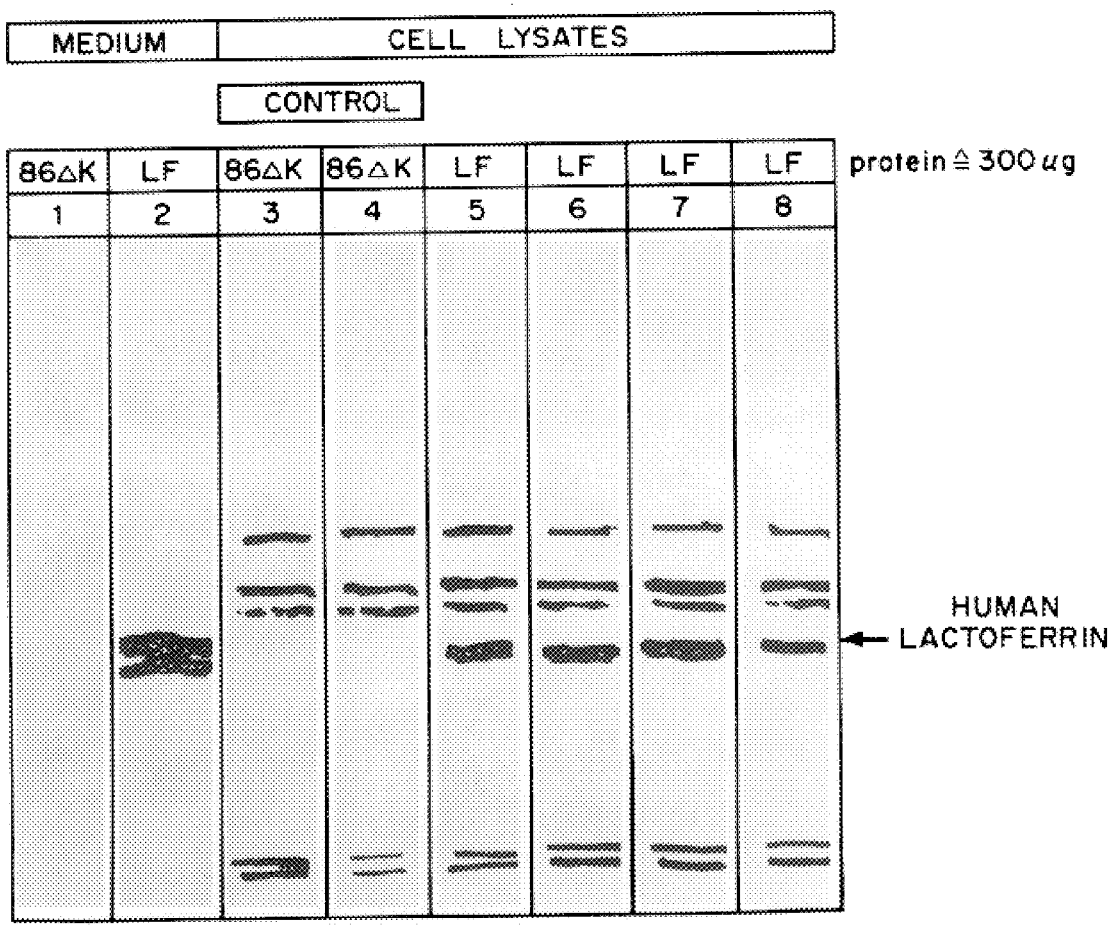
FIG. 3 is a schematic representation of an autoradiograph of recombinant human lactoferrin protein expressed from the complete cDNA.

FIG. 3 is the expression of human lactoferrin protein from the complete hLF cDNA. In addition to using the entire cDNA sequence and deduced amino acid sequence, a polypeptide of less than the entire protein can be of value. For instance, the region between amino acids 74–275 contains an iron binding domain which may be used without the rest of the protein for biologically available iron or the bacteriostatic qualities.

The cDNA sequence has been confirmed to encode lactoferrin. The hLF cDNA was shown to encode lactoferrin by expression of the cDNA in a eucaryotic expression system and detection of the expressed lactoferrin protein by Western immunoblot analysis using specific lactoferrin antibodies.

Recombinant production of lactoferrin protein has been described below in its preferred embodiments. However, it is also produced in a number of other sources such as fungal sources such as *Saccharomyces cerevisiae, Kluyveromyces lactis*, or *Pichia pastorsis*, or insect cells such as SF9, or bacterial cells such as *Escherichia coli*, or *Bacillus subtilis*.

In one embodiment of the present invention, biologically active recombinant lactoferrin protein is produced. This method comprises synthesizing sequences containing a selectable marker gene, a promotor, a transcription termination sequence and a linker sequence.

Subsequently, the sequences are cloned to form a plasmid and the plasmid is digested with a restriction endonuclease. A cDNA coding for lactoferrin is inserted into a restriction site and eucaryotic cells are then transformed with the plasmid expressing the lactoferrin cDNA.

The selectable marker gene useful in the method of the present invention may be any that permits isolation of cells transformed with a lactoferrin cDNA plasmid. Preferably, the selectable marker gene is selected from pyr4, pyrG, argB, trpC and andS.

The promotor useful in the present invention may be any that allows regulation of the transcription of the lactoferrin cDNA. Preferably, the promotor is selected from the group of alcohol dehydrogenase, argB, α-amylase and glucoamylase genes.

The transcription termination sequence useful in the present method may be any that allows stabilization of the lactoferrin mRNA. Preferably, the transcription termination sequence is derived from the α-amylase, glucoamylase, alcohol dehydrogenase or benA genes.

The linker sequence useful in the present method may be any that contains a translation initiation codon, a secretory signal and a restriction enzyme cleavage site. Preferably, the linker element is derived from the α-amylase or glucoamylase genes.

The cells, preferably eucaryotic cells, useful in the present invention are any that allow for integration of a vector, preferably a plasmid comprising the lactoferrin cDNA and expression of the lactoferrin cDNA. Preferably, the eucaryotic cells are fungal cells or insect cells. Insect cells such as SF9 are useful in the method of the present invention. More preferably, the fungal cells are yeast cells or Aspergillus. Most preferably, the eucaryotic cells useful in the present invention are Aspergillus strains, such as *A. oryzae, A. niger, A. nidulans* and *A. awamori*.

The invention also comprises partial sequences of the cDNA of SEQ ID No. 1, 3 and 5 and substitution analogs thereof which code for biologically active polypeptides having homology with a portion of lactoferrin, especially those that are not available from enzyme digests of natural lactoferrins, the method of making polypeptides by use and expression of partial cDNA sequences, and the polypeptide products produced by the methods of this invention. The desired partial sequences can be produced by restriction enzyme cleavage, as for example at the cleavage sites indicated in FIGS. 18A through 18N, 19A through 19M, and 20A through 20N, the partial sequences may also be synthesized or obtained by a combination of cleavage, ligation and synthesis, or by other methods known to those skilled in the art.

Recombinant production of lactoferrin protein and polypeptides has been described in its preferred embodiment. However, it is also produced in a number of other sources such as fungal sources such as *Saccharonzyces cerevisiae, Kluyveronzyces lactis*, or *Pichia pastorsis* or insect cells such as SF9, and lactoferrin polypeptides may also be produced in bacterial cells such as *Escherichia coli*, or *Bacillus subtilis*.

The following examples are given for the purposes of illustrating various embodiments of the present invention and are not meant to be limitations of the present invention in any form.

EXAMPLE 1

HUMAN LACTOFERRIN cDNA

The complete 2,358 bp hLF cDNA was ligated to the eucaryotic expression vector, p91023(B) at the EcoRI site downstream from the adenovirus major late promoter. This plasmid vector was provided by Genetics Institute (Cambridge, Mass.) and has been described in previous publications (Wong et al., Science 288:810–815 (1985)). The hLF cDNA expression vector was transferred into COSM-6 monkey kidney cells using standard tissue culture transfection conditions (Wigler et al., Cell, 16:777–785 (1979)). These COS cells do not normally express lactoferrin. Forty-eight hours after transfection, the cells were harvested and crude cell extracts were prepared. Positive identification of the human lactoferrin was made by standard Western immunoblot analysis of the proteins expressed in the cell extracts, as well as those secreted into the cell growth medium using a commercially available antibody directed against human lactoferrin (Sigma). Proteins which bound to the anti-lactoferrin antibody were detected using radio-iodine labelled Protein A which reacts with the antibody. The immunoblots were autoradiographed to identify the human lactoferrin protein. FIG. 3 is an autoradiographic film showing the human lactoferrin expressed in four cell extracts prepared from tissue culture cells which were transfected with the lactoferrin cDNA expression vector (lanes 5 to 8). Lanes 5 to 8 show that the transfected cells all contain human lactoferrin (marked with an arrow) which is immunoreactive with the anti-lactoferrin antibody and is the same molecular weight as human lactoferrin ($M_r$=78,403 daltons). The control cells which were not transfected with the cDNA did not contain lactoferrin (lanes 3 and 4). Analysis of the growth medium showed that human lactoferrin was also secreted into the medium from transfected cells (lane 2) but not from control cells (lane 1).

The cDNA encodes a recombinant human lactoferrin protein which is similar to human lactoferrin protein isolated from milk as determined by molecular size comparisons and immunoreactivity with anti-human lactoferrin. Furthermore, the secretion signal peptide sequence is functional since the human lactoferrin is secreted into the growth medium of tissue culture cells which express the cDNA.

Figure 4:
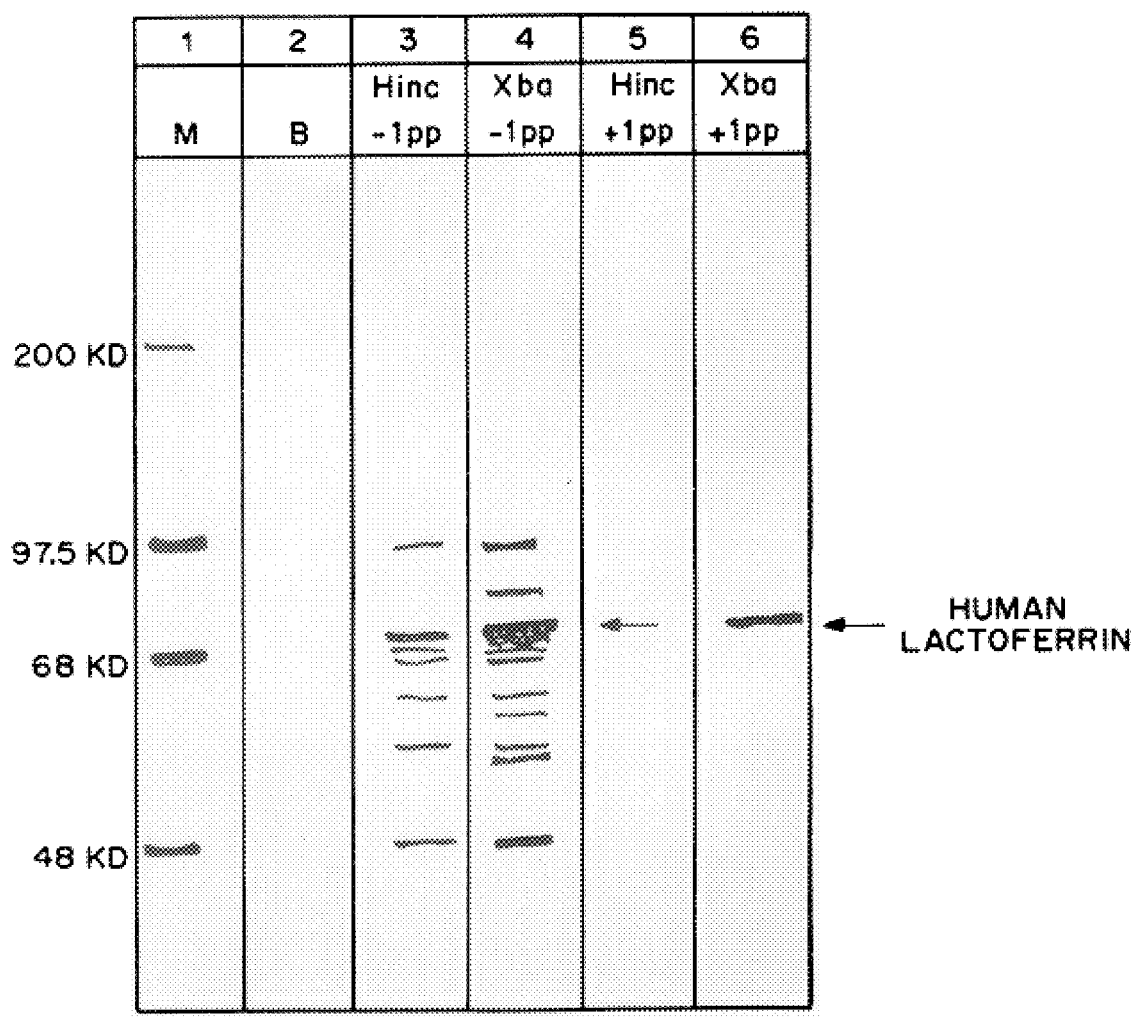
FIG. 4 is a schematic representation of an autoradiograph of the results of in vitro translation of a 2,140 bp human lactoferrin sequence and hLF protein in reticulocyte lysates.

FIG. 4 is a schematic representation of the human lactoferrin protein precipitated after in vitro transcription and translation of the human lactoferrin cDNA. The 2140 bp cDNA was from the human prostate cDNA library and included the 5' untranslated region and the rest of the base pairs correlative to the cDNA sequence of FIGS. 2A through 2D omitting the last 208 bp at the 3' terminus. The 2140 bp cDNA was ligated to the EcoRI site of the plasmid vector pGEM$_4$ (commercially available from Promega Biotech., Madison, Wis. 53711-5305) downstream from the SP$_6$ promoter. The plasmid construct was linearized at the 3' end of the hLF cDNA using the restriction enzyme Hinc II or Xba I. The linear DNA template was then transcribed in vitro using purified SP$_6$ RNA polymerase in the presence of ribonucleotides as described in the manufacturers protocol (Promega Corporation 1988/1989 Catalogue and Applications Guide). The resultant mRNA was translated using 100 ng mRNA template and micrococcal nuclease treated rabbit reticulocyte lysate (as described by Promega) in the presence of 75 uCi$^{35}$S methionine (800 ci/mmol, Amersham). In vitro synthesized lactoferrin was immunoprecipitated by incubating 100 ul aliquots of translation reaction with 10 ug of rabbit anti-human lactoferrin IgG (Sigma Chemical Company, St. Louis, Mo. 63178) for 2 hours at 4° C. in 50 mM Tris, pH7.5/0.15M NaCl/0.05% Tween-20 (1P buffer). The reaction volume was 200 ul. Immunoreactive lactoferrin was precipitated after incubation for 1 hour with 50 ug of Protein A sepharose (Pharmacia, Upsalla, Sweden). Immunoprecipitation was carried out by centrifugation for 5 minutes at 10,000 g and the precipitate was 5 washed 5 times with 4 volumes of 1P buffer. Total translation products and immunoprecipitates were then subjected to electrophoresis in denaturing 7.5% polyacrylamide gels. After fixing in 50% methanol, the gels were incubated in En$^3$Hance (NEN, DuPont, Wilmington, Del. 19801) for 1 hour and washed with distilled $H_2O$. The gel was then dried under vacuum and exposed to Kodak X-OMAT XAR film at –70° C.

Lane 1 shows $^{14}$C protein molecular weight markers used to estimate the size of the translated proteins. Lane 2 is a negative control which shows that no $^{35}$S labelled proteins are translated in this system when no mRNA is added to the translation mix. Lanes 3 and 4 show the total translation products obtained when lactoferrin mRNA is added after preparation from two separate DNA templates. The major protein band (marked with an arrow) is human lactoferrin. This is the only band detected when the translation products are imunoprecipitated with anti-human lactoferrin before applying the protein to the gel (lane 6). The measurement of molecular mass by SDS-PAGE does not correspond to exact molecular weight due to secondary protein structure. However, the values are shifted in a correlative manner in comparison to the control. Analysis of the size of the translated lactoferrin is shown in FIG. 4. The protein migrated at the expected molecular mass of human lactoferrin (about 78 Kd). The major bands in lanes 3 and 4 which migrate higher than the 68 Kd marker band in the control lane correspond to expected molecular mass of hLF protein on SDS-PAGE.

EXAMPLE 2

FUNGAL STRAINS AND TRANSFORMATION

The pyrG mutant strain used in these studies was derived from A. oryzae (A07 11488). The pyrG gene from A. oryzae was mutated with 4-nitroquinoline-1-oxide. The Aspergillus transformation was carried out by a modification of the procedure of Osmani, et al., J. Cell. Biol. 104:1495–1504 (1987). Conidia (1×10$^6$/ml) were inoculated into 50 ml of YG medium (0.5% yeast extract 2% glucose) containing 5 mM uracil and 10 mM uridine. Growth was at 32° C. for 14–16 hours until a germ tube was visible. The germinated conidia were harvested by centrifugation and resuspended in 40 ml of lytic mix containing 0.4 M ammonium sulphate, 50 mM potassium citrate (pH 6.0), 0.5% yeast extract, 0.12 g novozyme, 0.1 g Driselase, 100 μl β-glucuronidase, 0.5% sucrose and 10 mM MgSO$_4$. Protoplasting was for 2–3 hours at 32° C. and 150 rpm. Following protoplasting, filtration using sterile miracloth was necessary to remove any undigested mycelia. The protoplasts were harvested by centrifugation and washed twice with 10 ml of 0.4 M ammonium sulphate, 1% sucrose and 50 mM potassium citrate (pH 6.0) at 4° C., resuspended in 1 ml of 0.6 M KCl; 50 mM CaCl; 10 mM Tris-HCl (pH 7.5) and placed on ice. The transformation was performed immediately following the protoplast preparation. Aliquots (100 μl) of the protoplast were added to 3 μg of DNA and 50 μl of 40% polyethylene glycol (PEG) 6000, 50 mM CaCl$_2$, 0.6 M KCl and 10 mM Tris-HCl, (pH 7.5). The samples were incubated on ice for fifteen minutes after which an additional 1 ml of the PEG solution was added and incubation at room temperature was continued for thirty minutes. Aliquots of this mixture were plated in 3 mls of 0.7% minimal media, supplemented with 0.4% ammonium sulphate onto plates containing the same but solidified with 2% agar. All subsequent growth was at 32° C.

EXAMPLE 3

PLASMID CONSTRUCTION

Figure 5:
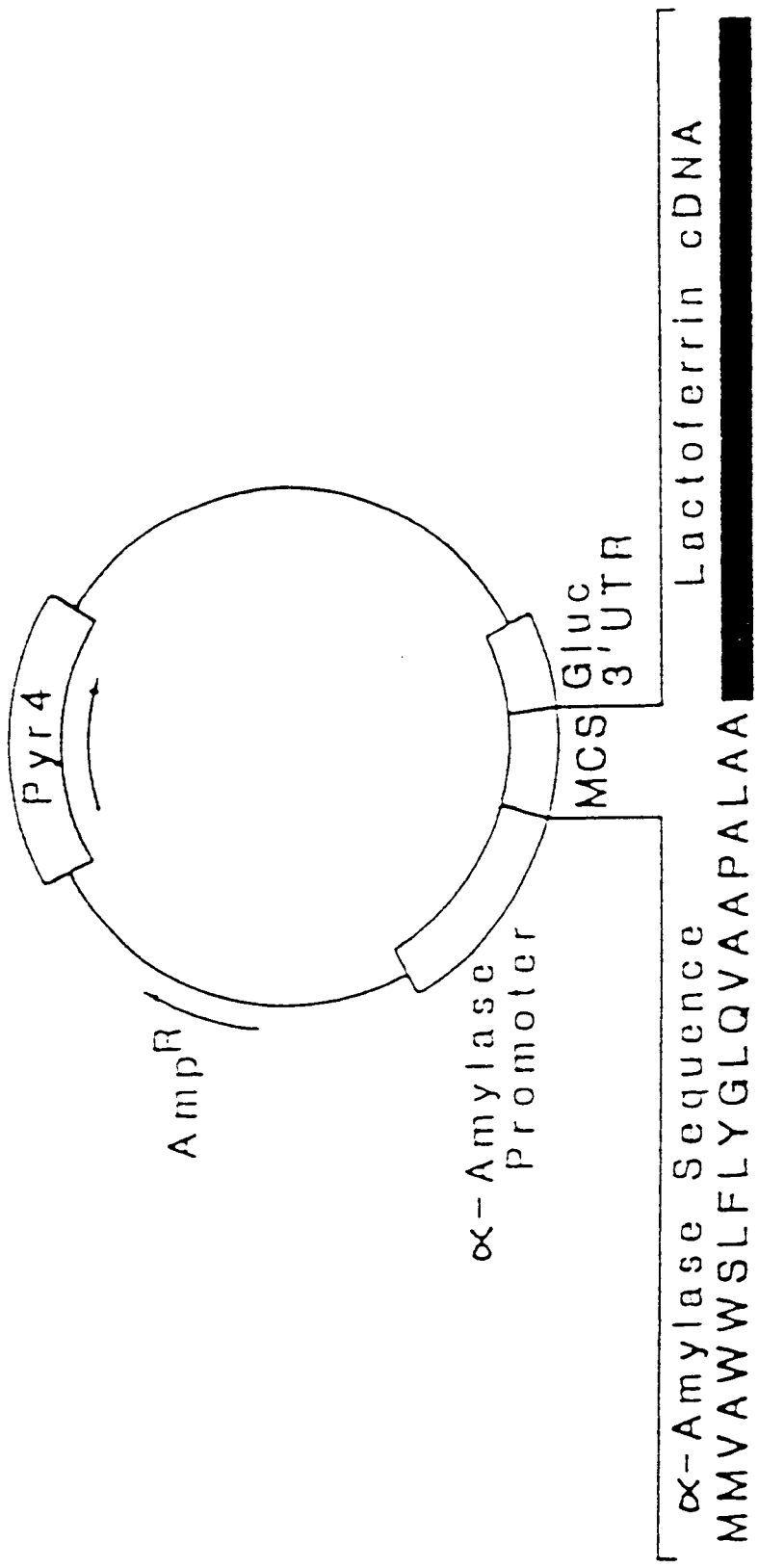
FIG. 5 depicts a schematic representation of the *Aspergillus oryzae* expression plasmid, pAhlfg.

A schematic representation of the expression plasmid is shown in FIG. 5. The complete cDNA encoding human LF was repaired using the Kienow fragment of DNA polymerase I and subcloned into Acc I digested and repaired pGEM4 to generate pGEMhLFc. In order to remove the LF signal sequence and generate a 5' end in frame with the α-amylase sequences, a 252 base pair lactoferrin fragment (nt 69–321) containing Hind II/Acc I ends was obtained by polymerase chain reaction (PCR) amplification of pGEM-hLFc plasmid DNA. The oligo primers used were as follows: the 5' end oligonucleotide as shown in SEQ. ID. No. 7:

(CTGGGTCGACGTAGGAGAAGGAGTGTTCAGTGGTGC)

and the 3' end oligonucleotide as shown in SEQ. ID. No. 8:

(GCCGTAGACTTCCGCCGCTACAGG).

This PCR fragment was digested with Hind II and Acc I and was subcloned into Hind II/Acc I digested pGEMhLFc generating pGEMhLF. A 681 base pair α-amylase fragment with Asp718/Pvu II ends encoding the promotor, signal sequence and the alanine residue from the start of the mature α-amylase II gene, was obtained by PCR amplification of *A. oryzae* genomic DNA. The oligo primers were as follows: the 5' end oligonucleotide as shown in SEQ. ID. No. 9:

(GAGGTACCGAATTCATGGTGTTTTGATCATTTTAAATTTTTATAT)

and the 3' end oligonucleotide as shown in SEQ. ID. No. 10:

(AGCAGCTGCAGCCAAAGCAGGTGCCGCGACCTGAAGGCCGTACAG).

The amplified DNA was digested with Asp718 and Pvu II and subcloned into Asp718/Hind II digested pGEMhLF. The resulting plasmid (pGEMAhLF) was digested with EcoR I and the resulting 2.8 kb α-amylase-lactoferrin fragment was subcloned into a unique EcoR I site in pAL3 according to the method of generating pAhLF*. Synthetic oligonucleotides were used to provide the last five carboxy terminal codons of lactoferrin (nt 2138–2153) missing in pAhLF* and also to provide the first 180 bp of 3' untranslated sequences from the *A. niger* glucoamylase gene. The resulting plasmid (pAhLFG) was used to transform the *A. oryzae* pyrG mutant strain.

With reference to FIG. 5, *Aspergillus oryzae* expression plasmid, pAhLFG contains 681 bp of 5'-flanking sequence of the *A. oryzae* AMY II gene which includes the signal sequence and first codon of mature α-amylase. The cDNA coding for mature human lactoferrin is subcloned in frame downstream from these sequences allowing recombinant protein production by the addition of starch to the growth medium. The *Aspergillus niger* glucoamylase 3' untranslated region provides the transcription terminator and polyadenylation signals. The plasmid also contains the *Neurospora crassa* pyr4 selectable marker and an ampicillin resistance gene.

The plasmid construct (pAhLFG) used for expression of human LF contains a 681 bp fragment that encodes the promotor and secretory signal peptide of the *A. oryzae* α-amylase II gene (AMY II). The signal sequence also contains the codon for alanine from the start of the α-amylase mature protein generating the signal sequence cleavage site (Leu Ala) recognizable by an endogenase α-amylase peptidase. A human lactoferrin cDNA fragment encoding the mature protein was subcloned in frame immediately downstream from the AMY II sequences, placing it under the control of this highly efficient starch inducible promoter. In order to stabilize the transcribed human LF mRNA, a 180 bp fragment encoding the 3' untranslated region of the glucoamylase gene from *Aspergillus niger* was ligated into a unique BamH I site in the multiple cloning cassette, immediately downstream of the human LF cDNA providing the transcription terminator and polyadenylation signals. The plasmid also contains the *Neurospora crassa* pyr4 selectable marker which complements a pyrG auxotrophic mutation of *A. oryzae* and allows for selection of spores that have been transformed with the plasmid by growth in the absence of uridine.

EXAMPLE 4

GENOMIC DNA MANIPULATION

*A. oryzae* DNA was isolated from 200 mg of lyophilized mycelia as described by Rasmussen, et al., *J. Biol. Chem.*, 265:13767–13775 (1990). The DNA was digested with EcoR I, size fractionated on a 0.8% agarose gel and transferred to nitrocellulose. Prehybridization and hybridization of the nitrocellulose filter for Southern analysis were performed in 6×SSC, 0.1% SDS and 0.5% dried milk at 65° C. for 16 hours. Hybridization solution contained $1 \times 10^7$ cpm $^{32}$P-labelled lactoferrin cDNA probe (2.1 Kb). The filter was washed in 2×SSC, 0.5% SDS at room temperature for 30 minutes followed by two washes in 0.5×SSC, 0.5% SDS at 68° C. for 30 minutes. The filter was dried, exposed at -70° C. for two hours and developed by autoradiography.

Figure 6:
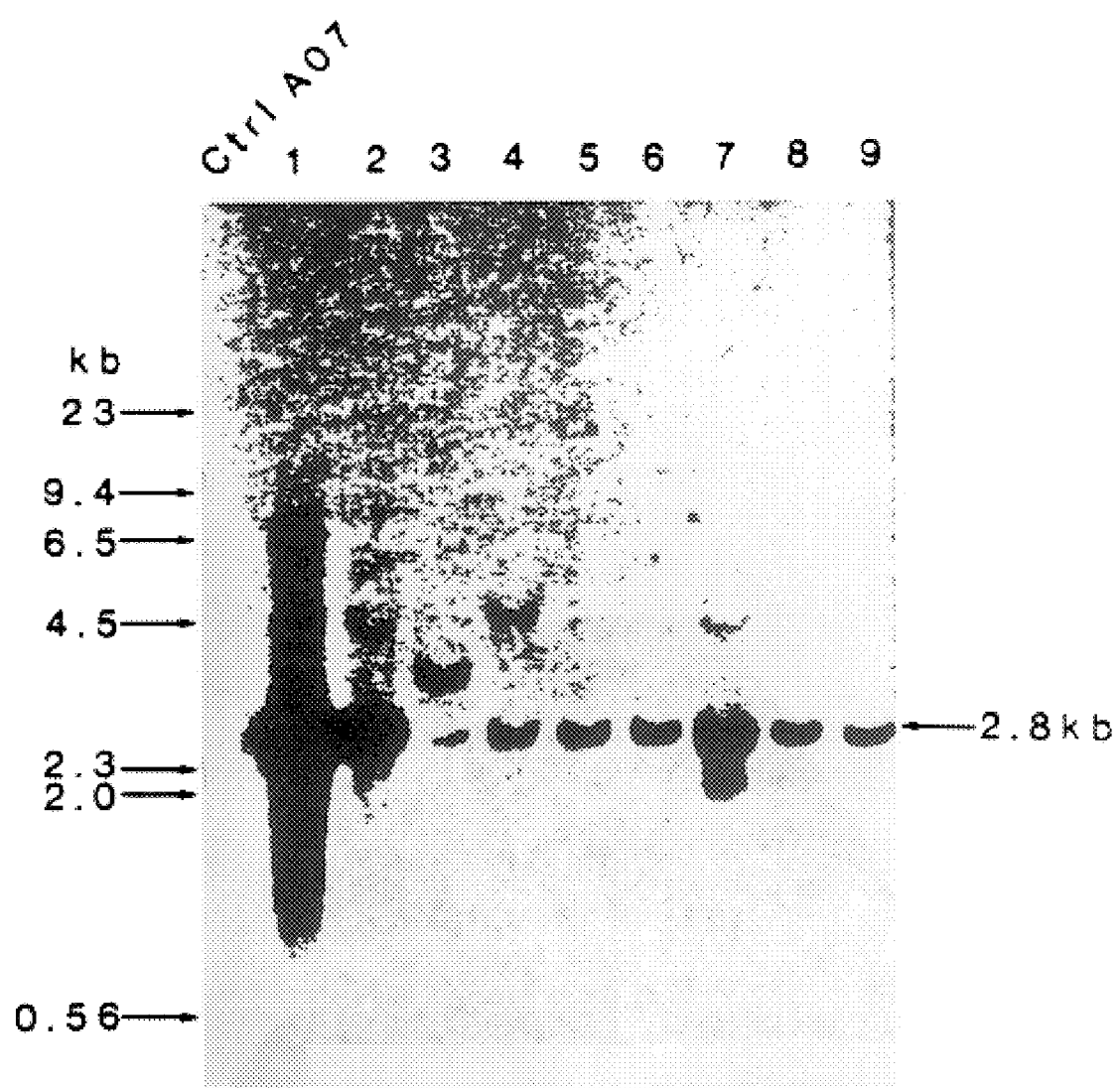
FIG. 6 shows a southern blot analysis of transformed *Aspergillus oryzae* strains.

With reference to FIG. 6, Southern blot analysis was performed on transformed *Aspergillus oryzae* strains. Genomic DNA from individual transformants and control AO7 were hybridized with a radiolabelled hLF cDNA probe (2.1 kb). The arrow points to a radiolabelled fragment (2.8 kb) generated upon EcoR I digestion of the expression plasmid which is present in all the transformants (#1–9) but is absent in control untransformed AO7. Molecular weights of bacteriophage lambda Hind III fragments are indicated at the left.

EXAMPLE 6

NORTHERN ANALYSIS

RNA was isolated from lyophilized mycelia (200 mg) using commercially available RNazol B (Biotecx Laboratories, INC, Houston, Tex.) according to the manufacturers instructions. Total RNA (20 μg) was electrophoresed in a 0.8% agarose gel containing 2.2 M formaldehyde. The RNA was transferred to nitrocellulose and hybridized with either a 2.1 kb lactoferrin cDNA or a 1.8 kb genomic α-amylase fragment corresponding to the coding region of the α-amylase II gene. The probes were $^{32}$P-labelled by nick translation (specific activity $2 \times 10^8$ cpm/ug). Hybridization was carried out 2×SSC, 0.05% dried milk at 65° C. over an ice with $2 \times 10^6$ cpm probe/ml.

Washes were identical to those employed in the Southern analysis. The filters were dried, exposed at -70° C. for two hours and developed by autoradiography. RNA dot blots were performed using nitrocellulose membrane and the manifold dot blot system. Hybridization and washing conditions were as described above for Southern analysis. Radioactivity was quantitated using the betagon blot analyzer.

Figure 7A:
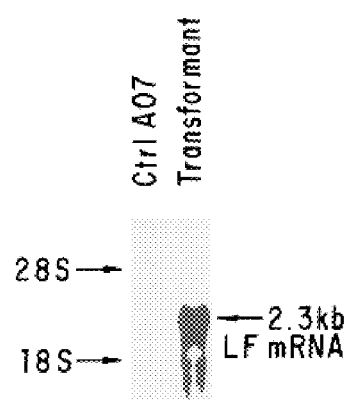
FIGS. 7A through 7C collectively depict an RNA analysis of transformant versus control A07.
Figure 7B:
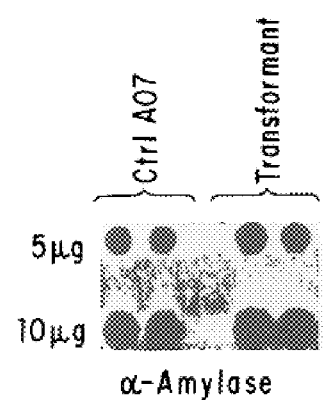
Figure 7C:
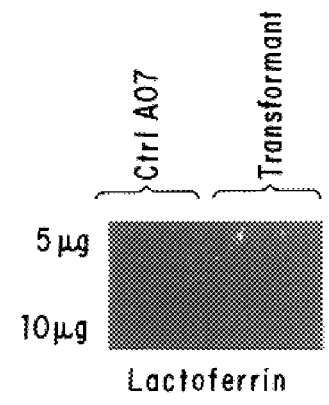

With reference to FIGS. 7A through 7C, RNA analysis of transformant versus control AO7 was performed. In Panel A, Northern analysis of RNA (20 μg) from control AO7 and transformant #1 were hybridized with radiolabelled human LF cDNA. Human LF mRNA (2.3 kb) was detected in the transformant #1 but not in the control untransformed AO7. The positions of the 28S and 18S rRNA bands are indicated on the left. In Panel B, Dot blots of RNA (5 and 10 μg) from control AO7 versus transformant #1 using a radiolabelled α-amylase genomic DNA probe. In Panel C, Dot blots of RNA (5 and 10 μg) from control AO7 and transformant #1 using radiolabelled human LF cDNA probe as illustrated.

Northern analysis was performed to determine if lactoferrin mRNA was transcribed correctly and efficiently in *A. oryzae* under the regulatory control elements of the expression plasmid. Spores ($1 \times 10^6$/ml) from transformant #1 and from control untransformed spores were inoculated into fungal medium containing 1.5% glucose as carbon source and grown at 30° C. for 48 hours in small shake flask cultures. The cultures were washed and reinoculated into fungal medium containing 3% starch to induce transcription of the human LF mRNA. After 24 hours, the cells were harvested and RNA was isolated. Total RNA (20 μg) was size fractionated on a 1.0% agarose gel containing 2.2 M formaldehyde and blotted on nitrocellulose.

Human lactoferrin mRNA was detected using $^{32}$p labelled human LF cDNA (2.0 kb) probe. Hybridization with human LF radiolabelled cDNA probe detected a specific radiolabelled band at the correct size for lactoferrin mRNA (2.3 kb) in the transformant but not in the control untransformed strain (FIG. 7A). Quantitation of mRNA levels by dot assay showed comparable levels of expression of endogenous α-amylase rRNA between control AO7 and transformant #1 (FIG. 7B). In addition, similar levels of expression of α-amylase and human LF mRNA were seen in transformant #1 (FIGS. 7B and 7C).

EXAMPLE 6

PURIFICATION OF RECOMBINANT HUMAN LF

LF was purified from the growth medium using CM Sephadex C50 essentially as described by Stowell, et al., *Biochem J.*, 276:349–59 (1991). The column was pre-equilibrated with 500 ml of 0.025 M Tris HCl, pH 7.50 1M NaCl. The pH of the culture medium was adjusted to pH 7.4 before applying to the pre-equilibrated column. The column was washed with 500 ml of equilibration buffer and followed by a linear salt gradient from 0.1 to 1.1 M NaCl. Fractions (7 ml total) were assayed for lactoferrin content and purity using SDS/PAGE and silver staining. Fractions containing LF were dialyzed against 0.025 M Tris HCl, pH 7.5/0.1M NaCl and lyophilized.

EXAMPLE 7

QUANTITATION OF HUMAN LF

Recombinant lactoferrin was quantitated using an ELISA assay essentially as described by Vilja et al., *J. Immunol. Methods*, 76:73–83 (1985). A sensitivity of 5 ng of lactoferrin was obtained using the non-competitive Avidin-biotin assay. Human LF isolated from breast milk (Sigma) was used as standard. Biotinylated human lactoferrin IgG was obtained from Jackson Immunoresearch laboratories, West Grove, Pa.

EXAMPLE 8

N-TERMINAL SEQUENCING

Five μg of purified recombinant human LF was resolved on an SDS-polyacrylamide gel and transferred to Problott, a polyvinylidene difluride-type membrane, following manufacturers instructions (Applied Biosystems). Human LF was detected with Comassie Brilliant Blue staining and destained. This human LF band was excised, washed thoroughly with distilled $H_2O$ and air-dried. The N-terminal amino acid sequence of the first ten amino acids of human LF was determined by the automated Edman degradation procedure using an applied Biosystems Pulsed-liquid phase sequencer (Model 477A).

Figure 8A:
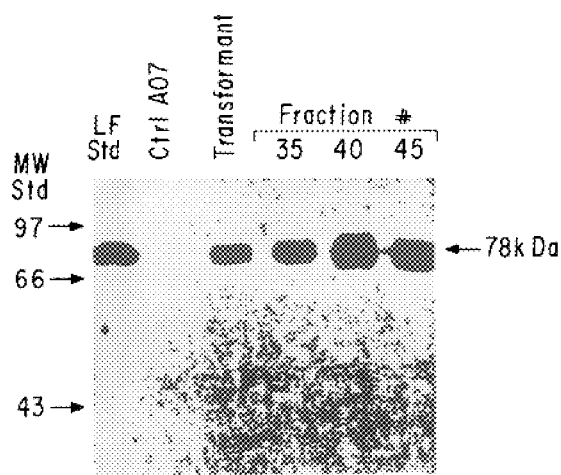
Figure 8B:
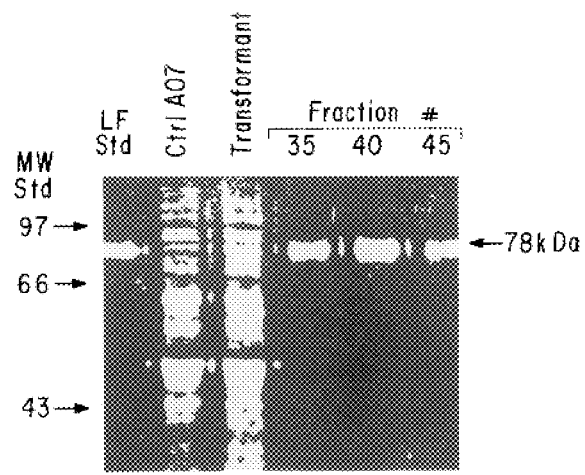

With reference to FIGS. 8A through 8B, panel A illustrates a Silver stained SDS-polyacrylamide gel analysis of recombinant human LF secretion and purification. Lane 1 contains breast milk human LF standard (500 ng). Lanes 2 and 3 contain samples of the growth medium (40 μg) from induced control AO7 and transformant #1 respectively. Lanes 4–8 contain 100 μl aliquots of eluted fractions (#25, 30, 35, 40, and 45 respectively) collected from the CM-sephadex purification of recombinant LF from the growth medium of transformant #1. The position of the molecular weight markers (BioRad Richmond, Calif.) are indicated on the left. Sizes are given in kilo Daltons. Panel B illustrates a Western immunoblot analysis of duplicate samples as described in panel A using a specific polyclonal antibody directed against human LF with detection with $^{125}$I-protein A. Panel C illustrates #6 N-terminal amino acid sequence of recombinant human LF. Recombinant human LF was sequenced from the N-terminus through 10 residues and is identical to breast milk human LF with the exception of the additional alanine generated in our construction to provide the α-amylase signal sequence cleavage site.

EXAMPLE 9

DEGLYCOSYLATION

Deglycosylation was performed using N-glycosidase F (Boehringer Mannheim). *A. oryzae* growth medium containing 0.5 μg lactoferrin was denatured for 3 minutes at 100° C. in the presence of 0.01% SDS. Standard LF from human milk was treated similarly. The samples were subsequently placed on ice for five minutes. N-glycosidase F reactions were conducted in 0.4 M sodium phosphate, (pH 6.8); 0.08% Triton; 0.1% β-mercaptoethanol and 1 unit of enzyme and incubated at 37° C. for sixteen hours. PAGE and Western analysis was performed using an IgG specifically directed against human lactoferrin to detect an increase in mobility of digested samples.

Figure 9A:
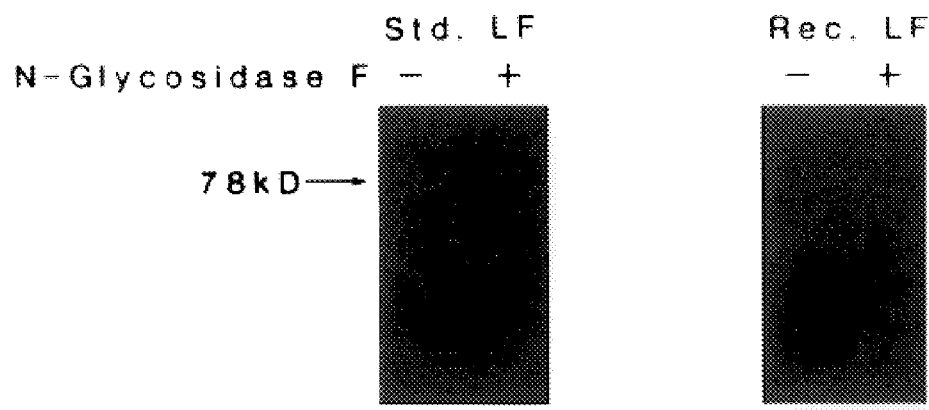
FIGS. 9A through 9B collectively illustrate the characterization of recombinant human LF.
Figure 9B:
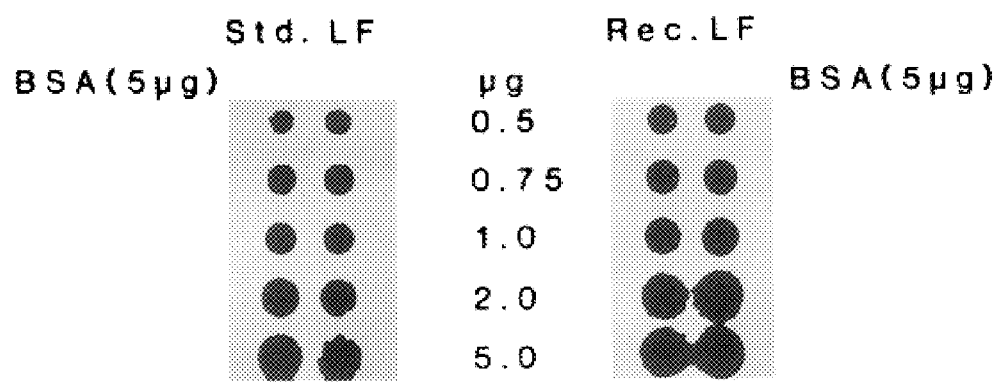

With reference to FIGS. 9A through 9B, recombinant human LF was characterized. Panel A illustrates the deglycosylation of lactoferrin. Western analysis of glycosylated and deglycosylated lactoferrin using a specific polyclonal antibody was directed against human lactoferrin with detection with $^{125}$I-protein A. The first panel contains authentic breast milk human LF (500 ng) untreated (−) and treated (+) with N-glycosidase F. The second panel contains purified recombinant human LF (500 ng) untreated (−) and treated (+) with N-glycosidase F. The size of glycosylated human LF is indicated with the arrow. Panel B illustrates a functional analysis of recombinant lactoferrin with regard to iron-binding capacity. Panel A and B show the $^{59}$Fe filter binding assay of duplicate samples of authentic breast milk human LF and purified recombinant human LF, respectively, at the concentrations indicated. The first lane in both panels contain BSA (5 μg) as a negative control.

Lactoferrin contains two N-acetyllactamine type glycans attached through N-glycosidic linkages. To determine if recombinant lactoferrin was glycosylated correctly, the protein was treated with N-glycosidase F, resolved on SDS-polyacrylamide electrophoresis, transferred to nitrocellulose and probed using a specific IgG directed against human lactoferrin (FIG. 11A). N-glycosidase F hydrolyses at the glycosylamine linkage generating a carbohydrate free peptide of smaller molecular weight. Comparison of recombinant LF with purified LF from human milk, illustrates that both proteins co-migrate upon digestion with N-glycosidase F suggesting that the recombinant protein has a glycosylation pattern similar to native LF.

Lactoferrin has a bilobal structure with each lobe having the capacity to bind tightly, but reversibly, one $Fe^{3+}$ion. The iron-binding properties of lactoferrin are crucial for its functional roles. To test if recombinant human LF expressed and secreted in A. oryzae has an iron binding capacity similar to authentic lactoferrin, an $^{59}Fe$ micro filter binding assay was developed. Purified human lactoferrin isolated from the growth medium of transformant #1 was dialyzed against 0.1M citric acid (pH 2.0) to generate apo-human LF. Native lactoferrin from human milk was treated similarly. Excess $^{59}Fe$ (0.2 mCi) was added to these samples in an equal volume of 1 M bicarbonate, followed by incubation at 37° C. for 30 minutes. Samples were applied to nitrocellulose membrane and washed several times with bicarbonate. The filter was visualized by autoradiography and Fe-binding was quantitated using a betagon blot analyzer. As illustrated in FIG. 11B, both recombinant and native LF showed a similar level of iron binding at all concentrations tested. The results demonstrate that recombinant human LF is indistinguishable from native human LF in its capacity to bind iron.

With reference to FIGS. 2A through 2D, the complete cDNA sequence for human lactoferrin protein is depicted. The cDNA coding for lactoferrin is used to create plasmids and transform eucaryotic cells and to produce the lactoferrin protein.

Strains of Aspergillus used in the present invention are auxotrophic mutants that contain a defective pry4 gene that results in an inability to synthesis orotidine 5' phosphate (OMP) decarboxylase. The enzyme is required for uridine synthesis. The strain cannot grow on media lacking uridine. The plasmid contains a selectable marker, i.e., a sequence that encodes the gene for OMP decarboxylase. Uptake of the plasmid by the Aspergillus can therefore be selected for by growth on media lacking uridine. The Aspergillus is transformed by the plasmid such that it can grow on the uridine deficient media.

EXAMPLE 10

EXPRESSION OF THE 3' IRON-BINDING DOMAIN OF HUMAN LACTOFERRIN—E. COLI

The 3' iron-binding domain of human lactoferrin (hLF) was expressed in Escherichia coli using the bacterial expression plasmid, PT7-7 as described by Tabor, S. and Richardson, C., Proc. Natl. Acad. Sci. U.S.A., 82:1074–1078 (1985). pGEMhLFc, containing the cDNA for the complete hLF cDNA (Ward, P.P., et al. Gene. 122:219–223 (1992)), was digested with Sma I and Hind III to release a 1.5 kb fragment encoding the 3' iron-binding domain of hLF. This 1.5 kb Sma I/Hind III fragment was subcloned in-frame into Sma I/Hind II digested P77-7, under the control of the strong inducible T7 promoter, generating PT7-7hLF3'

PT7-7hLF3' was transformed into a protease deficient strain of E. coli which had previously been transformed with pGP1-2 plasmid which contained the 17 polymerase under the control of the λpL promoter as described by Conneely, O. M., et al. In: Hornone Action and Molecular Endocrinology. 5-48–5-50 (1989)). The PT7-7 plasmid contained an ampicillin resistance gene while the pGP1-2 plasmid contained a kanamycin resistant gene allowing dual antibiotic resistance selection for transformants containing both plasmids. Transformants obtained were cultured overnight in LB broth containing ampicillin (50 µ/ml) and kanamycin (50 µg/ml) at 30° C./250 rpm. Overnight cultures were subcultured into LB (500 ml) containing ampicillin and kanamycin and grown at 30° C./250 rpm until an $O.D._{600}nm$ of 0.5–0.6 was obtained. At 30° C. the λ repressor bound to the λpL promoter, thus blocking T7 polymerase production. Induction of the recombinant protein was achieved by raising the temperature to 42° C. for one hour to inactivate the λ repressor thus allowing T7 polymerase production. The temperature was lowered to 30° C. for a further two hours, turning off λpL directed transcription and allowing the production of the recombinant protein as the T7 polymerase bound to the T7 promoter to specifically induce expression of the recombinant lactoferrin 3' iron-binding domain.

Western Immunoblot analysis was performed to determine if the 3' iron binding domain was expressed in the bacterial cells under the control of the T7 promoter and to monitor its purification. The cells were harvested at 5000 g and resuspended in 15 ml of PBS (pH 7.4). Total cellular extracts were prepared by sonication for 1 minute on ice. The sonicate was centrifuged at 13,000 g for 40 minutes at 4° C. The supernatant was removed and the pellet was resuspended in 50 ml of denaturation buffer (5M urea, 2% triton, 5 mM EDTA, 0.01% Tween 20, 50 mM TrisCl, pH 7.5) and centrifuged at 48,000 g for one hour. The supernatant containing the soluble fraction was recovered. Protein concentration was determined using the Bradford reagent according to manufacturers instructions (BioRad, Richmond, Calif.). Protein samples (40 µg) were resolved by SDS-PAGE and transferred to a nitrocellulose filter electrophorectically using the Western Inmmunoblot procedure. The filter was blocked with Tris-buffered saline (TBS, 0.05 M Tris/0.15 M NaCl, pH 7.5) containing 2% dried milk, and then incubated for 2 hours in the same with the addition of a specific polyclonal IgG (1 µg/ml) directed against hLF (Sigma, St. Louis, Mo.). The filter was washed (5×10 min) in TBS/0.05% Nonidet P-40 followed by incubation with 5 µCi of $^{125}I$ protein A in TBS/2% dried milk. The filter was washed (5×10 min) in TBS/0.05% Nonidet P-40, dried and exposed overnight in Kodak XAR5 film at −70° C. The film was developed by autoradiography.

Figure 10:
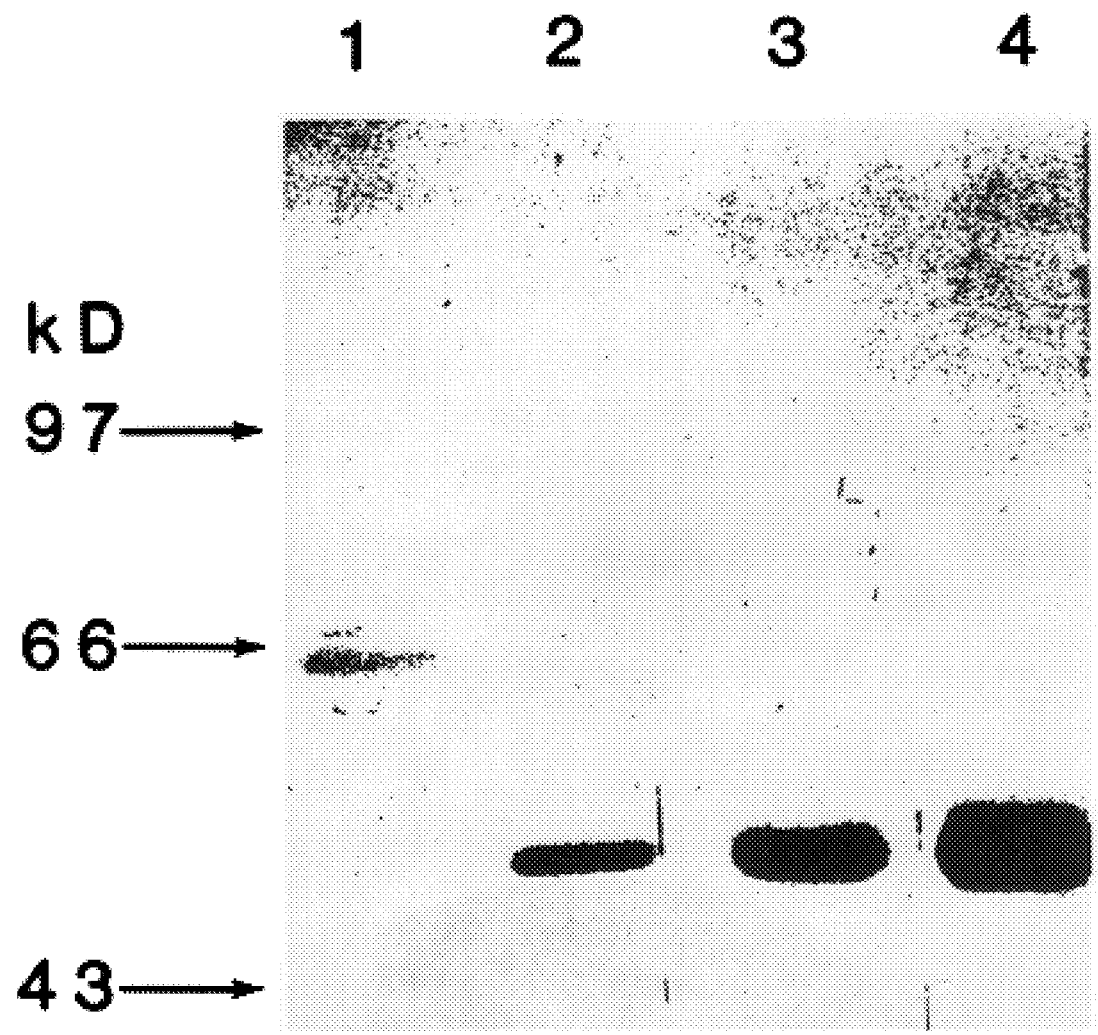
FIG. 10 is a western immunoblot of cellular extracts of transformed *E. coli* cells expressing the C terminal fragment of LF.

The results of the Western analysis are shown in FIG. 10. An immunoreactive band at the expected size (50 kDa) for the hLF 3' iron-binding domain was evident in the cellular extract from induced cells and was absent in control uninduced cells (FIG. 10, lanes 1 and 2). The hLF 3' iron-binding domain associates with the cellular homogenate insoluble fraction (FIG. 10, lane 3) and hence required a further solubilization step in a denaturation buffer to prepare the hLF in a soluble form (FIG. 10, lane 4).

Figure 11:
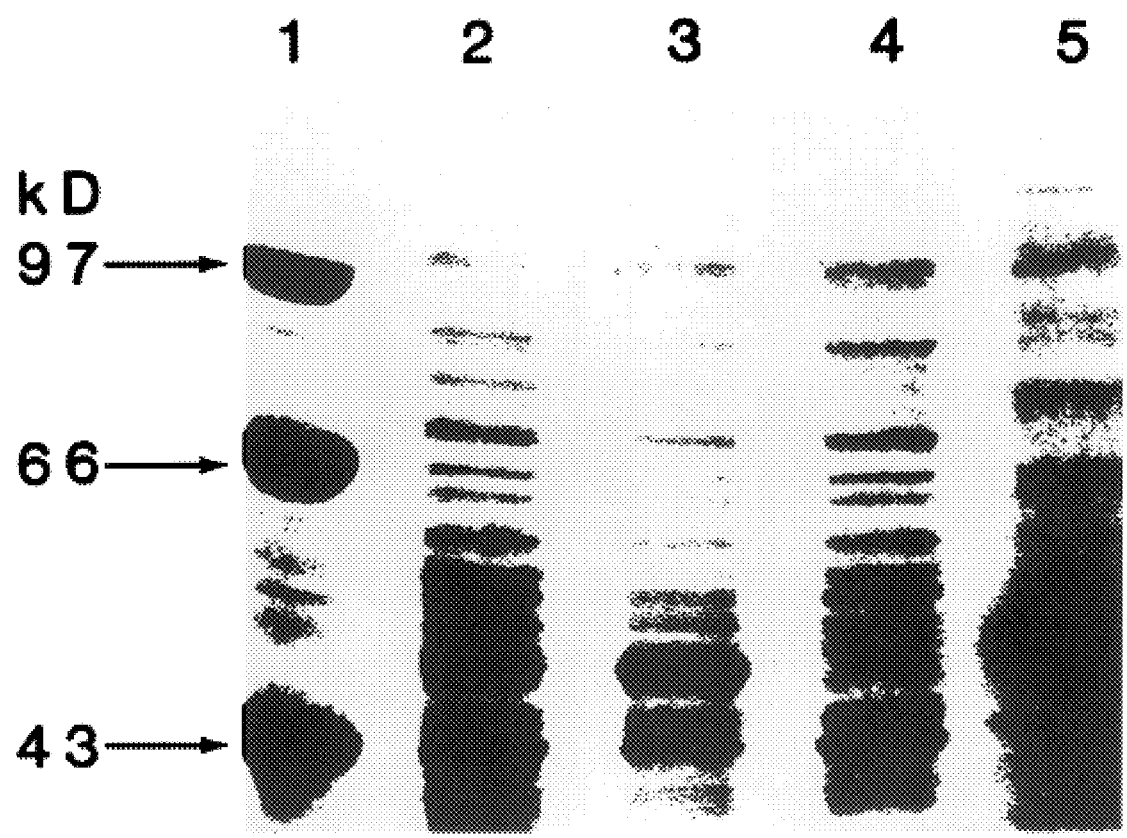
FIG. 11 shows the coomassie-stained SDS-PAGE analysis of extracts of transformed *E. coli* cells expressing the C terminal fragment of LF.

Analysis of a coomassie-stained SDS-PAGE gel also showed the presence of a 50 kDa protein in the cellular extract from induced cultures which was absent in control uninduced cultures (FIG. 1, lanes 2 and 3). The recombinant protein was expressed at levels up to 10 mg/l and represented approximately 5% of the total cellular protein. The hLF 3' iron-binding domain did not associate with the soluble homogenate fraction (FIG. 11, lane 4) and hence required a further solubilization step in a denaturation buffer to prepare the hLF in a soluble form (FIG. 11, lane 5). Purification and solubilization of the recombinant hLF 3' iron-binding domain resulted in a 50% yield of recoverable protein and represented the major protein band in this fraction.

In summary, we have successfully produced recombinant hLF 3' iron-binding domain in *E. coli* under the control of the strong inducible T7 promoter. The recombinant protein was expressed and purified in a soluble form from the cellular extracts at levels up to 5 mg/l.

EXAMPLE 12

EXPRESSION AND PURIFICATION OF AN N-TERMINAL LACTOFERRIN FRAGMENT (AA 1-52) IN *ESCHERICHIA COLI*

An N-terminal human lactoferrin fragment (AA 1-52), encoding the bactericidal domain of hLF, reported by Bellamy et al., supra, was expressed and purified from *E. coli*. The bovine lactoferrin fragment also reported by Bellamy, et al. is produced by the same method illustrated here for the human fragment. This was achieved using the glutathione S-transferase (GST) Gene Fusion System (Pharmacia, Piscataway, N.J.) where the lactoferrin fragment was expressed as a fusion protein with glutathione S-transferase [Smith, D. S., et al., *Gene*, 67:31–40 (1988)] and a protease cleavage site allowing production of the bactoricidal domain by cleavage from GST.

A 156 bp human lactoferrin fragment encoding AA 1-52, containing Sma I/BamH I ends was obtained by polymerase chain reaction (PCR) amplification of pGEMhLFc plasmid DNA [Ward, P. P., et al., *Biotechnology*, 10:784–789 (1992)]. The oligonucleotide primers used were as follows:

5' end oligonucleotide as shown in SEQ. ID. NO. 11
    CTGCCCGGGCGTAGGAGAAGGAGTGTT 3' end oligonucleotide as shown in SEQ. ID. No. 12
    CATGGATCCTGTTTTACGCAATGGCCTG-GATACA This PCR fragment was digested with Sma I and BamH I and repaired using the Klenow Fragment of DNA polymerase I. This fragment was subcloned into BamH I repaired pGEX-3X generating pGEX-3XLFN-1. This fused the lactoferrin cDNA fragment in frame, downstream from the glutathione S-transferase gene and under the control of the strong, inducible tac promoter. All PCR amplified products and construction junctions were sequenced using the commercially available Sequenase version 2.0 kit (United states Biochemical Corp, Cleveland, Ohio).

pGEX-3XLFN-1 was transformed into the bacterial strain, JM109. Transformants obtained were cultured overnight in LB (50 ml) containing ampicillin (50 g/ml) at 37° C./250 rpm. Overnight cultures were subcultured into LB (500 ml) containing ampicillin (50 g/ml) and grown at 37° C./250 rpm until an OD600nm of 0.6–0.8 was obtained. Isopropyl-D-thiogalactopyranoside (IPTG) was added to the culture medium at a concentration of 1 mM to turn on the tac promoter resulting in expression of the glutathione S-transferase/LFN-1 fusion protein. Growth under these conditions continued for 4 hours after which the cells were harvested at 5,000 g and resuspended in 5 ml of MTPBS (150 mM NaCl, 16 mM $Na_2HPO_4$, 4 mM $NaH_2PO_4$, 1% Triton X-100, pH 7.3). Total cellular extracts were prepared by 3×1 minute freeze/thaw cycles followed by mild sonication for 2×1 minute. The sonicate was centrifuged at 13,000 g for 20 minutes and the supernatant obtained was applied to a glutathione sepharose 4B column following manufacturer's instructions (Pharmacia, Piscataway, N.J.). The glutathione S-transferase/LFN-1 fusion protein was eluted from the column using 10 ml of elution buffer (10 mM glutathione, 50 mM Tris pH 8.0). Fractions of 1.5 ml were collected and dialyzed overnight against 50 mM Tris, 15% glycerol pH 8.0.

Figure 12A:
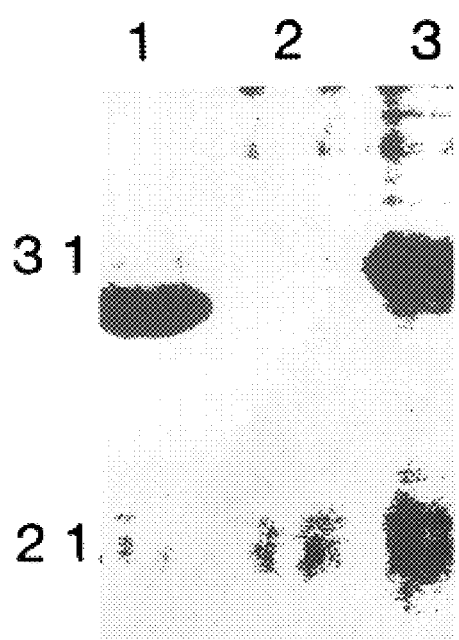
FIGS. 12A through 12B collectively show the expression and purification of the glutathione S-transferase/LFN-1 fusion protein.
Figure 12B:
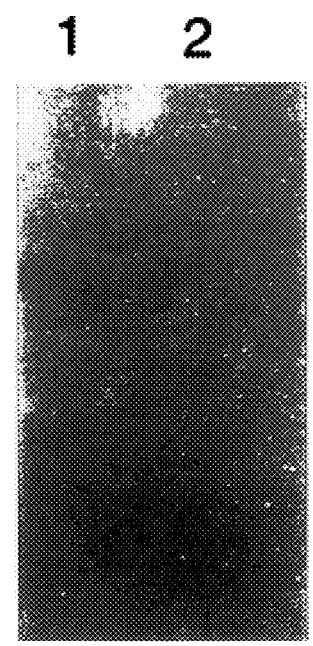

Samples from the solubilized extracts and the purification fractions were analyzed by SDS/PAGE followed by silver-staining. The results of this analysis are shown in FIGS. 12A through 12B. A band at the expected size (32 kDa) for the glutathione S-transferase/LFN-1 fusion protein was detected in the solubilized protein extracts from induced JM109 cultures transformed with pGEX-3X/LFN-1 and was absent in uninduced cultures (FIG. 12A, lanes 2 and 3). This band migrates at a higher mobility than control induced JM109 cultures transformed with pGEX-3X alone (FIG. 12A, lane 1). The fusion protein was successfully purified to homogeneity over a glutathione sepharose 4B column (FIG. 12B, lanes 1 and 2). Protein concentration determination using the Bradford reagent (BioRad, Richmond, Calif.) showed that the glutathione S-transferase/LFNI fusion protein was purified at levels up to 5 mg/l. The GST fusion protein has a protease cleavage site for the protease Kex II between GST and the 52 amino acid protein.

In summary, a human lactoferrin fragment, encoding a bactericidal domain of this protein, has been successfully expressed as a fusion protein with glutathione S-transferase an *E. coli* expression system. This fusion protein was purified to homogeneity at levels up to 5 mg/l. The bactericidal protein is obtained by cleavage with the protease Kex II to cleave the GST portion from the bactericidal domain.

EXAMPLE 13

EXPRESSION OF BOVINE AND PORCINE LACTOFERRIN IN *ASPERGILLUS ORYZAE*

A universal *A. Oryzae* expression vector is constructed to allow in frame subcloning of any cloned cDNA of interest. This vector, pAG, is similar to the vector pAhLFG(+1) utilized for the expression of human lactoferrin in *A. Oryzae* above. A 680 bp α-amylase fragment encoding the promoter, signal sequence and the alanine residue from the start of the mature α-amylase II gene, is obtained by polymerase chain reaction (PCR) amplification of pAhLFG(+1). The oligonucleotide primers are as follows:

5' end oligonucleotide, SEQ. ID. NO. 13
    5'CGGAATTCATGGTGTTTGATCATTTT

3' end oligonucleotide, SEQ. ID. NO. 14
    5'TGGAATTCGATCGCGGATCCGCAATG-CATGCAGCCAAAGCAGGTGCCGCGAC The 5' end oligonucleotide encodes an EcoR I site and the 3' end oligonucleotide contains an Nsi I site, flanked by a BamH I site. This amplified DNA is digested with EcoR I and BamH I and subcloned into EcoR I/BamH I digested pAhLFG(+1) generating pAG. All PCR amplified products and construction junctions are sequenced using the commercially available Sequenase version 2.0 kit (United States Biochemical Corp., Cleveland, Ohio).

Figure 13:
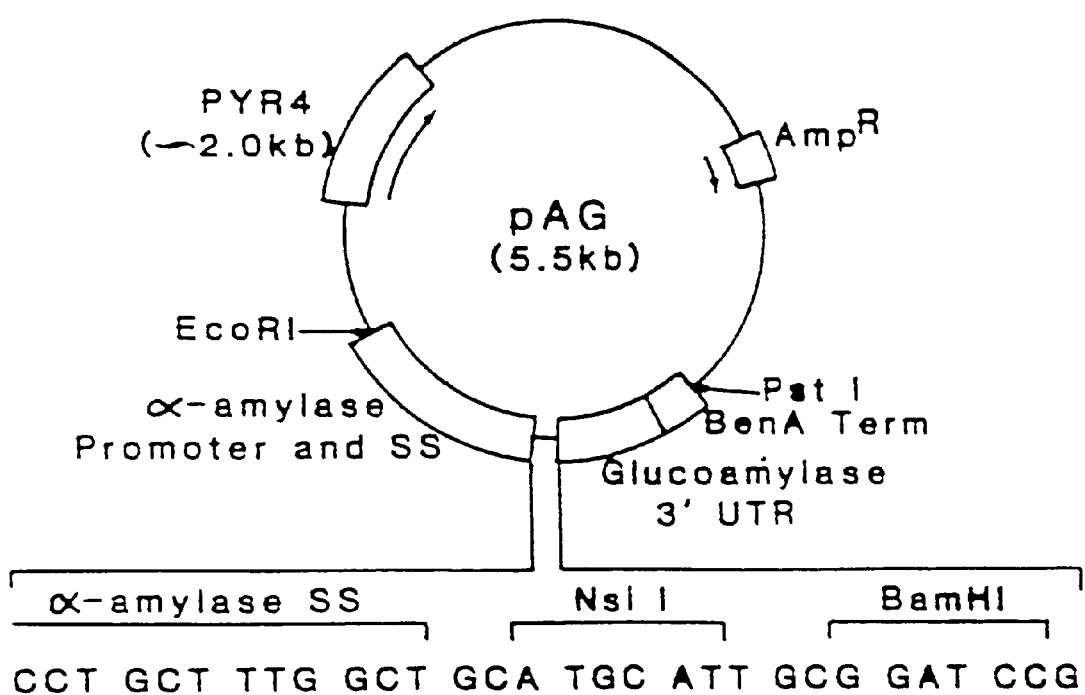
FIG. 13 Schematic representation of the *A. Oryzae* universal expression plasmid, pAG.

A schematic representation of this expression plasmid is outlined in FIG. 13. Restriction enzyme digestion of this expression plasmid with Nsi I, followed by repair using DNA polymerase I allows subcloning of any cDNA of interest in frame with the α-amylase signal sequence and alanine residue from the start of the mature α-amylase II gene. 5' and 3' oligonucleotide primers are designed to contain Acc 1 ends, and used to obtain the full length cDNA encoding for mature porcine and bovine lactoferrin using polymerase chain reaction (PCR) amplification of their known DNA sequence. The PCR fragment thus obtained is digested with Acc I and repaired using the Klenow fragment of DNA polymerase I for in frame subcloning into Nsi I blunt-ended pAG. The plasmids are then be transformed into the pyrG-strain of *A. Oryzae* to obtain expression and secretion of these cDNAs as previously described for human lactoferrin.

EXAMPLE 14

EXPRESSION OF HUMAN LACTOFERRIN IN *SACCHAROMYCES CEREVISIAE*

The complete human lactoferrin (hLF) cDNA was expressed in *Saccharomyces cerevisiae* using the yeast expression plasmid, YEP [McDonnell, D. P. et al., *J. Steroid Biochem, Molec. Biol.*, 39:291–297 (1991)]. A 2.2 kb fragment encoding the complete hLF cDNA SEQ. ID No. 1 was generated using the polymerase chain reaction. This fragment contained and XhoI restriction enzyme site at its 5' end and an Asp718 restriction enzyme site at its 3' end. The 2.2 kb fragment was subcloned, in frame, into XhoI/Asp718 digested YEP to yield, YEPLFc.

Transcription of the hLF cDNA was under the control of the copper responsive yeast metallothionein promoter (CUP1). hLF was produced as a ubiquitin fusion protein. The fusion protein is short lived in the yeast cells and is processed to produce unfused protein upon folding.

YEPLFc was transformed into a protease deficient strain of *S. cerevisiae*, by standard techniques [Ito, H., et al., *J. Bacteriol.*, 153:163–186 (1983).] This strain cannot grow unless the growth medium is supplemented with adenine, uracil and tryptophan. The YEP plasmid contains a tryptophan selectable marker, thus, transformants were selected by tryptophan auxotrophy.

Transformants obtained were cultured overnight in selective medium containing 2% glucose, 0.1% casamino acids, 0.67% yeast nitrogen base, 0.001% adenine and 0.002% uracil at 30° C./200 rpm. When the cells reached an $OD_{600}$nm of 1.0, $1\times10^6$ cells were inoculated into 10 ml of the selective medium and 100 $\mu$m $CuSO_4$ added. The cells were grown for 24 hours at 30° C./200 rpm. The purpose of adding the $CuSO_4$ was to induce expression of the hLF cDNA from the copper inducible CUP1 promoter.

Western irimunoblot analysis was performed to determine if hLF was expressed in the yeast cells under the control of the CUP1 promoter. The cells were harvested by centrifugation at 5000×g for 5 min. and resuspended in 1 ml of Z buffer (120 mM $Na_2HPO_47H_2O$, 40 mM $NaH_2PO_4H_2O$, 10 mM KCl, 1 mM $MgSO_47H_2O$, 0.27% 2-mercaptoehanol, pH 7.0). Total cellular extracts were prepared by glass bead homogenization. This procedure involved mixing the yeast cells with an equal volume of glass beads (0.5 mm, B.Braun Instruments) and vortexing for 5×1 min. The homogenate was centrifuged at 13,000 g for 10 min. and the supernatant removed. The protein concentration was determined using the Bradford reagent in accordance with the manufacturer's instructions (BioRad, Richmond, Calif.). Protein samples (50 $\mu$g) were resolved by SDS-PAGE and electrophoretically transferred, overnight, to a nitrocellulose filter using the western immunoblot procedure. The filter was blocked with tris-buffered saline (TBS=0.05M Tris/0.15M NaCl, pH 7.5) containing 1% dried milk and then incubated overnight, in the same, with the addition of a specific rabbit polyclonal antibody (1 $\mu$g/ml) directed against hLF (Signa, St. Louis, Mo.). The filter was washed in TBS/0.1% Tween 20 (5×5 min.) followed by incubation with horseradish peroxidase (Amersham, UK) for 1 hour. The filter was washed in TBS/0.3% Tween 20 (3×5 min.) and then TBS/0.1% Tween 20 (3×5 min.). The filter was then treated with luminol and enhancer (Amersham, UK) for 1 min., dried and exposed for 1 min. to X-ray film. The film was developed by autoradiography.

These data demonstrate successful production of recombinant hLF in *S. cerevisiae* under the control of the copper inducible (CUP1) promoter.

Figure 16:
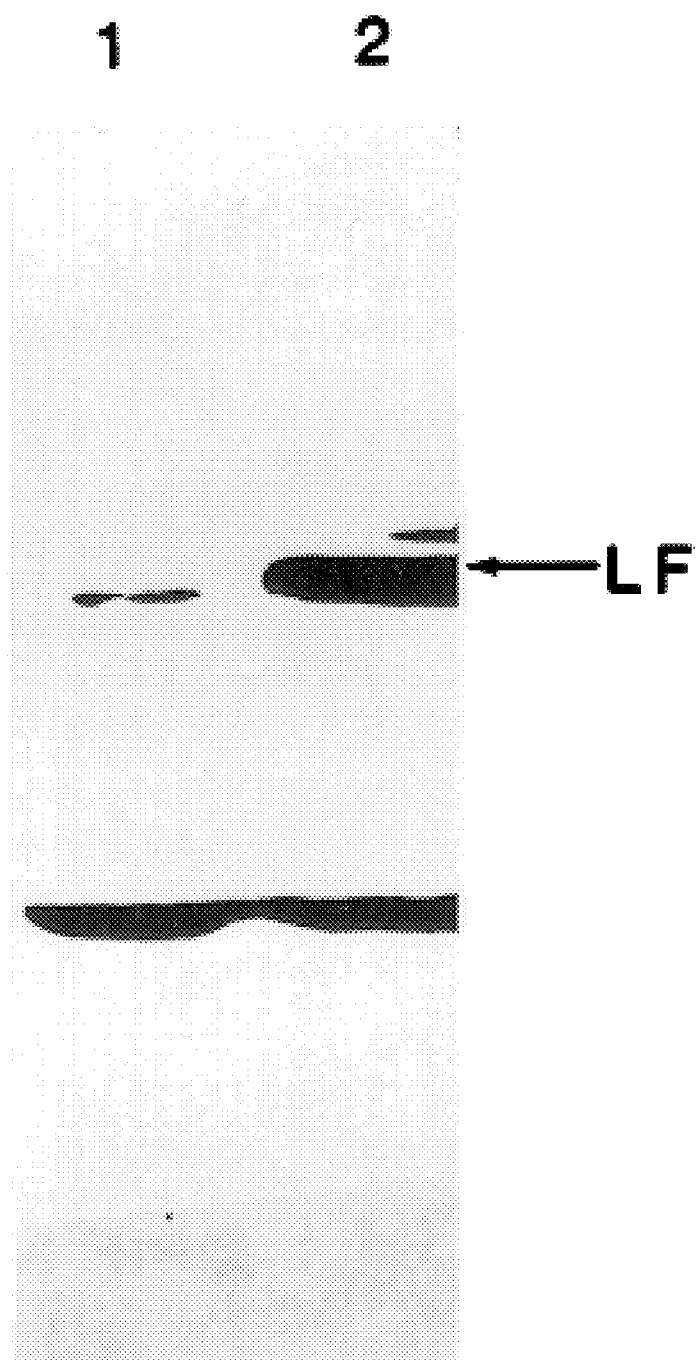
FIG. 16 is a Western blot showing hLF expression in *Saccharomyces Cervisiae*.

The results of the western analysis are shown in FIG. 16. An immunoreactive band at the expected size (78 kDa) for hLF was evident in the cellular extract from transformed *S. Cerevisiae* cells. FIG. 16, lane 1.

EXAMPLE 15

EXPRESSION OF hLF IN *ASPERGILLIS NIDULANS*

Construction of the *Aspergillis Nidulans* Expression Plasmid

Figure 17:
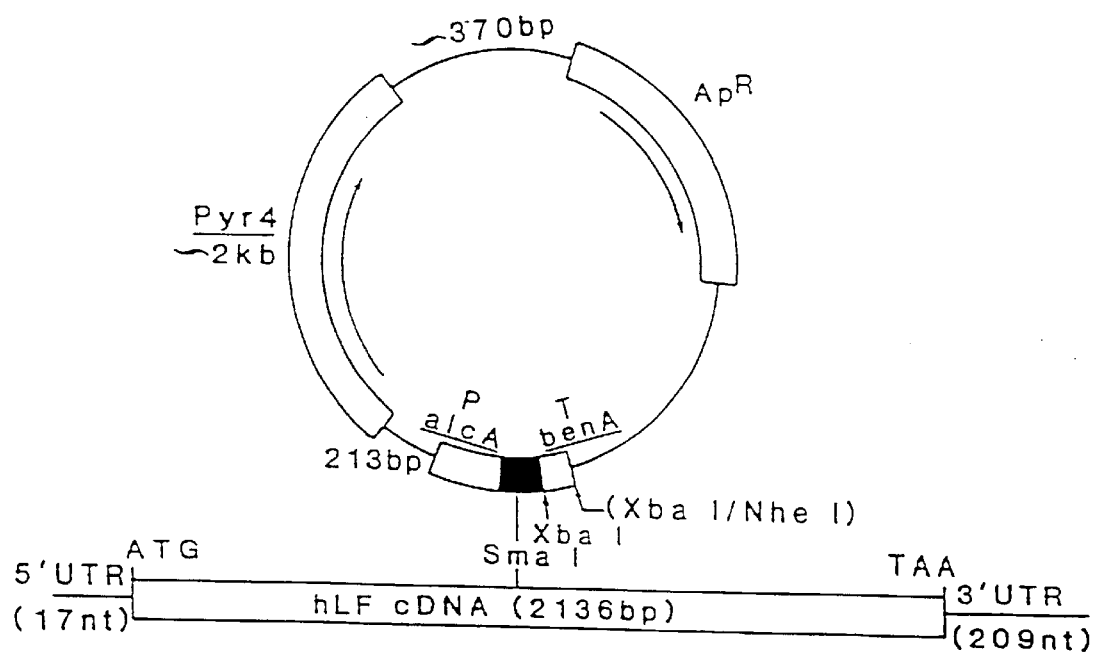
FIG. 17 is a schematic of the plasmid used for expression of the cDNA (SEQ. ID No. 1) in *Aspergillis Nidulans*.

The plasmid used for expression of hLF cDNA is shown schematically in FIG. 17. The cDNA of SEQ. ID No. 1 as a 2.3-kb clone contained the secretory signal sequence and complete translation frame. The sequence of the entire cDNA was confirmed by dideoxy sequence analysis (Sequenase version 2.0, U.S. Biochemical, Cleveland, Ohio). The cDNA was repaired using the PolIk and subcloned into AccI-digested and blunt-ended pGEM4. The plasmid, pGEMhLF, was digested with HindIII+Asp718 and repaired using PolIk. The resulting 2.3-kb hLF fragment was subcloned into a unique SmaI site located in the multiple cloning cassette of pAL3 downstream from the alcA promoter, Waring, R. B., et al., *Gene*, 79, 119–130 (1989), generating pAL3hLF. The β-tubulin transcription terminator fragment was obtained by digesting the 3'-untranslated region of the bena gene (nt 2569–2665; May et al., 1987) with XbaI+NheI and subcloned into XbaI-digested pAL3hLF generating pAL3hLFT. This plasmid was used to transform *A. nidulans* strain GR5 (pyrG89; wa3; pyroA4)

The *A. nidulans* expression plasmid, pAL3hLFT, contains 300 bp of 55'-flanking sequence of the *A. nidulans* alcA gene containing all the regulatory elements necessary for controlled gene expression. To construct pALhLFT, a 2.3-kb hLF cDNA fragment containing 17 nucleotides of 5'-UTR, the complete hLF ORF encoding the secretory signal peptide and mature hLF, followed by 209 nt of 3' UTR was subcloned into a unique SmaI site in pAL3 downstream from the alcA promoter. A 96-bp terminator fragment from the *A. nidulans* β-tubulin-encoding (benA) gene was subcloned into a unique XbaI site downstream from the hLF cDNA sequence. The plasmid also contains an $Ap^R$ maker and the *N. crassa* pyr4 selectable marker (Waring et al., supra, 1989).

Transformation and Southern analysis

Transformation was carried out as described by May et al., *J. Cell Beol.*, 109, 2267–2274 (1989). Protoplasts were transformed with 3 $\mu$g of the expression plasmid with an efficiency of 40 transformants/$\mu$g DNA. Transformats obtained were purified three times through conidial spores. Southern blot analysis was performed to confirm that transformants contained integrated plasmid with hLF cDNA. A hLF-specific radiolabelled band was detected at the expected size (2.3 kb) in lanes 1–10 but not in DNA from control spores. These results demonstrate that hLF cDNA was integrated into the genome of all *A. nidulans* transformants tested and varied randomly from one copy (transformants Nos. 3, 6 and 10) to 20 copies (No. 5) per cell. The site of integration of the plasmid into the *A. nidulans* genome is random due to the absence of homologous sequences to target the vector into a particular site.

Southern blot analysis was conducted of transformed *A. nidulans*. Genomic DNA was isolated from ten individual *A. nidulans* (GR5) transformats and untransformed spores as described by Rasmussen, C. D. et al., *J. Biol. Chem.*, 265, 13767–13775 (1990). The DNA (1 μg) was digested with EcoRI, size fractionated on a 0.8% agarose gel and transferred to a nitrocellulose filter and hybridized with a radio-labelled hLF cDNA probe (2.1-kb). A sample (20 ng) of hLF cDNA was used as a positive control (hLF cDNA). Prehybridization and hybridization of the filter was performed in 6×SSC/0.1% SDS/0.5% dried milk at 65° C. for 16 h. The hybridization solution contained 200 ng of $^{32}$P probe (2.1 kb; specific activity 4×108 cpm/lg of DNA). Filters were washed in 2×SSC/0.5%SDS at 68° C. for 30 min followed by 0.5×SSC/0.5% SDS at 68° C. for 30 min. The filter was dried and exposed to Kodak X-AR5 film at −70° C. for 30 min and developed by autoadiograpy. The autoradiography showed an intense 2.1 kb band for hLF.

Production of hLF in *Aspergillus nidulans*

Conidia (1×10$^6$/ml) were cultured in minimal media utilizing 100 mM Na acetate pH 6.5 as carbon source with or without addition of 1.2% ethanol to induce transcription of the hLF cDNA. GR5 was cultured as above except for the addition of 5 mM uridine and 10 mM uracil. Media and mycelia were harvested and separated using Miracloth (Calbiochem, San Diego, Calif.). Mycelia (200 mg) were freeze-dried and lyophilized overnight. Total cellular extracts were prepared by homogenization in a glass teflon homogenizer using 1 ml of phosphate-buffered saline (PBS; 137 mM NaCl/2.7 mM KCl/4.3 mM Na$_2$HPO$_4$7H$_2$O/1.4 mM K$_2$HPO$_4$pH 7.4) in the presence of phenylmethylsulfonylfluorride (PMSF, 10 μg). The homogenate was centrifuged at 12000×g for 30 min at 4° C. and the supernatant containing the soluble fraction was recovered. The growth medium was concentrated by freeze drying and lyophilization and resuspended in 1/30 vol. in PBS pH 7.4. Protein concentration was determined using the Bradford reagent according to manufacturer's instructions (BioRad, Richmond, Calif.). Concentrated media samples containing 40 μg protein and soluble extracts (50 μg protein) were subjected to 0.1% SDS/7% PAGE, Laemmli, U.K., *Nature*, 227, 680–685 (1970). Purified lactoferrin (250 ng, Sigma, St. Louis, Mo.) was used as standard (hLF std). The resolved proteins were transferred to nitrocellulose filters electrophoretically using the Western blot procedure, Towbin, H., et al., *Proc. Natl. Acad. Sci. USA*, 76, 4350–4354 (1979). Filters were blocked with Tris-buffered saline (TBS, 0.05 M Tris/0.15 M NaCl pH 7.5) containing 2% dried milk and then incubated by 2 h in the same with the addition of a 1 μg/ml of a specific polyclonal IgG directed against hLF (Sigma, St. Louis, Mo.). Filter washes (5×10 min) were in TBS/0.05% Nonidet P-40 followed by incubation with 1 μCi of [$^{125}$I] protein A in BS/2% dried milk. The filter was washed (5×10 min) with TBS/0.05% Nonidet P-40, dried and exposed overnight to Kodak XAR5 film at −70° C. The film was then developed by autoradiography. The autoradiographs demonstrate production of hLF. Western analysis was performed to determine if the hLF cDNA was expressed in the *A. nidulans* transfornats under the control of the alcA promoter.

Conidia (1×10$^6$/ml) from transformat No. 5, which contained the highest number of copies of integrated hLF cDNAs, and from untransformed GR5 were inoculated into minimal medium utilizing glucose as the carbon source. After 18 h, the cultures were harvested, washed and reinoculated into minimal medium supplemented with 1.2% ethanol and grown for an additional 12 or 24 h before harvesting the cultures. Cell extracts and samples of the growth medium were resolved by SDS-PAGE, transferred to nitrocellulose and immunoblotted using a specific polyclonal IgG directed against hLF. An immunoreactive band indistinguishable from native hLF was evident in the cells and growth medium from transformat No. 5 after 12 and 24 h growth only after ethanol induction. Cell extracts or growth medium obtained from untransformed GR5 did not contain an immunoreactive band even after addition of ethanol. These results demonstrate that hLF is expressed in transformed *A. nidulans* under the control of the alcA promoter.

Western analysis revealed hLF in the cells in all of the remaining transformants. In general there was a correlation between the plasmid copy number and the expression levels obtained. In the medium hLF was detected only with transformats containing multiple copies of integrated expressed plasmid (Nos. 1, 5, 7 and 10).

In order to monitor the levels of hLF produced in the system, a pilot fermentation of transformant No. 5 was carried out using the growth parameters described above. ELISA analysis, Vilja, P., et al., *J. Immunol. Methods*, 76, 73–83 (1985), using a specific biotinylated IgG directed against hLF demonstrated that the total level of recombinant hLF produced was 5 μg/ml with approx. 30% (1.5–2.0 μg/ml) of this material secreted into the medium.

Iron Binding Analysis of hLF.

To test if recombinant lactoferrin synthesized and secreted in *A. nidulans* has an iron binding capacity similar to authentic human lactoferrin, samples of the growth medium of transformant No. 5 and untransformed GR5 spores were examined using an $^{59}$Fe microfilter-binding assay to detect $^{59}$Fe-bound lactoferrin. Iron-binding ($^{59}$Fe) is detected in the medium from transformant No. 5 but not in the medium from control untransformed GR5 spores. These results indicate that hLF produced in *A. nidulans* is biologically active in its capacity to bind $^{59}$Fe.

The data demonstrate the successful production of biologically active hLF in *A. nidulans*. The levels of hLF produced in *A. nidulans* were approx. 5 μg/ml with 30% of the hFL secreted into the growth medium. The secreted hLF was identical to native breast milk LF with regard to size and immunoreactivity. Furthermore, the hLF was capable of binding iron. Although hLF has been reported to contain anti-fungal properties, neither the re-hLF nor native hLF when added to the growth medium, retarded the growth of this strain of *A. nidulans*. The production of biologically active hLF in *A. nidulans* will facilitate testing of possible nutritional and therapeutic uses of this protein.

EXAMPLE 16

PRODUCTION OF DNA SEQUENCE SUBSTITUTION ANALOGS

FIGS. 18A through 18N collectively depict the restriction enzyme cleavage sites in the SEQ I.D. No. 1 cDNA for cleavage by various endonucleases. Table 2 lists the alternative codons that code for the 20 common amino acids. DNA sequence substitution analogs that also code for human lactoferrin can be constructed by choosing alternate codons from Table 2 to alter the DNA Sequence between a pair of cleavage sites selected from FIG. 18A through 18N. Alternative codons are assembled into a synthetic oligonucleotide by conventional methods and the synthetic oligo is substituted into the endonuclease treated DNA of Sequence ID. No. 1 by the methods described in "Molecular Cloning. A Laboratory Manual", 2d Edition, Cold Spring Harbor Laboratory Press (1989), to produce a substitution analog. Other methods generally known to those skilled in the art can also be employed to obtain substitution analogs of DNA sequences. The alteration of the DNA by cleavage and codon substitution maybe repeated to substitute substantial portions of the original DNA sequence with alternative codons without altering the protein expressed by the DNA of Sequence ID. No. 1. The same methods can of course be used to make substitution analogs of the cDNA of SEQ ID No. 3 and 5. Alteration of a DNA sequence which produces no change in the protein expressed by the DNA sequence might, for example, be conducted to increase protein expression in a particular host cell by increasing the occurrence of codons that correspond to amino acid tRNAs found in higher concentration in the host cell. Such altered DNA sequences for substitution analogs can be easily produced by those of ordinary skill in the art following the method set out above, or other alternative techniques for altering the DNA sequence while obtaining the same protein on expression. Substitution analogs can be obtained by substitution of oligonucleotides at restriction cleavage sites as described above, or by other equivalent methods that change the codons while preserving the amino acid sequence of the expressed protein.

TABLE 2

| AMINO ACID | CODONS |
|---|---|
| Phe | TTT |
|  | TCC |
| Leu | TTA |
|  | TTG |
|  | CTT |
|  | CTC |
|  | CTA |
|  | CTG |
| Ile | ATT |
|  | ATC |
|  | ATA |
| Met | ATG |
| Val | GTT |
|  | GTC |
|  | GTA |
|  | GTG |
| Ser | TCT |
|  | TCC |
|  | TCA |
|  | TCG |
|  | AGT |
|  | AGC |
| Pro | CCT |
|  | CCC |
|  | CCA |
|  | CCG |
| Thr | ACT |
|  | ACC |
|  | ACA |
|  | ACG |

TABLE 2-continued

| AMINO ACID | CODONS |
|---|---|
| Ala | GCT |
|  | GCC |
|  | GCA |
|  | GCG |
| Tyr | TAT |
|  | TAC |
| Gly | GGT |
|  | GGC |
|  | GGA |
|  | GGG |
| His | CAT |
|  | CAC |
| Gln | CAA |
|  | CAG |
| Asn | AT |
|  | AAC |
| Lys | AAA |
|  | AAG |
| Asp | GAT |
|  | GAC |
| Glu | GAA |
|  | GAG |
| Cys | TGT |
|  | TGC |
| Trp | TGG |
| Arg | CGT |
|  | CGC |
|  | CGA |
|  | CGG |
|  | AGA |
|  | AGG |
| TERMINATION SIGNALS | TAA |
|  | TAG |
|  | TGA |

In conclusion, it is seen that the present invention and the embodiments disclosed herein are well adapted to carry out the objectives and obtain the end set forth in this application. Certain changes can be made in the method and apparatus without parting from the spirit and scopes of this invention. It is realized that changes are possible and that it is further intended that each element or step presided in any of the filing claims is to be understood as to referring to all equivalent elements or steps for accomplishing the essentially the same results in substantially the same or equivalent manner. It is intended to cover the invention broadly in whatever form its principles may be utilized. The present invention, therefore, is well adapted to carry out the objects and obtain the ends and advantages mentioned, as well as others inherent therein.

We claim:

1. A process for producing lactoferrin which comprises culturing a transformant eucaryotic cell containing a recombinant plasmid, said plasmid comprising a plasmic vector having a polydeoxyribonucleotide which codes for a lactoferrin protein in a suitable nutrient medium until the lactoferrin protein is formed and isolating the lactoferrin protein.

2. A method for producing biologically active recombinant lactoferrin comprising the steps of:
   combining sequences containing a selectable marker gene, a promotor, a transcription termination sequence, and a linker sequence;
   cloning said sequences to form a plasmid;
   digesting said plasmid with a restriction endonuclease;
   inserting a cDNA coding for human, bovine or porcine lactoferrin into a restriction site; and
   transforming a cell with said plasmid to produce said recombinant lactoferrin.

3. The method of claim 2, wherein said promotor is selected from the group consisting of alcohol dehydrogenase, argB, α-amylase, glucoamylase, and benA.

4. The method of claim 2, wherein said transcription termination sequence is selected from the group consisting of α-amylase, glucoamylase, alcohol dehydrogenase and benA.

5. The method of claim 2, wherein said linker sequence is selected from the group consisting of α-amylase, glucoamylase and lactoferrin.

6. A method for producing biologically active recombinant lactoferrin comprising the steps of:
   combining sequences containing a selectable marker gene, a promotor, a transcription termination sequence, and a linker sequence;
   cloning said sequences to form a plasmid;
   digesting said plasmid with a restriction endocnuclease;
   inserting a substitution analog of a cDNA sequence selected from the group consisting of SEQ. ID No. 1 into a restriction site; and transforming eucaryotic cells with said plasmid expressing lactoferrin cDNA which produces said recombinant lactofemin.

7. The method of claim 6, wherein said selectable marker gene is selected from the group consisting of pyr4, pyrG, andS, argB and trpC.

8. A recombinant lactoferrin produced by the method of claim 6.

9. The method of claim 6, wherein said promotor is selected from the group consisting of alcohol dehydrogenase, argB, α-amylase, glucoaznylase, and benA.

10. The method of claim 6, wherein said transcription termination sequence is selected from the group consisting of α-amylase, glucoamylase, alcohol dehydrogenase and benA.

11. The method of claim 6, wherein said linker sequence is selected from the group consisting of α-amylase, glucoamylase and lactoferrin.

* * * * *

UNITED STATES PATENT AND TRADEMARK OFFICE
CERTIFICATE OF CORRECTION

PATENT NO. : 6,635,447 B1  Page 1 of 1
DATED : October 21, 2003
INVENTOR(S) : Orla M. Conneely et al.

It is certified that error appears in the above-identified patent and that said Letters Patent is hereby corrected as shown below:

<u>Column 44,</u>
Line 66, please insert:
-- 12. The method of claim 1, wherein said selectable marker gene is selected from the group consisting of pryr4, pyrG, andS, argB and trpC. --

Signed and Sealed this

Eighteenth Day of May, 2004

JON W. DUDAS
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 6,635,447 B1 | Page 1 of 1 |
| APPLICATION NO. | : 09/633739 | |
| DATED | : October 21, 2003 | |
| INVENTOR(S) | : Orla M. Conneely et al. | |

It is certified that error appears in the above-identified patent and that said Letters Patent is hereby corrected as shown below:

On the title page item (60), please insert --which is a continuation in part of application No. 07/873,304 filed on April 24, 1992, now abandoned; 08/145,681 is also-- between the comma and the words a continuation in part of application No. 07/967,947, on line 4 of Related U.S. Application Data.

Please also remove from the face of the patent ", application No. 09/633,738, which is a continuation in part of application No. 07/878,307, filed on Apr. 24, 1992, now abandoned" from between now abandoned and the period, one lines 8-10 following Related U.S. Application Data.

Related U.S. Application Data should now read as follows:

--Divisional of application No. 08/456,108, filed on May 30, 1995, now Pat. No. 6,100,054, which is a divisional of application No. 08/145,681 filed on October 28, 1993, now Pat. No. 5,571,691, which is a continuation in part of application No. 07/873,304 filed on April 24, 1992, now abandoned; 08/145,681 is also a continuation in part of application No. 07/967,947, filed on October 27, 1992, now abandoned, which is a continuation of application No. 07/348,270 filed on May 5, 1989, now abandoned.--

Signed and Sealed this

Twenty-sixth Day of August, 2008

JON W. DUDAS
*Director of the United States Patent and Trademark Office*